US012582773B2

(12) United States Patent
Halpert et al.

(10) Patent No.: US 12,582,773 B2
(45) Date of Patent: Mar. 24, 2026

(54) URINE OUTPUT SENSING WITHOUT USE OF AN INDWELLING CATHETER, AND ASSOCIATED SYSTEMS, DEVICES, AND METHODS

(71) Applicant: REPRIEVE CARDIOVASCULAR, INC., Milford, MA (US)

(72) Inventors: Andrew V. Halpert, Brookline, MA (US); Antony Jonathan Fields, San Francisco, CA (US); Eric Conley, York, ME (US); Mark Richard Pacyna, Edina, MN (US); Megha Shah, Milford, MA (US); Jeffrey Testani, New Haven, CT (US)

(73) Assignee: Reprieve Cardiovascular, Inc., Milford, MA (US)

( * ) Notice: Subject to any disclaimer, the term of this patent is extended or adjusted under 35 U.S.C. 154(b) by 0 days.

(21) Appl. No.: 19/054,756

(22) Filed: Feb. 14, 2025

(65) Prior Publication Data

US 2025/0262380 A1    Aug. 21, 2025

Related U.S. Application Data

(60) Provisional application No. 63/554,744, filed on Feb. 16, 2024.

(51) Int. Cl.
*A61M 5/172* (2006.01)
*A61M 5/168* (2006.01)

(52) U.S. Cl.
CPC ...... *A61M 5/1723* (2013.01); *A61M 5/16877* (2013.01); *A61M 2205/3303* (2013.01); *A61M 2205/3379* (2013.01)

(58) Field of Classification Search
None
See application file for complete search history.

(56) References Cited

U.S. PATENT DOCUMENTS 3,954,010 A    5/1976  Hilblom
4,132,644 A    1/1979  Kolberg
(Continued)

FOREIGN PATENT DOCUMENTS

EP        0258690       3/1998
EP        1986007      10/2008
(Continued)

OTHER PUBLICATIONS

Felker et al., "Diuretic Therapy for Heart Failure Patients," American College of Cardiology, Mar. 9, 2020, 4 pages.
(Continued)

*Primary Examiner* — Manuel A Mendez
(74) *Attorney, Agent, or Firm* — Perkins Coie LLP

(57) ABSTRACT

The present disclosure generally relates to fluid therapy based on patient data, and associated systems, devices, and methods. Embodiments of the present technology can obtain multiple inputs of urine output volume data from a patient without using an indwelling catheter, determine an accumulated volume of urine output data based on the obtained multiple inputs, and adjust the patient's fluid therapy based on the accumulated volume and/or the obtained multiple inputs. Additionally, or alternatively, embodiments of the present technology can include one or more sensors that measure a volume and/or a change in volume of urine within the patient's bladder to determine a urine output rate of the patient, without using an indwelling catheter. Accordingly, embodiments of the present technology can advantageously manage a fluid therapy for patients that refuse an indwelling catheter.

13 Claims, 15 Drawing Sheets

(56) References Cited

U.S. PATENT DOCUMENTS

| | | | |
|---|---|---|---|
| 4,146,029 | A | 3/1979 | Ellinwood, Jr. |
| 4,204,957 | A | 5/1980 | Weickhardt |
| 4,216,462 | A | 8/1980 | McGrath et al. |
| 4,229,299 | A | 10/1980 | Savitz et al. |
| 4,261,360 | A | 4/1981 | Perez |
| 4,275,726 | A | 6/1981 | Schael |
| 4,291,692 | A | 9/1981 | Bowman et al. |
| 4,343,316 | A | 8/1982 | Jespersen |
| 4,411,649 | A | 10/1983 | Kamen |
| 4,448,207 | A | 5/1984 | Parrish |
| 4,449,538 | A | 5/1984 | Corbitt et al. |
| 4,504,263 | A | 3/1985 | Steuer et al. |
| 4,658,834 | A | 4/1987 | Blankenship et al. |
| 4,712,567 | A | 12/1987 | Gille et al. |
| 4,728,333 | A | 3/1988 | Masse et al. |
| 4,728,433 | A | 3/1988 | Buck et al. |
| 4,813,925 | A | 3/1989 | Anderson, Jr. et al. |
| 4,923,598 | A | 5/1990 | Schal |
| 4,994,026 | A | 2/1991 | Fecondini |
| 5,038,109 | A | 8/1991 | Goble |
| 5,098,379 | A | 3/1992 | Conway et al. |
| 5,176,148 | A | 1/1993 | Wiest et al. |
| 5,179,862 | A | 1/1993 | Lynnworth |
| 5,207,642 | A | 5/1993 | Orkin et al. |
| 5,573,506 | A | 11/1996 | Vasko |
| 5,586,973 | A | 12/1996 | Lemaire et al. |
| 5,709,670 | A | 1/1998 | Vancaillie et al. |
| 5,722,947 | A | 3/1998 | Jeppsson et al. |
| 5,769,087 | A | 6/1998 | Westphal et al. |
| 5,814,009 | A | 9/1998 | Wheatman |
| 5,891,051 | A | 4/1999 | Han et al. |
| 5,910,252 | A | 6/1999 | Truitt et al. |
| 5,916,153 | A | 6/1999 | Rhea, Jr. |
| 5,916,195 | A | 6/1999 | Eshel et al. |
| 5,981,051 | A | 11/1999 | Motegi et al. |
| 5,984,893 | A | 11/1999 | Ward |
| 6,010,454 | A | 1/2000 | Arieff et al. |
| 6,171,253 | B1 | 1/2001 | Bullister et al. |
| 6,231,551 | B1 | 5/2001 | Barbut |
| 6,272,930 | B1 | 8/2001 | Crozafon |
| 6,514,226 | B1 | 2/2003 | Levin et al. |
| 6,531,551 | B2 | 3/2003 | Ohno et al. |
| 6,537,244 | B2 | 3/2003 | Paukovits et al. |
| 6,554,791 | B1 | 4/2003 | Cartledge et al. |
| 6,640,649 | B1 | 11/2003 | Paz et al. |
| 6,740,072 | B2 | 5/2004 | Starkweather et al. |
| 6,752,779 | B2 | 6/2004 | Paukovits et al. |
| 6,796,960 | B2 | 9/2004 | Cioanta et al. |
| 6,827,702 | B2 | 12/2004 | Lebel et al. |
| 6,942,637 | B2 | 9/2005 | Cartledge et al. |
| 7,029,456 | B2 | 4/2006 | Ware et al. |
| 7,044,002 | B2 | 5/2006 | Ericson et al. |
| 7,086,615 | B2 | 8/2006 | Joseph |
| 7,137,964 | B2 | 11/2006 | Flaherty |
| 7,278,983 | B2 | 10/2007 | Ireland et al. |
| 7,727,222 | B2 | 6/2010 | Da Silva |
| 7,736,354 | B2 | 6/2010 | Gelfand |
| 7,739,921 | B1 | 6/2010 | Babcock |
| 7,758,562 | B2 | 7/2010 | Gelfand |
| 7,758,563 | B2 | 7/2010 | Gelfand |
| 7,837,667 | B2 | 11/2010 | Gelfand |
| 7,938,817 | B2 | 5/2011 | Gelfand |
| 8,007,460 | B2 | 8/2011 | Gelfand |
| 8,075,513 | B2 | 12/2011 | Rudko et al. |
| 8,233,957 | B2 | 7/2012 | Merz et al. |
| 8,444,623 | B2 | 5/2013 | Gelfand |
| 8,556,846 | B2 | 10/2013 | O'Mahony et al. |
| 8,714,030 | B1 | 5/2014 | Liu |
| 9,526,833 | B2 | 12/2016 | Gelfand et al. |
| 10,045,734 | B2 | 8/2018 | Da Silva |
| 10,537,281 | B2 | 1/2020 | Thompson et al. |
| 10,639,419 | B2 | 5/2020 | Halpert |
| 10,881,774 | B2 | 1/2021 | Halpert |
| 11,064,939 | B2 | 7/2021 | Da Silva |
| 11,213,621 | B2 | 1/2022 | Halpert |
| 11,357,446 | B2 | 6/2022 | Levin et al. |
| 11,633,137 | B2 | 4/2023 | Conley et al. |
| 11,696,985 | B2 | 7/2023 | Halpert |
| 11,950,925 | B2 | 4/2024 | Levin |
| 11,986,302 | B2 | 5/2024 | Conley et al. |
| 11,992,332 | B2 | 5/2024 | Da Silva |
| 2001/0029340 | A1 | 10/2001 | Mault et al. |
| 2002/0025597 | A1 | 2/2002 | Matsuda |
| 2002/0072647 | A1 | 6/2002 | Schock et al. |
| 2002/0107536 | A1 | 8/2002 | Hussein |
| 2002/0151834 | A1 | 10/2002 | Utterberg |
| 2002/0161314 | A1 | 10/2002 | Sarajarvi |
| 2003/0040700 | A1 | 2/2003 | Hickle |
| 2003/0048185 | A1 | 3/2003 | Citrenbaum et al. |
| 2003/0048432 | A1 | 3/2003 | Jeng et al. |
| 2003/0114786 | A1 | 6/2003 | Hiller et al. |
| 2004/0025597 | A1 | 2/2004 | Ericson et al. |
| 2004/0059295 | A1 | 3/2004 | Cartledge et al. |
| 2004/0081585 | A1 | 4/2004 | Reid |
| 2004/0087894 | A1 | 5/2004 | Flaherty |
| 2004/0122353 | A1 | 6/2004 | Shahmirian et al. |
| 2004/0133187 | A1 | 7/2004 | Hickle |
| 2004/0163655 | A1 | 8/2004 | Gelfand et al. |
| 2004/0167415 | A1 | 8/2004 | Gelfand |
| 2004/0167464 | A1 | 8/2004 | Ireland et al. |
| 2004/0176703 | A1 | 9/2004 | Christensen et al. |
| 2004/0193328 | A1 | 9/2004 | Zaitsu et al. |
| 2004/0243075 | A1 | 12/2004 | Harvie |
| 2005/0027254 | A1 | 2/2005 | Vasko |
| 2005/0065464 | A1 | 3/2005 | Talbot et al. |
| 2005/0085760 | A1 | 4/2005 | Ware et al. |
| 2006/0052764 | A1 | 3/2006 | Gelfand et al. |
| 2006/0064053 | A1 | 3/2006 | Bollish et al. |
| 2006/0100743 | A1 | 5/2006 | Townsend et al. |
| 2006/0184084 | A1 | 8/2006 | Ware et al. |
| 2006/0235353 | A1 | 10/2006 | Gelfand et al. |
| 2006/0253064 | A1 | 11/2006 | Gelfand et al. |
| 2006/0270971 | A1 | 11/2006 | Gelfand et al. |
| 2007/0055198 | A1 | 3/2007 | O'Mahony et al. |
| 2007/0088333 | A1 | 4/2007 | Levin et al. |
| 2008/0027409 | A1 | 1/2008 | Rudko et al. |
| 2008/0033394 | A1 | 2/2008 | Gelfand et al. |
| 2008/0051764 | A1 | 2/2008 | Dent et al. |
| 2008/0171966 | A1 | 7/2008 | Rudko et al. |
| 2008/0221512 | A1 | 9/2008 | Da Silva et al. |
| 2009/0054745 | A1 | 2/2009 | Jennewine |
| 2009/0062730 | A1* | 3/2009 | Woo .................. A61M 5/1723 |
| | | | 604/66 |
| 2010/0133510 | A1 | 6/2010 | Kim et al. |
| 2010/0185175 | A1 | 7/2010 | Kamen |
| 2010/0280443 | A1 | 11/2010 | Gelfand et al. |
| 2010/0280444 | A1 | 11/2010 | Gelfand et al. |
| 2010/0286559 | A1 | 11/2010 | Paz et al. |
| 2010/0312039 | A1 | 12/2010 | Quirico |
| 2011/0046514 | A1 | 2/2011 | Greenwald et al. |
| 2011/0046516 | A1 | 2/2011 | Paz et al. |
| 2011/0120231 | A1 | 5/2011 | Berger |
| 2011/0196304 | A1 | 8/2011 | Kramer et al. |
| 2011/0218411 | A1 | 9/2011 | Keenan |
| 2011/0288524 | A1 | 11/2011 | Gelfand et al. |
| 2012/0078137 | A1 | 3/2012 | Mendels |
| 2012/0259308 | A1 | 10/2012 | Gelfand |
| 2013/0104667 | A1 | 5/2013 | Koyano |
| 2013/0235691 | A1 | 9/2013 | Volker |
| 2013/0261412 | A1 | 10/2013 | Reed |
| 2013/0274705 | A1 | 10/2013 | Burnes et al. |
| 2014/0031787 | A1 | 1/2014 | Burnes et al. |
| 2014/0073973 | A1 | 3/2014 | Sexton |
| 2014/0228755 | A1 | 8/2014 | Darrah et al. |
| 2014/0260600 | A1 | 9/2014 | Rike |
| 2014/0366641 | A1 | 12/2014 | Jedema et al. |
| 2015/0105694 | A1 | 4/2015 | Mahajan |
| 2015/0204860 | A1 | 7/2015 | Chui |
| 2015/0233749 | A1 | 8/2015 | Wang et al. |
| 2015/0258277 | A1 | 9/2015 | Halpert |
| 2016/0051176 | A1 | 2/2016 | Ramos et al. |
| 2016/0051750 | A1 | 2/2016 | Tsoukalis |
| 2016/0136356 | A1 | 5/2016 | Ribble et al. |
| 2017/0016755 | A1 | 1/2017 | Boussange et al. |

(56) References Cited

U.S. PATENT DOCUMENTS

| | | |
|---|---|---|
| 2017/0052056 A1 | 2/2017 | Yamasaki et al. |
| 2017/0290974 A1 | 10/2017 | Tsoukalis |
| 2018/0071455 A9 | 3/2018 | Halpert |
| 2018/0110455 A1 | 4/2018 | Chang et al. |
| 2018/0177945 A1 | 6/2018 | Sims et al. |
| 2018/0245967 A1 | 8/2018 | Parker et al. |
| 2018/0250461 A1 | 9/2018 | Gura |
| 2018/0280620 A1 | 10/2018 | Reichthalhammer |
| 2019/0001057 A1 | 1/2019 | Tsoukalis |
| 2019/0038833 A1 | 2/2019 | Pirazzoli et al. |
| 2019/0262532 A1 | 8/2019 | Oh et al. |
| 2019/0321588 A1 | 10/2019 | Burnett |
| 2020/0230351 A1 | 7/2020 | Kelly et al. |
| 2020/0284234 A1 | 9/2020 | Huberts et al. |
| 2020/0324044 A1 | 10/2020 | Gylland et al. |
| 2020/0360604 A1 | 11/2020 | Kolko et al. |
| 2020/0405955 A1 | 12/2020 | Shah et al. |
| 2021/0024536 A1 | 1/2021 | Bhattacharya |
| 2021/0077007 A1 | 3/2021 | Jouret et al. |
| 2021/0085853 A1 | 3/2021 | Chen et al. |
| 2021/0128815 A1 | 5/2021 | Byrne et al. |
| 2021/0162188 A1 | 6/2021 | Cui |
| 2021/0169408 A1 | 6/2021 | Levin et al. |
| 2021/0170084 A1 | 6/2021 | Zacharia |
| 2021/0196880 A1 | 7/2021 | O'Mahony et al. |
| 2021/0236727 A1 | 8/2021 | Levin et al. |
| 2021/0244381 A1 | 8/2021 | Sweeney et al. |
| 2021/0260306 A1 | 8/2021 | Gravenstein et al. |
| 2021/0283357 A1 | 9/2021 | Leonard |
| 2021/0298653 A1 | 9/2021 | Woodward et al. |
| 2021/0369959 A1 | 12/2021 | Abal et al. |
| 2022/0152302 A1 | 5/2022 | Halpert |
| 2022/0273213 A1 | 9/2022 | Sokolov |
| 2022/0288362 A1 | 9/2022 | Porter et al. |
| 2022/0296140 A1* | 9/2022 | Nguyen ................. A61B 5/208 |
| 2022/0296406 A1 | 9/2022 | Keelen |
| 2022/0313158 A1 | 10/2022 | Levin et al. |
| 2022/0330866 A1 | 10/2022 | Conley et al. |
| 2022/0330867 A1 | 10/2022 | Conley et al. |
| 2022/0339622 A1 | 10/2022 | Halpert |
| 2023/0010793 A1 | 1/2023 | Testani |
| 2023/0068431 A1 | 3/2023 | Erbey, II et al. |
| 2023/0414871 A1 | 12/2023 | Halpert et al. |
| 2024/0260874 A1 | 8/2024 | Halpert et al. |
| 2024/0285209 A1 | 8/2024 | Conley et al. |
| 2024/0347162 A1* | 10/2024 | Meese ................. A61M 5/1407 |

FOREIGN PATENT DOCUMENTS

| | | |
|---|---|---|
| EP | 3278833 | 2/2018 |
| EP | 4108171 | 12/2022 |
| GB | 2560580 | 9/2018 |
| JP | 2008110150 | 5/2008 |
| JP | 2010503515 | 2/2010 |
| JP | A-2011-520549 | 7/2011 |
| JP | A-2017-536857 | 2/2017 |
| KR | 10-2022-0035738 | 3/2022 |
| WO | WO-1996016685 | 6/1996 |
| WO | WO-1996028209 | 9/1996 |
| WO | WO-1997016220 | 5/1997 |
| WO | WO-1999006087 | 2/1999 |
| WO | WO-2005102441 | 11/2005 |
| WO | WO-2006041496 | 4/2006 |
| WO | WO-2009029899 | 3/2009 |
| WO | WO-2013154783 | 10/2013 |
| WO | WO-2014022422 | 2/2014 |
| WO | WO-2015142617 | 9/2015 |
| WO | WO-2016103256 | 6/2016 |
| WO | 2018044959 | 3/2018 |
| WO | WO-2018114794 | 6/2018 |
| WO | WO-2019222485 | 11/2019 |
| WO | WO-2020033752 | 2/2020 |
| WO | WO-2021205345 | 10/2021 |
| WO | WO-2022219578 | 10/2022 |
| WO | 2022259115 | 12/2022 |
| WO | 2024013731 | 1/2024 |

OTHER PUBLICATIONS

Phillips et al., "Measurement of sodium ion concentration in undiluted urine with cation-selective polymeric membrane electrodes after the removal of interfering compounds", Talanta, Elsevier, Amsterdam, NL, vol. 74, No. 2, Nov. 15, 2007, pp. 255-264.

International Search Report and Written Opinion for International Patent Application No. PCT/US2025/016137, Applicant: Reprieve Cardiovascular, Inc., mailed May 29, 2025, 11 pages.

U.S. Appl. No. 16/544,975, filed Aug. 20, 2019, Levin.

U.S. Appl. No. 18/595,182, filed Mar. 4, 2024, Levin.

U.S. Appl. No. 18/641,241, filed Apr. 19, 2024, Da Silva.

Adaptec Medical Devices, "Ongoing Access to Real-Time and Accurate Monitoring of Urine Output Could Improve Management of Critically Ill Patients," Clinical Literature Review, (2016) 8 pages.

Allen et al., "Continuous Versus Bolus Dosing of Furosemide for Patients Hospitalized for Heart Failure," American Journal of Cardiology, 105(12):1794-1794, 2010.

Baliga, "Diuretic Therapy for Heart Failure Patients," American College of Cardiology, 75:1178-1195, 2020.

Bart et al., "Ultrafiltration in Decompensated Heart Failure With Cardiorenal Syndrome", The New England Journal of Medicine, Dec. 13, 2012, 9 pages, Massachusetts Medical Society.

Bell et al., "Risk of Postoperative Acute Kidney Injury in Patients Undergoing Orthopaedic Surgery—Development and Validation of Risk score and Effect of Acute Kidney Injury on Survival: Observational Cohort Study," BMJ: 2015, 9 pages.

Bouman et al., "Red Blood Cell Transfusion and Furosemide in Cardiac Surgery: Friend and Foe?" The Netherlands Journal of Medicine, Dec. 2012, vol. 70, No. 10, 3 pages.

Brater, "Diuretic Therapy," New England Journal of Medicine, 339:387-395, 1998.

Brezis et al., Hypoxia of the Renal Medulla—Its Implications for Disease, New England Journal of Medicine, vol. 322, No. 10, Mar. 9, 1995, 9 pages.

Briguori et al., "Renal Insufficiency After Contrast Media Administration Trial II (Remedial II): RenalGuard System in High-Risk Patients for Contrast-Induced Acute Kidney Injury", Circulation, Journal of the American Heart Association, Mar. 13, 2011, 10 pages.

Conradds, "Sensitivity And Positive Predictive Value of Implantable Intrathoracic Impedance Monitoring as a Predictor of Heart Failure Hospitalizations: The SENSE-HF Trial," European Heart Journal (2011) 32, 2266-2273, 8pages.

Cosgrove III et al., "Automated Control Postoperative Hypertension: A Prospective Randomized Multicenter Study," 1989 by The Society of Thoracic Surgeons, 6 pages.

Dorval et al., "Feasibility Study of the RenalGuard™ Balanced Hydration System: A Novel Strategy for the Prevention of Contrast-Induced Nephropathy in High Risk Patients", International Journal of Cardiology, 2011, 5 pages, Elsevier Ireland Ltd.

Doty et al., Effect of Increased Renal Venous Pressure on Renal Function, The Journal of Trauma: Injury, Infection and Critical Care, vol. 47, No. 6, Dec. 1999, 4 pages.

Edelson et al., Pharmacokinetics of Iohexol, a New Nonionic Radiocontrast Agent, in Humans, Journal of Pharmaceutical Sciences, vol. 73, No. 7, Jul. 1984, 3 pages.

Ellison et al., "Diuretic Treatment in Heart Failure," New England Journal of Medicine, 377:1964-1975, 2017.

Farcy, "Review: Pitfalls in Using Central Venous Pressure as a Marker of Fluid Responsiveness," Emergency Medicine. Jan. 2016;48(1):18-28, 15 pages.

Farkas, "Deresuscitation: Dominating the Diuresis," The Internet Book of Critical Care, 43 pages, 2020.

Felker et al., "Diuretic Strategies in Patients With Acute Decompensated Heart Failure", The New England Journal of Medicine, Mar. 3, 2011, vol. 364, No. 9, 9 pages.

(56) References Cited

OTHER PUBLICATIONS

Furutani et al., "An Automatic Control System of the Blood Pressure of Patients Under Surgical Operation," International Journal of Control, Automation, and Systems, vol. 2, No. 1, Mar. 2004, pp. 39-54.

Gheorghiade et al., "Current Medical Therapy for Advanced Heart Failure," American Heart Journal, Jun. 1998, pp. S231-S248.

Gloor, James M. and Vincente E. Torres, Reflux and Obstructive Nephropathy, Atlas of Diseases of the Kidney, on-line edition, vol. Two, Section I, Ch. 8, pp. 8.1-8.25, 1999, 27 pages.

Goren et al., "Perioperative Acute Kidney Injury," British Journal of Anaesthesia, 2015, 12 pages.

Hasselblad et al., "Relation Between Dose of Loop Diuretics and Outcomes in a Heart Failure Population: Results of the ESCAPE Trial", European Journal of Heart Failure, 9(10):1064-1069, 2007.

Heyman et al., Pathophysiology of Radiocontrast Nephropathy: A Role for Medullary Hypoxia, Investigative Radiology, vol. 34, No. 11, Nov. 1999, 7 pages.

Hvistendahl et al., Renal Hemodynamic Response to Gradated Ureter Obstruction in the Pig, Nephron 1996, 74:168-74, 7 pages.

Jin et al., "Intensive Monitoring of Urine Output Is Associated With Increased Detection of Acute Kidney Injury and Improved Outcomes," Chest Journal—Original Research Critical Care, 152#5, pp. 972-979 (Nov. 2017) 8 pages.

Josephs et al., "Perioperative Risk Assessment, Prevention, and Treatment of Acute Kidney Injury," International Anesthesiology Clinics, vol. 47, No. 4, www.anesthesiaclinics.com, pp. 89-105.

Kalantari, "Assessment of Intravascular Volume Status and Volume Responsiveness in Critically Ill Patients," Kidney International (2013) 83, 1017-1028 (Jan. 9, 2013) 12 pages.

Kolh, "Renal Insufficiency After Cardiac Surgery: A Challenging Clinical Problem," European Heart Journal, 2009, pp. 1824-1827.

Lara, "Accurate Monitoring of Intravascular Fluid Volume: A Novel Application of Intrathoracic Impedance Measures for the Guidance of Volume Reduction Therapy," IJC Heart & Vasculature, 8 (2015) pp. 47-51, 5pages.

Lassnigg et al., "Lack of Renoprotective Effects of Dopamine and Furosemide During Cardiac Surgery," J. Am Soc Nephrol, 2000, pp. 97-104.

Lelarge et al., Acute Unilateral Renal Failure and Contralateral Ureteral Obstruction, American Journal of Kidney Diseases, vol. XX, No. 3, Sep. 1992, 3 pages.

Lenihan et al., "Trends in Acute Kidney Injury, Associated Use of Dialysis and Mortality After Cardiac Surgery, 1999 to 2008," Ann Thorac Surg. 2013, 17 pages.

Levin et al. High-volume diuresis with matched maintenance of intravascular volume may prevent contrast-induced nephropathy in post-transplant patients with moderate-severe baseline renal impairment, Cardiovascular Revascularization Medicine, Elsevier, NL, vol. 8, No. 2, Apr. 1, 2007, 1 page.

Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, 161 pages.

Magder et al., "The Clinical Role of Central Venous Pressure Measurements", Journal of Intensive Care Medicine 22(1); 207, 8 pages.

Marenzi et al., "Prevention of Contrast Nephropathy by Furosemide With Matched Hydration," JACC: Cardiovascular Interventions, 5(1):90-97, 2011.

Marenzi et al., "Prevention of Contrast Nephropathy by Furosemide With matched Hydration. The MYTHOS (Induced Diuresis With Matched Hydration Compared to Standard Hydration for Contrast Induced Nephropathy Prevention) Trial", JACC: Cardiovascular Interventions, vol. 5, No. 1, 2012 The American College of Cardiology Foundation, 8 pages.

Mawer et al., "Value of Forced Diuresis in Acute Barbiturate Poisoning", Jun. 29, 1968, British Medical Journal, 2, 4 pages.

Mayo Clinic, "Creatinine Test", Mayo Foundation for Medical Education and Research (MFMER) (downloaded Aug. 16, 2018).

Meersch et al., "Perioperative Acute Kidney Injury: An Under-Recognized Problem," vol. 125, No. 4, www.anesthesia-analgesia.org, Oct. 2017, pp. 1223-1232.

Mendeley et al., "Furosemide", Science Direct, 5 pages, 2016.

Oh et al., "Loop Diuretics in Clinical Practice," Review: Electrolyte Blood Press, 13(1): 5 pages, 2015.

Oh et al., "Loop Diuretics In Clinical Practice", Electrolytes & Blood Pressure, www.ncbi.nlm.nih.gov/pmc/articles/PMC4520883, printed Mar. 25, 2019, 6 pages.

Olivero et al., "Acute Kidney Injury After Cardiovascular Surgery: An Overview," debakeyheartcenter.com/journal, 2012, pp. 31-36.

Otero, "A New Device to Automate the Monitoring of Critical Patients' Urine Output", Hindawi Publishing Corp, BioMed Research Int'l, vol. 2014, Article ID 587593, 8 pages.

Palazzuli et al. "Continuous versus bolus intermittent loop diuretic infusion in acutely decompensated heart failure: a prospective randomized trial," Critical Care 18, 2014.

Paterna et al., "Changes in Brain Natriuretic Peptide Levels and Bioelectrical Impedance Measurements After Treatment With High-Dose Furosemide and Hypertonic Saline Solution Versus High-Dose Furosemide Alone in Refractory Congestive Heart Failure", Journal of the American College of Cardiology, 2005, vol. 45, No. 12, 7 pages.

Pederson et al., Renal Water and Sodium Handling During Gradated Unilateral Ureter Obstruction, Scand J. Urol Nephrol, 2002, 36:163-72, 11 pages.

Prandota et al., "Pharmacokinetics and metabolism of furosemide in man," European Journal of Drug Metabolism and Pharmcokinetics, 1(4): 5 pages, 1976.

Rihal et al., Incidence and Prognostic Importance of Acute Renal Failure After Percutaneous Coronary Intervention, Circulation, May 14, 2002, 6 pages.

Rosamilia et al., Electromotive Drug Administration of Lidocaine and Dexamethasone Followed by Cystodistension in Women with Interstitial Cystitis, International Urogyecologyl Journal, Pelvic Floor Dysfunction 1997; 8: 142-5, 4 pages.

Rui Geng et al., "Identification of Modifiable Risk Factors for Acute Kidney Injury After Coronary Artery Bypass Graft Surgery in an Asian Population," The Journal of Thoracic and Cardiovascular Surgery, Apr. 2014, pp. 1356-1361.

S215 Ultra Low Profile Single Point Load Cell-Strain Guage Sensors and Load Cells, Ultra-Low Profile Single Point Load Cell-S215, http://smdsensors.com/detail_pgs/s215.htm 2005, 3 pages.

Shepherd, "Measuring and Managing Fluid Balance", Nursing Times, vol. 107, No. 28, pp. 12-16 (Jul. 19, 2011) 5 pages.

Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21, 5 pages.

Stevens, Melissa A., MD et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb. 1999, 9 pages.

Stevenson et al., "Editorial Comment, Torrent or Torment From the Tubules?", Challenge of the Cardiorenal Connections, Journal of the American College of Cardiology, vol. 45, No. 12, 2005, 4 pages.

Stickler et al., "A Sensor to Detect the Early Stages in the Development of Crystalline Proteus mirabilis Biofilm on Indwelling Bladder Catheters", Journal of Clinical Microbiology, Apr. 2006, p. 1540-1542.

Teixeira et al., "Fluid Balance and Urine Volume are Independent Predictors of Mortality in Acute Kidney Injury", Critical Care 17:R14 (2013) 11 pages.

Testani et al., "Rapid and Highly Accurate Prediction of Poor Loop Diuretic Natriuretic Response in Patients with Heart Failure," Circulation; Heart Failure, vol. 9. No. 1, 2016, 32 pages.

Thakar, "Perioperative Acute Kidney Injury," Advances in Chronic Kidney Disease, vol. 20, No. 1, 2013, pp. 67-75.

Tricoli, "Miniaturized Bio-and Chemical-Sensors for Point-of-Care Monitoring of Chronic Kidney Diseases," Sensors 2018, 18, 942; (Mar. 22, 2018) 18 pages.

Unknown Author, "Furosemide Drug Summary," Prescriber's Digital Reference, pp. 1-31, 2016.

(56) References Cited

OTHER PUBLICATIONS

Vellinga et al., "Identification of Modifiable Risk Factors for Acute Kidney Injury After Cardiac Surgery," The Netherlands Journal of Medicine, vol. 70, No. 10, Dec. 2012, pp. 450-454.

Wakelkamp et al., The influence of drug input rate on the development of tolerance to frusemide, Br. J. Clin. Pharmacol 1998, 46:479-487, 9 pages.

Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415, pages.

Yeh et al., "Goal-directed diuresis: A case—control study of continuous furosemide infusion in critically ill trauma patients", The Journal of Emergencies, Trauma, and Shock, 8(1): 34-38, 2015.

Written Opinion of the International Searching Authority for PCT Application No. PCT/US2005/008948 dated Oct. 3, 2006, 3 pages.

Written Opinion of the International Searching Authority for PCT Application No. PCT/US2007/021791 dated May 8, 2008, 7 pages.

Written Opinion of the International Searching Authority for PCT Application No. PCT/U20S07/009685 dated Jul. 18, 2008, 10 pages.

Written Opinion of the International Searching Authority for PCT Application No. PCT/US2007/009684 dated Jul. 21, 2008, 7 pages.

Written Opinion of the International Searching Authority for PCT Application No. PCT/US2008/007845 dated Sep. 17, 2008, 5 pages.

Written Opinion of the International Searching Authority for PCT Application No. PCT/US2008/007841 dated Sep. 18, 2008 4 pages.

Written Opinion of the International Searching Authority for PCT Application No. PCT/US2007/009683 dated Nov. 24, 2008, 6 pages.

Written Opinion of the International Searching Authority for PCT Application No. PCT/US2009/002739 dated Jun. 19, 2009, 4 pages.

Written Opinion of the International Searching Authority for PCT Application No. PCT/US2010/000137 dated Mar. 16, 2010, 8 pages.

Written Opinion of the International Searching Authority for PCT Application No. PCT/US2015/020196, dated Jun. 12, 2015, 5 pages.

"2016 ESC Guidelines for the Diagnosis and Treatment of Acute and Chronic Heart Failure—Web Addenda," European Heart Journal, 17 pages.

Adams et al., "Executive Summary: HFSA 2006 Comprehensive Heart Failure Practice Guideline," Journal of Cardiac Failure, vol. 12, No. 1, 2006, pp. 10-38.

Rosenberg et al., "Combination Therapy with Metolazone and Loop Diurectics in Outpatients with Refactory Heart Failure: An Observational Study and Review of the Literature," Cardiovascular Drugs and Therapy, Kluwer Academic Publishers, vol. 19, No. 4, Aug. 2005, 6 pages.

* cited by examiner

200

202
Obtaining a urine output rate from a patient

204
Causing a diuretic to be provided to the patient at a dosage rate

206
Causing a hydration fluid to be provided to the patient at a hydration rate

208
Adjusting at least one of the dosage rate of the diuretic or the hydration rate of the hydration fluid, thereby causing net fluid loss from the patient

300

302
Obtaining urine output data from a patient without using an indwelling catheter 304
Does the urine output data equal or exceed a urine output threshold?

No

Yes

306
Prompting a user to transition the patient to an indwelling catheter

308
Changing fluid therapy system to an indwelling catheter mode

Figure 3B:
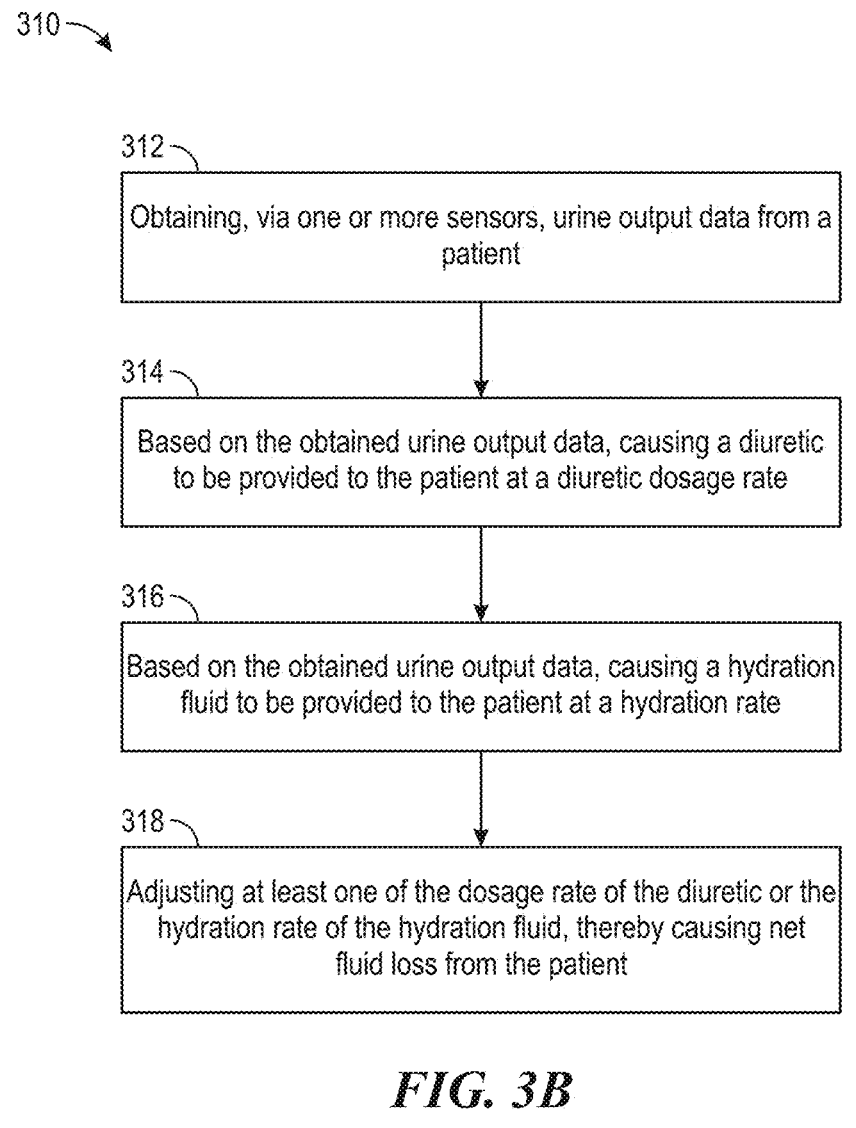

310 ⤸

312 ⌐

Obtaining, via one or more sensors, urine output data from a patient

314 ⌐

Based on the obtained urine output data, causing a diuretic to be provided to the patient at a diuretic dosage rate

316 ⌐

Based on the obtained urine output data, causing a hydration fluid to be provided to the patient at a hydration rate

318 ⌐

Adjusting at least one of the dosage rate of the diuretic or the hydration rate of the hydration fluid, thereby causing net fluid loss from the patient

Instructing patient to void bladder

604

Obtaining a urine output of a patient
over a predetermined previous time period

606

Is
the urine output over the
predetermined previous time period
less than a predetermined urine
output threshold?

No

Yes

608

Recommending an increase to a dosage
rate of a diuretic administered to the patient

630

632

Instructing patient to void bladder

634

Receiving confirmation that
the patient has voided their bladder

636

Causing a diuretic to
be administered to the patient

638

Waiting a predetermined amount of time

640

Obtaining a urine output from the patient

642

Adjusting the administration of the diuretic
based, at least in part, on the urine output volume

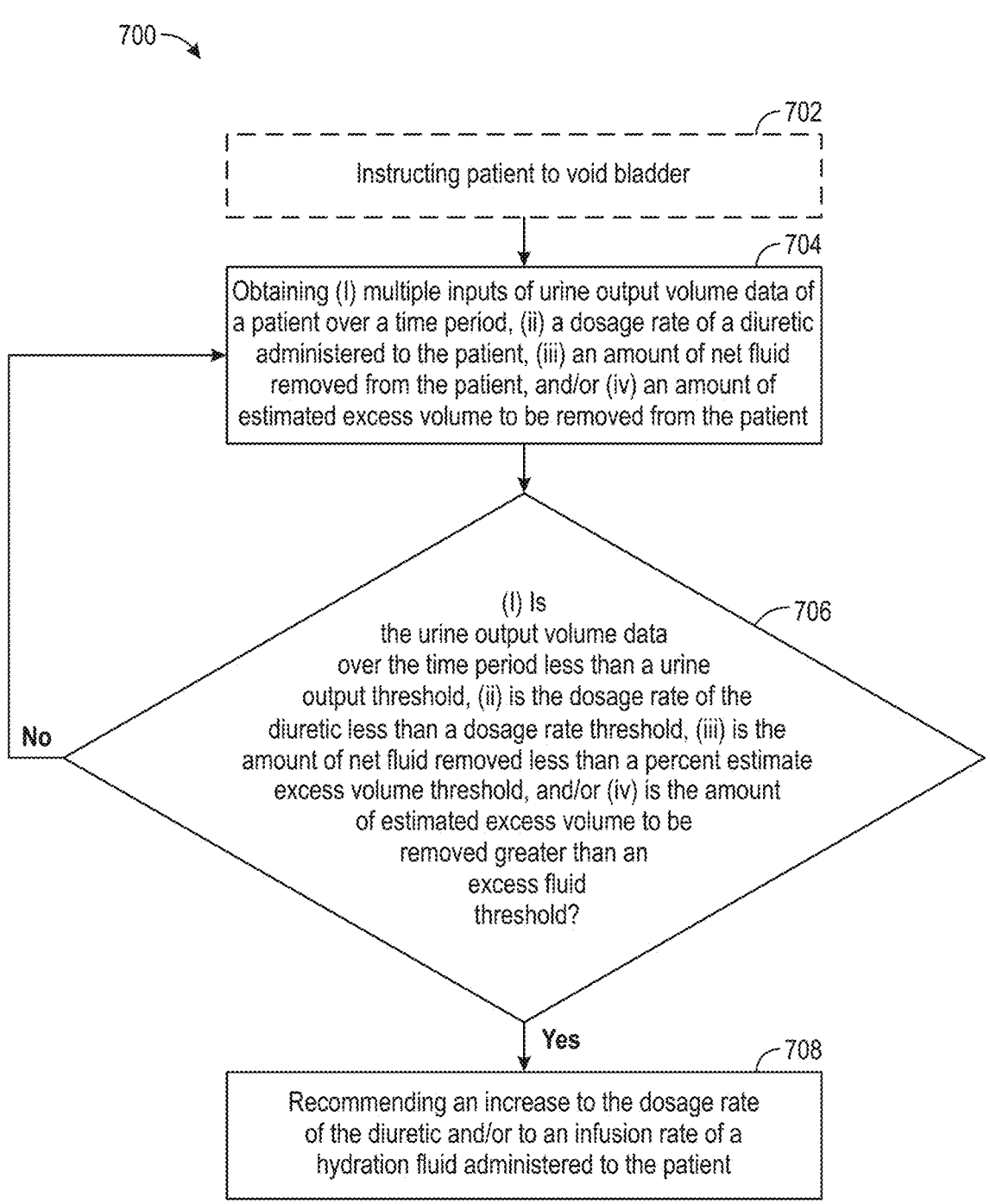

700 —

702

Instructing patient to void bladder

704

Obtaining (I) multiple inputs of urine output volume data of a patient over a time period, (ii) a dosage rate of a diuretic administered to the patient, (iii) an amount of net fluid removed from the patient, and/or (iv) an amount of estimated excess volume to be removed from the patient

706

(I) Is the urine output volume data over the time period less than a urine output threshold, (ii) is the dosage rate of the diuretic less than a dosage rate threshold, (iii) is the amount of net fluid removed less than a percent estimate excess volume threshold, and/or (iv) is the amount of estimated excess volume to be removed greater than an excess fluid threshold?

No

Yes

708

Recommending an increase to the dosage rate of the diuretic and/or to an infusion rate of a hydration fluid administered to the patient

*FIG. 7*

URINE OUTPUT SENSING WITHOUT USE OF AN INDWELLING CATHETER, AND ASSOCIATED SYSTEMS, DEVICES, AND METHODS

CROSS-REFERENCE TO RELATED APPLICATION

The present application claims priority to U.S. Provisional App. No. 63/554,744; filed Feb. 16, 2024; and titled "URINE OUTPUT SENSING WITHOUT USE OF AN INDWELLING CATHETER, AND ASSOCIATED SYSTEMS, DEVICES, AND METHODS"; and is related to U.S. Pat. No. 11,357,446; filed Dec. 4, 2020; and titled "MANAGING FLUID LEVELS IN A PATIENT AND ASSOCIATED DEVICES, SYSTEMS, AND METHODS;" both of which are incorporated herein by reference in their entireties.

TECHNICAL FIELD

The present disclosure generally relates to medical devices and, in particular, to urine output sensing without the use of an indwelling catheter, and associated systems, devices, and methods.

BACKGROUND

Human physiological systems seek to naturally maintain a balance between fluid intake and fluid excretion. An imbalance in fluid intake and excretion rates may cause the body to retain excess amounts of fluid, also known as fluid overload. Fluid overload can be caused by acute decompensated heart failure (ADHF), chronic heart failure (CHF), or other conditions in which insufficient fluid is excreted. Patients exhibiting fluid overload may suffer from shortness of breath (dyspnea), edema, hypertension, and other undesirable medical conditions.

To treat fluid overload, patients are typically administered a diuretic drug which induces and/or increases urine production, thus reducing the amount of fluid and sodium in the body. The rate of urine output may be carefully monitored and/or controlled for safety reasons, e.g., to avoid placing undue stress on the patient's kidneys. Different patients may respond differently to treatment, such that the same diuretic type and/or dosage may produce drastically different urine output rates. However, conventional systems and methods for treating fluid overload may not be capable of accurately monitoring a patient's urine output and/or responding to changes in urine output. Additionally, conventional treatment systems and devices may not be capable of accommodating high urine production rates, and thus may require a nurse or other healthcare professional to empty and/or replace urine collection bags multiple times during the treatment procedure. Conventional systems and devices may also be prone to air lock and/or interruptions to urine flow.

BRIEF DESCRIPTION OF THE DRAWINGS

Features, aspects, and advantages of the presently disclosed technology may be better understood with regard to the following drawings.

FIGS. 3A and 3B are block diagrams illustrating methods for treating a patient, in accordance with embodiments of the present technology.

FIG. 7 is a block diagram illustrating a method associated with escalating a patient's fluid therapy, in accordance with embodiments of the present technology.

Figure 1:
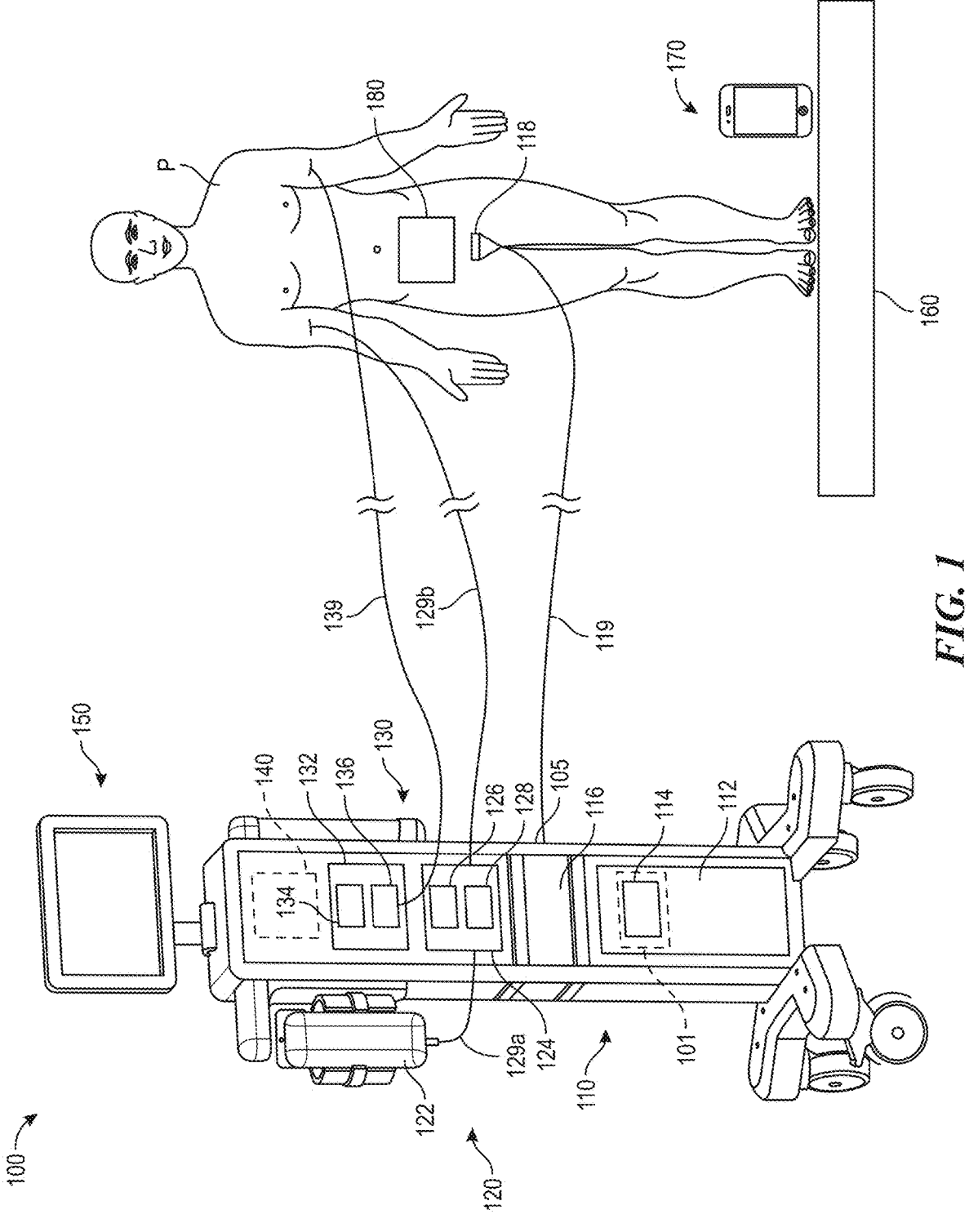
FIG. 1 is a partially schematic view of a fluid management system configured in accordance with embodiments of the present technology.

A person skilled in the relevant art will understand that the features shown in the drawings are for purposes of illustrations, and variations, including different and/or additional features and arrangements thereof, are possible.

DETAILED DESCRIPTION

I. Overview

The present technology is directed to systems for managing (e.g., increasing or decreasing) a patient's urine output based at least in part on an estimated excess fluid volume of the patient. Embodiments of the present technology relate to infusing diuretic and/or hydration fluid to increase or optimize urine output, net fluid removal, and/or net sodium removal from the patient. Before a patient begins receiving fluid therapy, it is difficult, if not impossible, to predict how the patient will respond to the fluid therapy and/or whether the fluid therapy will be effective to increase or optimize the patient's urine output, net fluid removal, and/or net sodium removal. While a standard treatment protocol may be effective for some patients, many, if not most, patients can have unique conditions and/or have abnormal responses to the standard treatment protocols that prevent or inhibit optimal therapy. As an example, certain patients may not react to some diuretics and/or may have underlying conditions (e.g., low or high blood pressure) which limit their urine output rates, net fluid removal, and/or net sodium removal, or make treatment to achieve maximum urine output rates, net fluid removal, and/or net sodium removal more difficult. For such patients, additional steps or protocols may be necessary to increase urine output, net fluid removal, and/or net sodium removal and relieve fluid overload conditions. These additional steps or protocols can be based on data associated with a patient receiving therapy, such as the patient's response to the received therapy (e.g., the administered diuretic and/or hydration fluid), and/or on historical treatment data including the treatment responses of one or more other patients. Accordingly, embodiments of the present technology are expected to optimize/customize all or a subset of a diuretic therapy to an individual patient's physiology, for example, to maximize decongestion and/or minimize clinical sequelae.

As described elsewhere herein, embodiments of the present technology can obtain one or more (e.g., multiple) inputs of urine output volume data from a patient without using an indwelling catheter (e.g., a Foley catheter). A typical indwelling catheter, such as a Foley catheter, is configured to be positioned at least partially within a patient's bladder. Accordingly, as the patient's kidneys excrete urine into the bladder, the indwelling catheter allows the excreted urine to flow from the bladder to a location outside the body (e.g., a urine collection container). This urine output is expected to occur automatically (e.g., without the patient voluntarily urinating) and/or continuously (e.g., urine excreted from the kidneys into the bladder is removed from the patient via the indwelling catheter, being held in the bladder for no more than 1 second, 5 seconds, 10 seconds, 15 seconds, 30 seconds, 1 minute, 5 minutes, 10 minutes, combinations thereof, and/or one or more other suitable amounts of time). Therefore, the indwelling catheter can be used to measure urine excretion by the patient's kidneys and, in turn, determine a urine output rate for the patient. However, many patients, clinicians, and/or institutions do not utilize indwelling catheters, opting instead for external catheters, such as condom catheters or PureWick™ catheters, or other non-indwelling catheters. External catheters are placed external to the patient and collect patient urination. Whereas indwelling catheters do not require patient urination (voluntary or otherwise) to receive and collect urine, external catheters rely on patient urination (voluntary or otherwise) to receive and collect urine. Often, patients that use external catheters urinate in large volumes or boluses (e.g., up to 1 liter) that are intermittent/periodic (e.g., no less than 10 minutes, 20 minutes, 30 minutes, combinations thereof, and/or one or more other suitable lengths of time apart from one another) throughout therapy. These patients also rarely/infrequently urinate while sleeping. Accordingly, whereas indwelling catheters can measure urine excretion from the kidneys, external catheters instead measure urination from the bladder. This can make it difficult to accurately determine a continuous urine and/or sodium output rate (i.e. urine and/or sodium excretion rate from the kidneys) for patients that use non-indwelling catheters and, accordingly, difficult to adjust fluid therapy received by patients that use non-indwelling catheters based on those patients' urine and/or sodium output rates. However, embodiments of the present technology can obtain one or more (e.g., multiple) inputs of urine output volume data from a patient without using an indwelling catheter and use that data to adjust one or more aspects of the patient's fluid therapy. For example, in some embodiments a fluid therapy system can obtain multiple inputs of urine output volume data from a patient without using an indwelling catheter, determine an accumulated volume of urine output data based on the obtained multiple inputs, and adjust the patient's fluid therapy based at least partially on the accumulated volume and/or the obtained multiple inputs. Additionally, or alternatively, the fluid therapy system can include one or more sensors disposed externally on and/or around the patient that measure a volume and/or a change in volume of urine within the patient's bladder, e.g., to determine a urine output rate of the patient. In doing so, embodiments of the present technology can advantageously manage a fluid therapy for patients that refuse an indwelling catheter.

Embodiments of the present technology can manage a patient's fluid removal (including to, e.g., increase or optimize the patient's urine output, net fluid removal, and/or net sodium removal) based at least in part on the measured urine output and the physician's estimated excess fluid volume. For example, in some embodiments if a patient's urine output drops below a pre-defined rate and the patient has lost 80% or more of the estimated excess fluid volume or less than 1 L of estimated excess fluid remains to be removed from the patient, then the system may determine that therapy should be stopped (e.g., automatically stopped) immediately or after a period of time (e.g., one hour). Alternatively, if a patient's urine output drops below a pre-defined rate and less than 80% of the estimated excess fluid volume has been removed and/or more than 1 L of estimated excess fluid remains to be removed from the patient, then the system may determine that it is necessary to take steps to increase urine production. In such embodiments, the system may recommend (e.g., via software, labeling, and/or combinations thereof) infusing or otherwise administering a second diuretic in addition to a first diuretic already being infused, and/or adjusting a rate of hydration fluid infusion. In doing so, embodiments of the present technology can advantageously manage a patient's urine output by ceasing one or more aspects of fluid therapy (e.g., diuretic infusion) for instances of sufficient fluid loss and improving fluid therapy by increasing urine output for instances of insufficient fluid loss.

Various aspects of one or more embodiments of the present technology can be based at least partially on one or more models ("model(s)"), such as artificial intelligence (AI) and/or machine learning (ML) models. Individual ones of these models can be trained using historical treatment data from one or more other patients and configured to determine and/or predict information about the patient receiving treatment, and/or otherwise inform the system's and/or the user's decisions regarding the patient's therapy. In at least some embodiments, the model(s) can be configured/trained to compare patient data with training data and/or data associated with fluid therapy and/or other treatments administered to one or more other patients. For example, for a given patient, the model(s) can be configured/trained to identify data associated with one or more other patients that have an at least generally similar treatment profile. A treatment profile can be at least generally similar to data for a given patient if/when data associated with the treatment profile and the data for the given patient share one or more treatment characteristics (e.g., patient diuretic resistance, glomerular filtration rate (GFR), patient age, patient gender, overall patient health, underlying health conditions, renal function, demographics, clinician estimated excess fluid, combinations thereof, and/or one or more other suitable treatment characteristics), urine rate profile (e.g., urine rate, slope of urine rate curve, plot of urine rate over time) an amount of fluid already removed from patient, a prior response to fluid therapy, combinations thereof, and/or other suitable treatment profile data. In some embodiments, rules for identifying an at least generally similar or identical treatment profile can be programmed into the model(s), and/or may correspond to values being within a range or threshold of one another (e.g., less than a 5%, 10%, 15%, 20%, 25%, or 30% difference). In other embodiments, the model(s) can identify/create rules, parameters, thresholds, combinations thereof, and/or one or more other suitable processes for identifying at least generally similar or identical treatment profiles, e.g., during training. Generally, the model(s) are expected to improve the effectiveness of the fluid therapy steps/blocks/protocols described herein. In some embodiments, the model(s) are expected to improve a specific patient's response to the fluid therapy steps/blocks/protocols described herein. In further embodiments, the model(s) can predict whether a patient is expected to respond to fluid therapy and/or are expected to optimize (e.g., maximize) a patient's response to the fluid therapy steps/blocks/protocols described herein in real-time, for example, based on data received from the patient associated with the patient's response to the fluid therapy.

The headings provided herein are for convenience only and are not intended to limit or interpret the scope or meaning of the technology.

II. Fluid Management Systems and Methods

The present technology is generally directed to systems, devices, and associated methods for fluid therapy based on patient data, including managing fluid levels of the patient based at least partially in response to data received from the patient before and/or during the fluid therapy. In some embodiments, the systems, devices, and methods described herein are used to treat a patient for fluid overload. To treat fluid overload, patients can be administered a diuretic drug which induces and/or increases urine production. For example, loop diuretics are diuretics that act at the ascending limb of the loop of Henle in the kidney, and include bumetanide (Bumex®), ethacrynic acid (Edecrin®), furosemide (Lasix®), torsemide (Demadex®), thiazide and thiazide-like diuretics (e.g., chlorothiazide, metolazone), potassium-sparing diuretics (e.g., amiloride, spironolactone), carbonic anhydrase inhibitors (e.g., acetazolamide), Vaptans (e.g., Conivaptan), SGLT2 inhibitors, and osmotic diuretics (e.g., mannitol). Diuretics can be given orally as a pill or as an intravenous (IV) injection. IV diuretics can be used when oral diuretics are no longer effective and/or able to be absorbed.

The short-term effects of diuretics on a patient's urine production may be difficult to predict, particularly at early stages of treatment. For example, one patient may produce much less urine than expected for a given dose of diuretic, while another patient administered the same dose may produce very large amounts of urine. Low urine production can prolong treatment time and/or reduce treatment efficacy, while high urine production can raise concerns of hypotension, hypovolemia, electrolyte imbalance (e.g., hypokalemia), and/or vital organ damage. High doses of a diuretic, regardless of the urine response, can also raise concerns about ototoxicity. Due to these uncertainties, physicians typically initially prescribe a conservative (e.g., low) diuretic dosage and often wait a full day or longer before considering whether to increase the diuretic dosage. If the physician determines that a higher diuretic dosage is needed, the physician may slowly and incrementally increase the dosage until the patient's urine output reaches the desired level and/or rate. However, this approach can prolong the time the patient remains in the fluid overloaded condition, which can exacerbate the patient's underlying clinical state. For example, conservative treatment procedures can require hours or even days before the patient's urine output is sufficiently high to cause significant fluid loss and relieve the fluid overload condition. The patient may be hospitalized for several days (e.g., 4-5 days), which can be expensive and burdensome. Additionally, the long-term treatment efficacy may be limited, such that approximately 25% of patients are readmitted for fluid overload within 30 days.

To overcome these and other challenges, the present technology provides systems, and associated devices and methods, for managing a patient's fluid levels. In some embodiments, the present technology can (i) improve efficacy, safety, and quality of fluid management treatment, (ii) improve resource management in hospitals and other clinical settings, (iii) quickly assess if a patient is diuretic resistant (e.g. within the first few hours of treatment), and/or (iv) increase diuretic efficiency (e.g., the amount of urine and/or excreted electrolytes (e.g., sodium) obtained over a given time per mg of diuretic infused intravenously). The embodiments described herein can increase net removal of fluid and/or electrolytes (e.g., sodium and/or chloride), and can also treat fluid overload conditions in a more efficient manner (e.g., shorter timeframe and/or higher net fluid loss).

FIG. 1 is a partially schematic illustration of a fluid management system 100 ("system 100") for monitoring urine output and/or control fluid infusion into a patient P, in accordance with embodiments of the present technology. The system 100 includes a urine collection and monitoring system 110 ("urine system 110"), an automated hydration fluid infusion system 120 ("hydration system 120"), an automated diuretic infusion system 130 ("diuretic system 130"), a controller or control system 140 ("controller 140"), and a display or input/output unit 150 ("display 150"). The controller 140 can be operably coupled to each of the urine system 110, hydration system 120, diuretic system 130, and/or display 150. The system 100 can further include a console or structure 105 ("console 105") that incorporates, houses, and/or otherwise supports all or portions of the urine system 110, hydration system 120, diuretic system 130, the controller 140, and/or the display 150.

The urine system 110 is configured to collect urine from the patient P and/or monitor the patient's urine output (e.g., urine output amount and/or rates). The urine system 110 can include one or more collection containers 112 ("container 112") configured to hold urine, such as a disposable bag or other collection device. The container 112 can be fluidly coupled to the patient P via a fluid line 119 (e.g., a tubing line). The fluid line 119 can be connectable to a disposable catheter 118 (e.g., a non-indwelling catheter, including external catheters such as Texas Condom catheters, PureWick catheters, and/or other suitable external catheters) configured to receive fluid from the bladder of the patient P.

In some embodiments, urine flow through the fluid line 119 is driven by the patient's urine production, gravity (e.g., the bladder of the patient P is positioned higher than the container 112), and/or a siphon effect between the patient's bladder and the container 112. In other embodiments, the urine system 110 can also include a pump, vacuum, or other device (not shown) operably coupled to the fluid line 119 for actuating urine flow through the fluid line 119 and into the container 112. The pump can be or include any device suitable for pumping fluid, such as a peristaltic pump. The pump can be used to initiate urine flow from the patient's body at the start of the procedure. The pump can also be used to clear air locks and/or other obstructions from the fluid line 119.

The urine system 110 can include one or more sensors 114 ("sensor(s) 114") configured to detect one or more characteristics of the patient's urine output (e.g., an amount and/or rate of urine output) and/or one or more electrical, chemical, and/or physical properties of the patient's urine including, e.g., urine sodium concentration, urine conductivity, urine temperature, urine oxygen content, and/or combinations thereof). Accordingly, the sensor(s) 114 can generate data based at least partially on the patient's urine such that the controller 140 can monitor and/or compute the patient's urine output based on the data generated by the sensor(s) 114.

The urine output can be determined in many different ways, such as based on urine flow (e.g., through the fluid line 119 and/or into the container 112), the amount of urine in the container 112 (e.g., based on the weight of the container 112, level of urine in the container 112, and/or combinations thereof), and/or other properties associated with the urine. The sensor(s) 114 can include one or more of the following: a flow sensor, drip counter, fluid weight sensor, fluid level sensor, float sensor, optical sensor, ultrasonic sensor, and/or other sensors known in the art suitable for measuring a urine output amount and/or rate. In the embodiment of FIG. 1, the sensor(s) 114 are positioned at the console 105. In other embodiments, however, some or all of the sensor(s) 114 can be at a different location in the system 100, such as on or in the line 119, on or in the container 112, and/or on or in the patient P.

In some embodiments, the sensor(s) 114 can include at least one sensor configured to measure one or more characteristics of the urine, in addition to detecting the patient's urine output. For example, the sensor(s) 114 can be configured to measure urine temperature, urine conductivity, urine oxygenation, urine specific gravity, and/or levels of one or more analytes in the urine (e.g., creatinine, sodium, potassium, combinations thereof, and/or one or more other suitable analytes). Such characteristics can be useful in, e.g., determining effectiveness of a particular therapy, whether the patient P is in or could be approaching a critical condition, and/or to inform diuretic and/or hydration fluid administration. For example, urine conductivity and/or urine electrolytes (e.g., sodium) can indicate whether the patient is responding well to the fluid therapy, or whether the patient is in a critical condition and fluid therapy should cease. In some embodiments, urine conductivity (either alone or in combination with urine specific gravity) is used as a proxy for measurements of urine sodium and/or other urine electrolytes, e.g., a higher urine conductivity can correlate to higher urine sodium levels and a lower urine conductivity can correlate to lower urine sodium levels. The urine conductivity and/or urine electrolyte levels can be used to determine a patient's actual urine sodium content and, accordingly, determine the patient's adjusted urine output rate. In some embodiments, the patient's actual urine sodium content can be measured directly by, e.g., one or more of the sensors 114. As another example, urine temperature measurements can be used to detect urine flow (e.g., based on heat loss through the fluid line 119). The urine temperature can also be used as a proxy for the patient's body temperature, which in turn can correlate to the patient's current clinical state.

Optionally, the sensor(s) 114 can include at least one sensor configured to monitor the status of the urine collection procedure, such as whether urine collection is proceeding normally, whether there are interruptions in urine flow, whether there is a blockage or leak in the urine system 110, and/or combinations thereof.) For example, the sensor(s) 114 can include a leak sensor configured to detect whether a leakage is present in the urine system 110 (e.g., at or near the fluid line 119, catheter 118, and/or container 112). Leaks can be detected based on changes in urine flow rate, changes in pressure, the presence of moisture, or any other suitable parameter. In some embodiments, the controller 140 is configured to analyze the data from the leak sensor and/or other sensor(s) 114 to differentiate between low urine output rates versus leaks in the urine system 110. In these and/or other embodiments, one or more leak sensors can be positioned on and/or around the patient P, e.g., to detect leaks from the catheter 118.

As another example, the sensor(s) 114 can include a pressure sensor configured to measure the fluid pressure in the fluid line 119. The controller 140 can use the pressure measurements to monitor the status of urine flow, and optionally, detect whether there are any interruptions (e.g., decreases, sudden stoppages) or other issues with urine collection. In some embodiments, the controller 140 analyzes the pressure measurements to determine whether interruptions are due to low urine flow (e.g., the patient's bladder is empty or nearly empty), an air lock or other obstruction in the fluid line 119 (e.g., based, at least in part, on the pressure rising above a predetermined pressure threshold), a leak in the urine system 110 and/or a kink in the fluid line 119 and/or catheter 118. The controller 140 can alert the user if manual intervention is helpful or needed (e.g., to clear the obstruction, fix the leak, remove kinks from the fluid line 119, and/or combinations thereof). In embodiments where the urine system 110 includes a pump, the controller 140 can automatically activate the pump and/or increase the pumping rate to clear the obstruction from the fluid line 119.

The hydration system 120 can include at least one hydration fluid source 122 ("fluid source 122"—a bag, bottle, reservoir, and/or combinations thereof) containing a hydration fluid, such as saline (e.g., a premixed saline solution), Ringer's lactate solution, and/or other any other liquid solution suitable for infusion in and/or configured to prevent or treat dehydration of the patient P. The hydration fluid can be isotonic, hypertonic, or hypotonic, e.g., depending on the patient's condition and/or other treatment considerations. Optionally, the composition of the hydration fluid (e.g., sodium, chloride, potassium, bicarbonate, other substances and/or compounds, and/or combinations thereof) can be varied based on the patient's condition and/or expected or measured electrolyte loss during the treatment procedure.

The fluid source 122 can be connected to the patient P via at least one fluid line (e.g., an IV line or other tubing), such as first fluid line 129a and a second fluid line 129b. The fluid source 122 can be operably coupled to one or more hydration fluid components 124 for actuating and/or monitoring hydration fluid infusion via the first and second fluid lines 129a-b, such as a hydration fluid pump 126 and/or at least one hydration fluid sensor 128 ("fluid sensor 128"). In the illustrated embodiment, the fluid source 122 is fluidly coupled to the hydration fluid pump 126 via the first fluid line 129a, and the hydration fluid pump 126 can pump the hydration fluid into the patient P via the second fluid line 129b. The hydration fluid pump 126 can be or include a peristaltic pump or other pump suitable for infusing a fluid into the patient's body (e.g., via an IV route or another route).

The fluid sensor 128 can be configured to determine an amount and/or rate of hydration fluid flowing from the fluid source 122 toward the patient P, and can include a flow sensor, pressure sensor, and/or other sensor configured to determine fluid output from the pump 126. Alternatively, or in combination, the fluid sensor 128 can monitor hydration infusion rate by measuring the pumping rate of the pump 126 (e.g., the number of rotations of the pump 126 per minute). As described elsewhere herein, the controller 140 can be operatively coupled to the hydration system 120 and can receive sensor data from the fluid sensor 128 to determine a hydration fluid infusion rate. The controller 140 can control the pumping rate of the pump 126 to control the amount and/or rate of hydration fluid provided to the patient P.

Optionally, the amount of hydration fluid in the fluid source 122 can be monitored, e.g., based on weight, volume, fluid levels, flow rates, and/or combinations thereof. In such embodiments, the fluid source 122 can be operably coupled to an additional sensor separate from the fluid sensor 128 (not shown), such as a fluid level monitor, float sensor, weight sensor, optical sensor, drip counter, flow measurement sensor, or the like. The additional sensor can provide an independent source of measurement data for determining and/or verifying the amount and/or rate of hydration fluid being provided to the patient P, which can be helpful for improving measurement accuracy.

In some embodiments, the hydration system 120 includes at least one sensor configured to detect the presence of the fluid source 122, such as a location sensor, optical sensor, weight sensor, one or more other sensors, and/or combinations thereof. The hydration system 120 can use the sensor data to automatically determine whether the fluid source 122 is present or absent, e.g., to assess whether the system 100 is ready to initiate the fluid therapy treatment. Optionally, the sensor data can be used to detect if the user is removing the fluid source 122 during the treatment procedure, e.g., to switch an empty or nearly empty fluid source 122 with a new fluid source 122. In such embodiments, the system 100 can automatically pause hydration fluid infusion until the fluid source 122 has been replaced. Accordingly, the user can switch fluid sources 122 without having to inform the system 100 or manually pause the procedure.

The diuretic system 130 can be configured to automatically provide a diuretic to the patient P. The diuretic system 130 can include a diuretic source 134 (e.g., syringe, bag, reservoir, and/or combinations thereof) containing a diuretic, such as bumetanide (Bumex®), ethacrynic acid (Edecrin®), furosemide (Lasix®), torsemide (Demadex®), and/or other diuretics known in the art, each of which may be part of a fluid solution (e.g., a mixture of saline and a diuretic or other agent). In some embodiments, the identity and/or concentration of the diuretic can be received by the controller 140 via user input (e.g., using the display 150), by scanning a barcode of the diuretic source 134 or other container of the diuretic, and/or any other suitable technique.

The diuretic source 134 can be connected to the patient P via a fluid line 139 (e.g., an IV line or other tubing). The diuretic source 134 can also be operably coupled to one or more diuretic components 136 for actuating and/or monitoring diuretic delivery via the fluid line 139. For example, the diuretic components 136 can include a diuretic pump configured to pump the diuretic through the fluid line 139 and toward the patient P. The diuretic pump can include a peristaltic pump, a syringe pump, a metering pump, or other device suitable for delivering the diuretic to the patient P at a plurality of dosage rates. The diuretic pump can deliver the diuretic according to any suitable delivery profile, such as at a controlled continuous rate and/or in controlled boluses delivered at regular intervals through the fluid line 139.

In some embodiments, the diuretic pump is or includes a syringe pump having a mechanical injector or plunger that is operably coupled to the controller 140, such that the controller 140 causes movement of the injector to transfer the diuretic to the patient P. The syringe pump can include or be coupled to an actuator that mechanically drives the injector to control the delivery of the diuretic to the patient P. For example, the actuator can be or include a mechanical actuator, such as a nut for rotating a screw to drive the injector. The syringe pump can also include or be operably coupled to a sensor for detecting the position of the injector. Alternatively, or in combination, the diuretic pump can include other types of pumps and/or actuators. For example, the diuretic pump can include a motor, a gearbox operatively connected to the motor, a sensor for measuring rotation of said motor (e.g., a tachometer or an optical encoder), and/or a microcontroller configured to control operation of the motor and monitor the quantity of diuretic delivered to the patient P. As another example, the diuretic pump can include an electric motor, such as a rotary motor, a linear motor, and/or a series of electrically actuated solenoids configured to propel liquid from the diuretic source 134 and through the line 139 toward the patient P.

In some embodiments, the diuretic components 136 include one or more diuretic sensors configured to determine an amount and/or rate of diuretic flowing toward the patient P. The one or more diuretic sensors can include, for example, a flow sensor, weight sensor, and/or other sensor type configured to determine the amount and/or rate of diuretic delivered from the diuretic source 134. Optionally, the diuretic sensors can measure diuretic delivery based on the output from the diuretic pump, such as by monitoring the pumping rate (e.g., number of rotations of the diuretic pump per minute, plunger position, and/or combinations thereof). The diuretic components 136 can include additional functional components, such as an air bubble detector, pressure sensor, extravasation sensor (e.g., ivWatch device), and/or other embedded electronics, e.g., to provide feedback signals to the controller 140 to ensure accurate diuretic infusion and/or monitor infusion status.

The controller 140 is configured to automatically control hydration fluid and/or diuretic infusion (e.g., based at least in part on the patient's urine output) to promote safe and effective diuresis and/or natriuresis (e.g., sodium output) of the patient P. The controller 140 can include one or more processor(s) and tangible, non-transient memory configured to store programmable instructions. The controller 140 can be operably coupled to the urine system 110, hydration system 120 and/or diuretic system 130 to receive data (e.g., sensor data) from and transmit data (e.g., control signals) to the various components of these systems. For example, the controller 140 can receive sensor data from the urine system 110 (e.g., from sensor(s) 114) to determine and/or monitor the patient's urine output. Based on the urine output, the controller 140 can determine an appropriate diuretic dosage amount and/or rate to administer to the patient P, and can cause the diuretic system 130 to deliver the diuretic accordingly. For example, the controller 140 can determine a pumping rate of the diuretic pump to produce the desired delivery profile for the diuretic. Similarly, the controller 140 can determine an appropriate hydration fluid infusion rate for the patient P (e.g., based on the urine output, the diuretic dosage rate, and/or the urine sodium concentration), and can cause the hydration system 120 to deliver the appropriate hydration fluid amount and/or rate. For example, the controller 140 can determine a pumping rate for the hydration fluid pump 126 to achieve the desired hydration fluid infusion rate. The controller 140 can regulate the diuretic dosage rate and/or hydration fluid infusion rates based on a suitable treatment regimen protocol, e.g., prescribed by a physician and/or managed by the controller 140.

During the procedure, the controller 140 can receive sensor data from the various sensors of the urine system 110, hydration system 120 and/or diuretic system 130 to monitor the urine output, hydration fluid infusion rate, and/or diuretic dosage rate, respectively. The controller 140 can also receive sensor data from additional sensors configured to monitor patient status and/or operational status of the system 100, such as fluid pressure sensors, blood pressure sensors, air bubble detectors, analyte detectors, urine conductivity sensors, and the like. For example, the controller 140 can be operably coupled to at least one sensor implanted in, attached to, or otherwise associated with the patient P. The sensor(s) can provide data regarding any of the following patient parameters: pressure levels (e.g., pulmonary artery pressure, left atrial pressure), bioelectric measurements (e.g., bioimpedance vector analysis (BIVA)), hemoglobin measurements (e.g., non-invasive hemoglobin measurements), urine oxygenation levels, urine composition (e.g., creatinine, sodium, potassium, chloride, and/or combinations thereof), urine temperature, body temperature (e.g., bladder temperature), oral fluid intake, heart rate, heart rate variability, blood oxygenation, hematocrit, hemodynamic data, and any other data described herein. The controller 140 can use the data from any of the sensors described herein to monitor treatment progress (e.g., whether the treatment is complete), patient status (e.g., whether the patient is responding well or poorly to treatment), adjust one or more parameters of the fluid therapy (e.g., increase or decrease the hydration fluid infusion rate and/or the diuretic dosage rate) and/or potential safety concerns (e.g., whether the diuresis is too aggressive, whether the patient is exhibiting side effects). The controller 140 can also adjust the hydration fluid infusion rate and/or diuretic dosage rate based on the sensor data. Additionally, the sensor data can also provide feedback to the controller 140 to confirm or verify the effectiveness of the fluid therapy.

The controller 140 can also use other data for monitoring and/or controlling the therapy, such as settings for the system 100, user input, data indicative of a desired treatment regimen (e.g., a programmed diuretic and/or hydration fluid delivery profile over time), and/or other data collected or calculated by the controller 140. In some embodiments, the data used by the controller 140 includes current and/or historical data for the patient P, such as diuretic dosages delivered to the patient P, urine output volume or rate, the amount of hydration fluid infused into the patient P, the weight or change in weight of the patient P at various times during the infusion of the diuretic, indicators of the patient's renal function (e.g., estimated glomerular Filtration Rate (eGFR)), and/or the time(s) during which the patient P was treated with the system 100. Additionally, or alternatively, the data used by the controller 140 can include historical data for one or more other patients, as described elsewhere herein.

The display 150 (e.g., a touchscreen, monitor, and/or one or more other display devices) can include a user interface configured to receive inputs from the user and display outputs to the user. In some embodiments, the display 150 is operatively coupled to the controller 140 and thus can be used to receive user input indicating treatment parameters, such as parameters for urine output, hydration fluid infusion, and/or diuretic dosage. The treatment parameters can include, for example: a desired fluid balance level (e.g., a positive, negative, or neutral fluid balance), estimated excess fluid volume, target fluid removal volume (e.g., minimum and/or maximum amount of fluid to be removed), desired urine output level (e.g., a total amount of urine output; a target maximum, minimum, and/or average urine output rate), treatment duration (e.g., maximum and/or minimum duration of the treatment procedure; planned duration of the input balance level and/or urine output level), hydration fluid type, hydration fluid infusion rate (e.g., maximum, minimum, and/or average infusion rate), hydration fluid infusion profile (e.g., a function indicating how the amount and/or rate of hydration fluid infusion should vary over time), time limits associated with hydration fluid infusion (e.g., maximum and/or minimum time period for hydration fluid infusion), diuretic type, diuretic dosage (e.g., maximum and/or minimum dosage), diuretic dosage rate (e.g., maximum, minimum, and/or average dosage rate), diuretic dosage profile (e.g., a function indicating how the dosage amount and/or dosage rate of diuretic should vary over time), time limits associated with diuretic delivery (e.g., maximum and/or minimum time period for diuretic delivery), other fluids received by the patient during the procedure (e.g., volume of ingested fluid, volume of fluid from other medical agents besides the diuretic and/or hydration fluid), and/or suitable combinations thereof. Other patient-related inputs may also be received at the display 150 and can include, for example, the patient's sex, weight (e.g., "dry" weight), age, ethnicity, clinical state (e.g., renal function parameters, electrolyte levels such as serum chloride levels), medical history (e.g., outcomes of previous fluid removal procedures, prior response to fluid therapy, and/or combinations thereof), diagnoses (e.g., ADHF, CHF), medications (e.g., whether the patient is diuretic-naïve or diuretic-resistant), dietary factors (e.g., whether the patient is consuming a high-salt or low-salt diet, amount of oral fluid intake), and/or combinations thereof.

Alternatively, or in combination, the user input via the display 150 can prompt the controller 140 to retrieve treatment parameters (e.g., maximum diuretic dosage, maximum continuous diuretic dosage, and minimum desired urine rate) from tables and/or other data sources. The data sources can be stored in the system 100 (e.g., in a memory associated with the controller 140) and/or can be stored in a separate device (e.g., a remote computing device). In some embodiments, the controller 140 retrieves data from a remote database and/or server via a communication network (e.g., a wired network, a wireless network, a cloud-based network, the Internet, and/or suitable combinations thereof). In such embodiments, the controller 140 can be operably coupled to a communication device and/or interface configured to transmit and receive data via the communication network.

The controller 140 can output the treatment parameters to the user via the display 150 for review and/or feedback. For example, the display 150 can show recommended treatment parameters for the patient P, such as recommendations for the diuretic, diuretic dosage rate (e.g., initial, maximum, and/or minimum dosage rate), hydration fluid infusion rate (e.g., initial, maximum, and/or minimum infusion rate), urine output rate (e.g., measured urine output rate, sodium-adjusted urine output rate, maximum and/or minimum output rate), sodium and/or other electrolyte output rate, treatment duration (e.g., maximum time period for diuretic and/or hydration fluid infusion; maximum total treatment duration), treatment escalation (e.g., thiazide, temporarily increased fluid matching, additional loop diuretic), end of treatment, and so on. As another example, the display 150 can output one or more predetermined treatment programs so the user can select the appropriate program for the particular patient P. Optionally, the user can modify any of the displayed treatment parameters, if desired.

During the treatment procedure, the controller 140 can output information regarding procedure status to the user via the display 150. For example, the controller 140 can display information regarding any of the following: urine output (e.g., current urine output rate and/or amount, urine output rate and/or amount over time, total amount of urine output so far), hydration fluid infusion (e.g., current infusion rate and/or amount, infusion rate and/or amount over time, total amount of hydration fluid infused so far), diuretic delivery (e.g., current dosage rate and/or amount, dosage rate and/or amount over time, total amount of diuretic delivered so far), fluid balance (e.g., current fluid balance, fluid balance over time, net fluid removal so far), system status (e.g., amount of hydration fluid remaining in the fluid source 122, amount of diuretic remaining in the diuretic source 134, remaining storage capacity in the container 112), treatment time (e.g., treatment start time, projected and/or planned treatment end time, total treatment duration so far), notifications (e.g., alerts, alarms, messages, recommendations, predictions, error messages), and the like. The user can review the displayed information, and, if appropriate, provide input instructing the controller 140 to adjust, pause, and/or stop the treatment procedure.

In some embodiments, the system 100 includes redundancy in the urine system 110, hydration system 120, and/or diuretic system 130 to reduce or minimize treatment interruptions, e.g., due to running out of urine collection capacity, running out of hydration fluid, and/or running out of diuretic. For example, the system 100 can include redundant components (e.g., containers 112, fluid sources 122, and/or diuretic sources 134), which can be stored at predetermined locations (e.g., on or within the console 105 or another portion of the system 100). The controller 140 can be configured to detect the presence of the redundant components and can automatically or semi-automatically switch between these components so the treatment procedure can continue uninterrupted or substantially uninterrupted. Alternatively, or in combination, the system 100 can adjust the timing of user alerts related to urine collection capacity, hydration fluid levels, and/or diuretic levels, based on the availability of redundant components. For example, if redundant components are available, the system 100 can generate alerts at a later time (e.g., closer in time to when the container 112 would be full, when the fluid source 122 would be empty, and/or when the diuretic source 134 would be empty), since the system 100 can automatically switch to using the redundant components, or the user can rapidly perform the switch using the redundant components that are already stored locally at the system 100, rather than having to retrieve replacements from another location.

The lack of interruption in fluid therapy can help ensure effectiveness of the fluid therapy, e.g., by relieving the patient's fluid overload condition as quickly and safely as possible. In some embodiments, even brief interruptions in diuretic delivery and/or hydration fluid infusion can significantly affect the patient's urine output (e.g., cause the urine output rate to drop), which can interfere with therapeutic efficacy and prolong treatment time. The concerns described above regarding diuretic and/or hydration fluid backup supply may be unique to the present technology, e.g., due to the relatively large amounts of diuretic and/or hydration fluid that are utilized over time in some embodiments of the treatment procedures described herein. That is, whereas conventional systems and methods may utilize just a single diuretic source and/or a single hydration fluid source because of the relatively low amount of diuretic and/or hydration fluid administered, the present technology may benefit from multiple diuretic sources and/or hydration fluid sources to ensure treatment continuity. Similarly, the treatment procedures of the present technology can cause the patient P to produce relatively large volumes and/or rates of urine output compared to conventional procedures, such that multiple containers 112 may be helpful to reduce the number of times the user has to empty and/or replace the containers 112 during the procedure.

For example, in some embodiments, the urine system 110 includes two or more redundant containers 112 to ensure fluid therapy does not need to be stopped or interrupted due to the container 112 being full. In such embodiments, the urine system 110 can include a flow control assembly 116 (e.g., valves and/or other flow control components) operably coupled to the controller 140 and configured to selectively direct the urine from the patient P to one or more of the containers 112. The flow control assembly 116 can initially direct the urine received from the patient P to a first container 112. Once the flow control assembly 116 detects or determines the first container is full or nearly full (e.g., based on sensor data from the sensor(s) 114), the flow control assembly 116 can redirect the urine received from the patient P to a second container 112. While urine is being directed to the second container 112, a user can empty the first container 112 or replace the first container 112 with an empty container 112. The flow control assembly 116 and/or controller 140 can generate an alert to the user to indicate the first container is full and needs to be replaced or emptied. This process can be repeated such that fluid management therapy is not inadvertently interrupted due to the containers 112 being full and/or the urine system 110 being unable to accept urine output. In some embodiments, the treatment procedures described herein result in relatively large amounts and/or rates of urine output (e.g., compared to conventional therapies), such that automatic switching between multiple urine containers is advantageous to minimize treatment interruptions.

As another example, the hydration system 120 can include multiple redundant hydration fluid sources 122, e.g., to ensure the hydration fluid infusion can continue without interruption for the entirety of a therapy session and/or to provide an additional time window for switching hydration fluid sources 122 without interrupting hydration fluid infusion. In such embodiments, the hydration system 120 can include a hydration control assembly (e.g., valves and/or other flow control components—not shown) operably coupled to the controller 140 and configured to switch the source of hydration fluid from a first fluid source 122 to a second fluid source 122. In such embodiments, the hydration control assembly can initially deliver hydration fluid from the first fluid source 122 to the patient P. The hydration control assembly can monitor whether the first fluid source 122 is empty or nearly empty, e.g., based on data from the fluid sensor 128 and/or other sensors associated with the hydration system 120. Once the hydration control assembly detects or determines the first fluid source 122 is empty or nearly empty (e.g., the remaining amount of hydration fluid is below a predetermined threshold), the hydration control assembly can switch to delivering hydration fluid from the second source 122. The switching process can be repeated such that fluid therapy is not inadvertently interrupted due to the fluid source 122 being empty and/or the hydration system 120 being unable to provide hydration fluid.

The process of switching the hydration fluid source 122 can be performed automatically, semi-automatically, or manually. In some embodiments, semi-automatic or manual switching between the first and second fluid sources 122 may be beneficial to ensure the hydration system 120 does not automatically infuse hydration fluid without user confirmation. In such embodiments, the hydration control assembly and/or controller 140 can output an alert asking the user to verify that the hydration fluid should be switched from the first fluid source 122 to the second fluid source 122. Upon switching to the second fluid source 122, the controller 140 can generate an alert to the user to indicate the first fluid source 122 is empty and needs to be replaced. Optionally, the hydration control assembly and/or controller 140 can implement a pre-approval procedure in which the user allows the hydration system 120 to automatically infuse a specified volume of additional hydration fluid. Once that volume has been delivered to the patient P, the user may need to provide re-approval before further automatic infusion of hydration fluid.

In some embodiments, the different fluid sources 122 of the hydration system 120 each provide the same type of hydration fluid. In other embodiments, however, some or all of the fluid sources 122 can provide different types of hydration fluid. The hydration fluids can differ from each other with respect to tonicity, composition, electrolyte content, one or more other properties, and/or combinations thereof. Depending on the patient's response to diuresis, the hydration system 120 can deliver multiple different hydration fluids to the patient P sequentially or concurrently. For example, if the patient's urine output indicates that the patient P has an electrolyte imbalance (e.g., a positive sodium balance), the hydration system 120 can switch to delivering a hydration fluid that would address the imbalance (e.g., a hydration fluid with lower sodium content). The switching can be performed using any of the techniques and/or devices described above. Accordingly, the particular fluid or fluids delivered to the patient P can be tailored to the patient's particular clinical state and/or response to treatment.

In yet another example, the diuretic system 130 can include multiple redundant diuretic sources 134, e.g., to ensure the diuretic delivery can continue without interruption for the entirety of a therapy session and/or to provide an additional time window for switching diuretic sources 134 without interrupting diuretic delivery. For example, if a first diuretic source 134 (e.g., a first syringe or container) is spent, the diuretic can continue to be supplied (e.g., without substantial interruption) via a second diuretic source 134 (e.g., a second syringe or container). The second diuretic source 134 can be connected to the console 105 and can be operably coupled to a sensor configured to detect the presence of the second diuretic source 134 (e.g., a location sensor, optical sensor, weight sensor, one or more other sensors, and/or combinations thereof). Accordingly, the diuretic system 130 can switch to the second diuretic source 134 if the first diuretic source 134 is empty or nearly empty, and the second diuretic source 134 is present.

In some embodiments, the diuretic system 130 includes two independent diuretic pumps each including its own diuretic source 134. For example, the diuretic system 130 can include syringe pumps each fluidly coupled to its own syringe filled with diuretic. In some cases, such syringes may only be filled by pharmacists or other health care professionals, and thus may not be readily replaced (e.g., in less than a few hours) by the user. When the diuretic system 130 and/or controller 140 detects that the first diuretic source 134 is empty or nearly empty (e.g., below a predetermined threshold), the diuretic supply can be switched (e.g., automatically or manually) to a second diuretic source 134. The switching process can include stopping a first syringe pump fluidly coupled to the first syringe, and starting a second syringe pump fluidly coupled to the second syringe. In other embodiments, the diuretic system 130 includes a single diuretic pump (e.g., syringe pump) connected to two diuretic sources 134. In such embodiments, case switching between the first and second diuretic sources 134 can involve using a diuretic control assembly (e.g., valves and/or other flow control components) to switch the diuretic pump from delivering diuretic from the first diuretic source 134 to the second diuretic source 134. The switching process can be repeated such that fluid therapy is not inadvertently interrupted due to the diuretic source 134 being empty and/or the diuretic system 130 being unable to provide diuretic.

The process of switching the diuretic source 134 can be performed automatically, semi-automatically, or manually. In some embodiments, manual or semi-automatic switching between the first and second diuretic sources 134 may be beneficial to ensure the diuretic system 130 does not automatically infuse a large volume of diuretic without user confirmation. In such embodiments, the controller 140 can output an alert asking the user to verify that the diuretic should be switched from the first diuretic source 134 to the second diuretic source 134. Upon switching to the second diuretic source 134, the controller 140 can generate an alert to the user to indicate the first diuretic source 134 is empty and needs to be replaced. Optionally, the controller 140 can predict a time point and/or time range when the first diuretic source 134 will be empty (e.g., based on the diuretic dosage rate), and can output a notification so the user can order or otherwise prepare a replacement diuretic source 134 before the first diuretic source 134 runs out. Moreover, the diuretic control assembly and/or controller 140 can implement a pre-approval procedure in which the user allows the diuretic system 130 to automatically delivery a specified additional dosage of diuretic. Once that dosage has been delivered to the patient P, the user may need to provide re-approval before further automatic delivery of diuretic.

In some embodiments, the different diuretic sources 134 of the diuretic system 130 each provide the same type of diuretic. In other embodiments, however, some or all of the diuretic sources 134 can provide different types of diuretics. Depending on the patient's response to diuresis, the diuretic system 130 can deliver multiple different diuretics to the patient P sequentially or concurrently. For example, the diuretic system 130 can initially deliver a first diuretic to the patient P from a first diuretic source 134. If the patient P responds poorly to the first diuretic (e.g., the urine output rate does not increase or increases very slowly), the diuretic system 130 can switch to delivering a second, different diuretic from a second diuretic source 134. The diuretic system 130 can continue delivering the first diuretic concurrently with the second diuretic or can terminate delivery of the first diuretic when the second diuretic is delivered. The switching can be performed using any of the techniques and/or devices described above. As another example, if the patient P does not respond well to a single diuretic, the diuretic system 130 can simultaneously administer multiple diuretics to the patient P. The ratio of the different diuretics can be varied as appropriate to elicit a suitable urine output rate. In other embodiments, however, rather than automatically administering additional diuretics, the diuretic system 130 can output a notification recommending that the user manually administer a different diuretic to the patient P and/or requesting that the user approve administration of a different diuretic, which may be beneficial for patient safety. Without being bound by theory, some diuretics are absorbed at a proximal end of the kidney and other diuretics are absorbed at a distal end of the kidney and using combinations of diuretics that are absorbed at the proximal and distal ends can be effective for improving overall fluid therapy.

The system 100 illustrated in FIG. 1 can be configured in many different ways. For example, the locations of the various components of the system 100 can be altered, e.g., the urine system 110, hydration system 120, and/or diuretic system 130 can be at different locations in the console 105. As another example, any one of the urine system 110, hydration system 120, or diuretic system 130 can be part of a separate system or device (e.g., a separate console), or can be omitted altogether. For instance, in some embodiments, the urine system 110 is replaced with a mechanism for monitoring the patient's urine output that does not require the catheter 118 and/or urine collection, such as one or more ultrasound sensors that measures the patient's bladder volume. The ultrasound sensor can be implemented as a patch or similar device that is coupled to the patient's body. The controller 140 can process the ultrasound sensor data to detect changes in the bladder volume and can determine the corresponding amount and/or rate of urine output based on the bladder volume. The use of non-invasive urine monitoring mechanisms such as an ultrasound sensor can allow the treatment procedures described herein to be performed in outpatient settings.

As another example, in some embodiments, the hydration system 120 is omitted such that diuresis is performed without hydration fluid infusion, or the hydration fluid is infused manually. Diuresis with hydration fluid infusion may be more beneficial for patients with low serum chloride levels (e.g., patients with low-salt diets), while patient with high serum chloride levels (e.g., patients with high-salt diets) may tolerate diuresis with little or no hydration fluid infusion. Optionally, the hydration fluid infusion rate can be varied at least partially based on the patient's serum chloride levels, e.g., lower amounts and/or rates of hydration fluid infusion can be used if the patient's serum chloride level is high (e.g., greater than or equal to 105 mmol/L).

In yet another example, the diuretic system 130 can be omitted such that no diuresis is performed, or the diuresis is performed manually. In such embodiments, the system 100 can provide automated fluid replacement via the hydration system 120 and/or can automatically monitor the patient's urine output via the urine system 110, but the diuretic would be administered manually by a healthcare professional in accordance with techniques known to those of skill in the art.

The system 100 can optionally include or be used in combination with additional systems or devices, such as systems or devices configured to perform any the following functions: administering other medications and/or agents besides the diuretic and hydration fluid (e.g., heart failure medication), monitoring other patient parameters besides urine output (e.g., blood pressure, weight, heart rate, blood oxygenation, respiratory rate, temperature), and/or performing other types of medical procedures on the patient P concurrently or sequentially with the fluid removal procedure (e.g., dialysis, ultrafiltration).

In some embodiments, the system 100 includes a platform 160 and the patient P, the patient's belongings (e.g., such as the patient's mobile phone 170), food, drink, clothing, the bed or other furniture upon which the patient resides, and/or other objects used by the patient during fluid therapy can be placed on the platform 160 during fluid therapy. As shown in FIG. 1, the console 105 can be positioned elsewhere, e.g., not on the platform 160. The platform 160 can include a weight sensor and/or be otherwise configured to obtain a weight (or a change in weight) of the objects positioned on the platform 160. If the patient P does not utilize a catheter 118 (e.g., a foley or other catheter), the patient P can be instructed to remain on the platform 160 except when urinating and, accordingly, changes in the weight obtained by the platform can correspond to the patient's urine output. If the patient has bowel movements, vomits, and/or takes one or more other actions besides urinating that may affect the patient's weight when off the platform, changes in weight (or estimations thereof) associated with these actions can be input into the system 100.

In some embodiments, one or more external sensors 180 can be disposed on the patient P and/or otherwise positioned to measure a dimension of one or more of the patient's organs. For example, the one or more external sensors 180 can be positioned to measure a volume (or change in volume) of the patient's bladder, and/or a volume (or change in volume) of urine contained within the patient's bladder. Data from the one or more external sensors 180 can be used to determine a urine output of the patient. The one or more external sensors 180 can include an ultrasonic sensor, a magnetic resonance imaging (MRI) sensor, a bioimpedance sensor (e.g., an electrical impedance tomography (EIT) sensor) a radar sensor, a computed tomography (CT) sensor, and/or one or more other suitable sensors, including any other sensors described herein. When the one or more external sensors 180 are worn/disposed on the patient P, the patient P can be instructed to minimize movement, avoid fluid intake, or take other measures that may affect the accuracy of the one or more external sensors 180.

Figure 2:
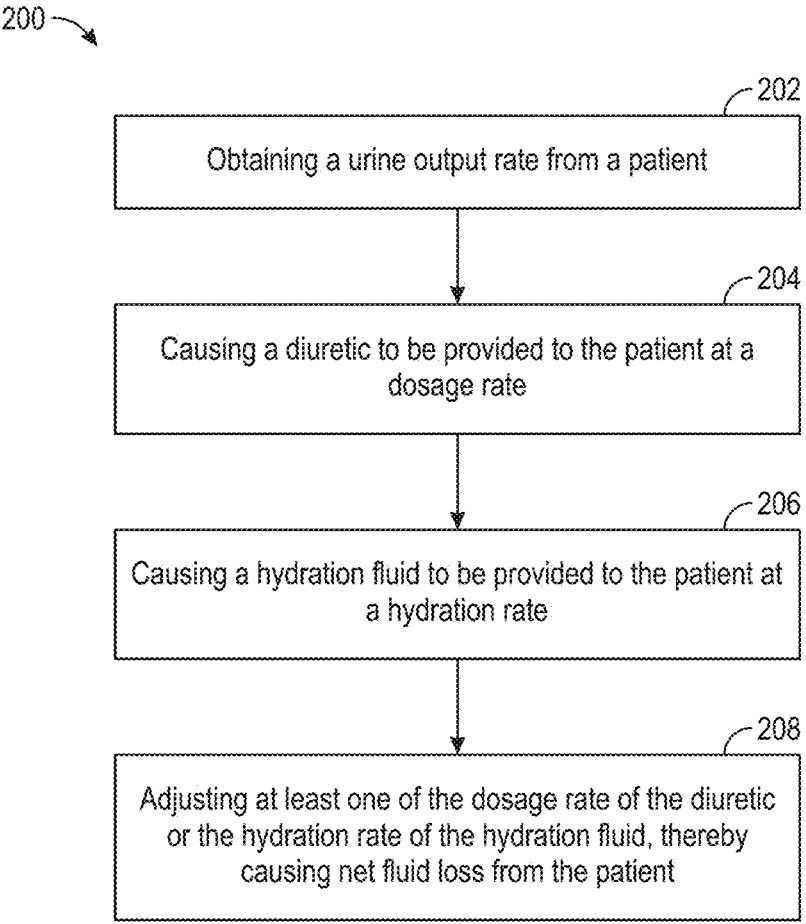
FIG. 2 is a flow diagram of a method for treating a patient, in accordance with embodiments of the present technology.

FIG. 2 is a flow diagram of a method 200 for treating a patient, in accordance with embodiments of the present technology. In some embodiments, the method 200 is used to treat the patient for fluid overload by removing fluid from the patient to produce a negative fluid balance (net fluid loss). The method 200 can be performed by any embodiment of the systems and devices described herein, such as the system 100 of FIG. 1. In some embodiments, some or all of the blocks of the method 200 are performed by a system or device including one or more processors and a memory storing instructions that, when executed by the one or more processors, cause the system or device to perform one or more of the blocks described herein. For example, the method 200 can be performed by the controller 140 of the system 100 of FIG. 1, CPU 341 of FIG. 3B, and/or another suitable processor. Optionally, some or all of the blocks of the method 200 can performed automatically or semi-automatically, with little or no human intervention.

The method 200 can begin at block 202 with obtaining a urine output rate from a patient. In some embodiments, obtaining the urine output rate can include obtaining the urine output rate via a urine monitoring and/or collection system connected to the patient, such as the urine system 110 of FIG. 1. The urine monitoring and/or collection system can, for example, determine the urine output rate based at least partially on one or more received inputs of urine output data, such as data obtained via one or more sensors (e.g., the sensor(s) 114 of FIG. 1) configured to measure the urine output rate based on flow rate, weight (e.g., of the container 112 of FIG. 1), volume, fluid level, and/or any other suitable parameter. The urine output rate can be calculated based on the received input, e.g., by a controller (e.g., controller 140 of FIG. 1) operatively coupled to the sensor(s). The urine output rate can be a current rate or an average rate measured over a predetermined time period (e.g., the previous 5 or 10 minutes). The urine output rate can be updated on a continuous or recurring basis (e.g., every 30 seconds, 1 minutes, 2 minutes, and/or combinations thereof). In at least some embodiments, obtaining the urine output rate can include obtaining the urine output rate without using an indwelling catheter. In some embodiments, the process of block 202 is performed concurrently with some or all of the other blocks of the method 200 (e.g., blocks 204, 206, and/or 208) to provide continuous or substantially continuous urine output monitoring through the entirety of the method 200.

In some embodiments, one or more of the sensors can be disposed on the patient and/or otherwise positioned to measure a dimension of an organ of the patient and block

202 can include obtaining the urine output rate based at least partially on the measured dimension of the organ. For example, the one or more sensors can include one or more of the external sensors 180 (FIG. 1) which, as described elsewhere herein, can be positioned to measure a volume (or change in volume) of the patient's bladder and/or a volume (or change in volume) of urine contained within the patient's bladder, including volumes/changes associated with urination by the patient. In some embodiments, obtaining the urine output rate via one or more of the external sensors includes obtaining the urine output rate during (e.g., only during) the diuretic dose finding phase of fluid therapy and, at one or more other times during fluid therapy (e.g., during the continuous delivery phase), the one or more external sensors 180 can be removed from the patient and obtaining the urine output rate can include obtaining the urine output rate based at least partially on urine received via a non-indwelling catheter as described further below and/or via one or more other devices configured to measure the patient's urine output, such as the platform 160 (FIG. 1).

At block 204, the method 200 optionally continues with causing a diuretic to be provided to the patient at a dosage rate. The diuretic can be or include furosemide, bumetanide, ethacrynic acid, torsemide, combinations thereof, and/or other diuretics known in the art. In some embodiment, the diuretic is delivered as part of a solution including saline or other hydration fluid(s) mixed therewith. The diuretic can be provided automatically or semi-automatically by a diuretic system connected to the patient, such as the diuretic system 130 of FIG. 1. The diuretic system can be operably coupled to a controller (e.g., controller 140 of FIG. 1) for causing diuretic delivery in accordance with a planned and/or pre-programmed treatment procedure.

In some embodiments, the treatment procedure includes multiple phases, and each phase is associated with a different delivery profile for the diuretic. In such embodiments, block 204 can be performed as part of an initial phase to determine an appropriate diuretic dosage rate for treating the patient (also known as a "dosage determining phase"). In the dosage determining phase, the diuretic is injected at an initial dosage rate, and the dosage rate can then be gradually increased (e.g., "ramped") to elicit an increase in the patient's urine output rate. The diuretic dosage rate can be increased according to a desired function or delivery profile, such as a continuous function, a block-wise function, or a combination thereof). The function can include iteratively increasing the dosage rate linearly, exponentially, according to a polynomial function, and/or any other suitable ramp function or profile. In some embodiments, the diuretic is delivered in a manner such that a subsequent dosage rate is a predetermined percentage (e.g., at least 5%, 10%, 15%, 25%, and/or combinations thereof) above the immediately previous dosage rate. The predetermined percentage can increase or decrease over time, e.g., depending on the desired fluid therapy and/or patient considerations. Optionally, the diuretic can be provided in a manner that doubles the diuretic dosage rate or total diuretic within a period of time (e.g., 10 minutes, 15 minutes, 20 minutes, or within a range of 10-20 minutes). In other embodiments, however, the dosage determining phase can include one or more time periods during which the diuretic dosage rate does not increase and/or is held substantially constant. The dosage determining phase can continue until the patient's urine output reaches or exceeds a desired threshold rate and/or a predetermined time period has elapsed, at which point the diuretic dosage rate can be adjusted, as described in block 208 below. Additional details regarding administering diuretic to the patient are described with reference to at least FIG. 4A of U.S. Pat. No. 11,357,446, the entirety of which is hereby incorporated herein by reference.

At block 206, the method 200 can optionally include causing a hydration fluid to be provided to the patient at a hydration rate. The hydration fluid can comprise saline and/or other fluids having sodium and can be provided automatically or semi-automatically by a hydration fluid system connected to the patient, such as the hydration system 120 of FIG. 1. The hydration fluid can be provided before, during, and/or after providing the diuretic in block 204 (e.g., before, during, and/or after the dosage determining phase). Intravenous infusion of hydration fluid containing electrolytes (e.g., sodium and/or chloride) can increase diuretic efficiency, which is counterintuitive since a goal of fluid therapy is net removal of fluid. Hydration fluid can also reduce or inhibit intravascular depletion, decreases in cardiac output, and/or decreases in renal perfusion, among other benefits.

In some embodiments, the hydration fluid is provided to the patient based at least in part on the patient's urine output rate, e.g., to drive net fluid loss from the patient. For example, the hydration rate can be less than the urine output rate. In some embodiments, the hydration rate is a percentage of the urine output rate (e.g., 90%, 80%, 70%, 60%, 50%, 40%, 30%, 20%, or 10% of the urine output rate) for a given range of urine output rates (e.g., from 0 ml/hr to 1000 ml/hr). Optionally, the percentage can be higher for certain parts of the range (e.g., for the lower end of the range to reduce the likelihood of hypotension) and/or lower for other parts of the range (e.g., for the higher end of the range to increase net fluid loss). As another example, the hydration rate can substantially match the urine output rate (e.g., 100% of the urine output rate) for an initial amount of urine output by the patient (e.g., at least the initial 150 milliliters (mL), 200 mL, or 250 mL), for an initial time period (e.g., the first hour, 2 hours, or 3 hours), for an initial time period during hydration fluid and/or diuretic dose finding, and/or until the patient's urine output rate reaches a predetermined threshold. Subsequently, the hydration rate can be adjusted to be less than the urine output rate. In a further example, the hydration rate may be determined based on whether the urine output rate is above or below one or more different thresholds, with the difference between the urine output rate and hydration fluid rate increasing as the urine output rate increases. In such embodiments, the difference between the urine output rate and the hydration fluid rate can increase (with the urine rate being higher than the hydration fluid rate) as the urine output rate increases, and thus the net fluid loss from the patient can increase as the urine output rate increases.

At block 208, the method 200 can include adjusting at least one of the dosage rate of the diuretic or the hydration rate of the hydration fluid, thereby causing net fluid loss from the patient. For example, the (i) diuretic dosage rate can be adjusted, (ii) the hydration rate can be adjusted, or (iii) the diuretic dosage rate and the hydration rate can both be adjusted. In some embodiments, the diuretic dosage rate is adjusted after the dosage determining phase of the treatment procedure is complete. As discussed above in block 204, the dosage determining phase can end when (i) a predetermined amount of time has elapsed since the initial diuretic administration, and/or (ii) the urine output rate is or becomes greater than or equal to a predetermined threshold rate. The treatment procedure can then switch to a phase in which the diuretic dosage rate is adjusted to a dosage rate configured to maintain the patient's urine output rate at or above a desired output rate to cause net fluid loss (also known as a "continuous delivery phase" or "fluid reduction phase").

The adjusted diuretic dosage rate can be the initial dosage rate for the fluid reduction phase and can be determined in many different ways. For example, the adjusted diuretic dosage rate can be based on the outcome of the dosage determining phase (e.g., the dosage rate when the patient's urine output reaches or exceeds the target threshold). In representative embodiments, the diuretic dosage rate is decreased, e.g., to maintain the patient's urine output rate at a predetermined rate and/or within a predetermined range (e.g., no more than 5%, 10%, or 20% variability from a predetermined rate). Decreasing the diuretic dosage rate can decrease the rate of increase in urine output rate (e.g., cause the patient's urine output to approach a constant or substantially constant rate) but without actually decreasing the urine output rate itself.

In some embodiments, the adjusted diuretic dosage rate is a predetermined percentage or fraction of the current dosage rate (e.g., the dosage rate at the end of the dosage determining phase) or a predetermined percentage of the cumulative diuretic dosage amount (e.g., the cumulative amount delivered during the dosage determining phase). For example, the adjusted dosage rate can be a predetermined percentage (e.g., 10%, 15%, 20%, 25%, 30%, or within a range of 10-30%) of a value of the total amount of diuretic delivered to the patient at that time. For example, if the total amount delivered is 100 mg, and the predetermined percentage is 25%, then the adjusted dosage rate can be 25 mg/hr. In some embodiments, the percentage used to calculate the adjusted diuretic dosage rate is based on a pharmacokinetic characteristic of the particular diuretic being infused. For example, the percentage can be 20% for furosemide, such that if 50 mg of furosemide is infused in 60 minutes, then the adjusted diuretic dosage rate can be 10 mg/hr.

In some embodiments, block 208 includes delivering the diuretic at the adjusted diuretic dosage rate until the fluid reduction phase is complete, e.g., until a predetermined period of time has elapsed, the patient's urine output drops below a low urine output threshold, and/or until a target net fluid loss volume is achieved. During the fluid reduction phase, the diuretic dosage rate can be constant or substantially constant (e.g., no more than 5%, 10%, or 20% variability from the initially determined adjusted diuretic dosage rate). In other embodiments, however, block 208 can include making additional adjustments to the diuretic dosage rate during the treatment procedure (e.g., increasing and/or decreasing the diuretic dosage rate). The adjustments can be based on whether one or more of a predetermined set of conditions is met, such as whether the urine output rate is too high (e.g., which can indicate that the patient has a high and/or increasing serum level of diuretic). The set of conditions can include (i) an average urine rate being greater than a predetermined rate for a period of time, (ii) an average rate of change of the urine rate being greater than a predetermined rate of change, and/or (iii) a diuretic dosage rate being greater than a predetermined dosage rate. If some (e.g., two) or all of the conditions are met, the diuretic dosage rate can be decreased (e.g., by a predetermined amount or percentage), also referred to herein as "down-titration."

In some embodiments, a down-titration is performed only if all or a majority of the above conditions are met, which can avoid unnecessarily decreasing the diuretic dosage rate, thereby allowing urine output rates to remain high and avoiding unnecessary interruptions to the treatment procedure. For example, whereas other methodologies may interrupt fluid therapy and decrease the diuretic dosage rate (e.g., to zero mg/hr) only when the urine rate too high, the process described herein may only decrease the dosage rate (e.g., to a non-zero or zero dosage rate) when one or more factors are met, such as when the urine output rate is both high and continuing to increase. Stated differently, the process herein can prevent the diuretic dosage rate from being unnecessarily decreased when urine rates are temporarily high (e.g., above the predetermined rate), but are trending downward. This approach can prevent or inhibit over-diuresis, excess fluid loss and/or electrolyte loss, as well limit unnecessary exposure of the patient to additional diuretic. Additionally, because the diuretic dosage rate can be down-titrated, rather than stopping the diuretic entirely, the fluid therapy can continue (albeit at lower urine output rates) without needing to completely restart the procedure.

As another example, the additional adjustments to the diuretic dosage rate in block 208 can include increasing the diuretic dosage rate, also referred to herein as "re-ramping" or "up-titration." In some embodiments, re-ramping is performed if urine output rates are too low, as determined based on a set of conditions. The set of conditions can include (i) the average urine rate being below a predetermined threshold rate for a predetermined period of time, and/or (ii) more than a predetermined amount of debt has accumulated over the predetermined period of time. "Debt" can be defined as the area on a plot between the urine output rate and a set rate (e.g., 325 ml/hr), and can represent how much of and for how long the urine output rate has been below the set rate. If some or all of the conditions are met, re-ramping can be performed by incrementally increasing the diuretic dosage rate until (i) a predetermined amount of time has elapsed, and/or (ii) the urine output rate is or becomes greater than or equal to a predetermined threshold rate. The re-ramp process can be identical or generally similar to the dosage determining process previously described in block 204. In representative embodiments, the dosage rate or "ramp" can start at any dosage identified during the dosage determining process, such as the current dosage rate, a previously determined dosage rate, or another suitable dosage rate (e.g., not at the beginning of the dosage).

The re-ramping process can be performed automatically, semi-automatically, or manually. In some embodiments, re-ramping is a semi-automatic or manual process requiring user approval, e.g., for regulatory and/or safety reasons. In such embodiments, the system can output a notification to the user (e.g., via the display 150 of FIG. 1) instructing the user to confirm that re-ramping should be initiated. Optionally, the system can implement a pre-approval procedure in which the user can allow the system to automatically perform re-ramping under certain conditions (e.g., within a specific time period, until a certain urine output volume and/or rate is achieved, for a maximum diuretic amount and/or dosage rate, and/or combinations thereof). This approach can allow for automatic re-ramping under limited circumstances, which can reduce the amount of human intervention during the treatment procedure and improve the responsiveness of the system to the patient's current state. Once the pre-approval conditions have elapsed, the user may need to provide re-approval before additional automatic re-ramping is allowed.

In some embodiments, block 208 also includes adjusting the diuretic dosage rate in response to a potential and/or detected blockage (e.g., an air lock, a kink in a fluid line, and/or combinations thereof) in the urine collection system. For example, an air lock can be any partial or complete obstruction of fluid flow due to trapped gas (e.g., air) within a fluid system. Air locks may produce an artificial drop in urine output rates, which can affect the determination of the diuretic dosage rate (e.g., result in a diuretic dosage rate that is too high). In some embodiments, the presence of an air lock is detected based on a period of little or no urine output (due to the air lock blocking urine flow), followed by a sudden large bolus of urine output (due to built-up pressure in the fluid line clearing the air lock). When the system detects that an air lock or other blockage was or is present, the system can compensate by adjusting the diuretic dosage rate to the dosage rate that should have been used if the air lock or other blockage had not occurred. The appropriate dosage rate can be determined based on historical data for the patient receiving the fluid therapy and/or one or more other patients (e.g., the diuretic dosage rate before the air lock occurred, a diuretic dosage rate calculated from the patient's urine output rate before the air lock occurred, and/or combinations thereof).

Alternatively, or in combination, block 208 can include adjusting the hydration rate, e.g., by increasing or decreasing the hydration rate based on the patient's urine output rate to drive net fluid loss from the patient. For example, as previously described, the hydration rate can initially match the patient's urine output rate for a set of initial conditions (e.g., certain time period, initial urine output amount, and/or initial urine output rate). Once the initial conditions have elapsed, the hydration rate can be maintained at a rate lower than the urine output rate (e.g., a percentage of the urine output rate) so the patient exhibits net fluid loss during the fluid reduction phase. The hydration rate can be determined in various ways, such as a percentage or fraction of the patient's urine output rate, based on whether the urine output rate is above or below a number of different thresholds (e.g., with the difference between the urine output rate and hydration rate increasing as the urine output rate increases), and/or any other suitable approach.

Optionally, the diuretic dosage rate and/or hydration rate can be adjusted based on factors other than patient's urine output rate. For example, the diuretic dosage rate and/or hydration rate can be adjusted based on the patient's blood pressure in order to avoid placing the patient in a hypotensive state. In some embodiments, if the patient's blood pressure level is too low (e.g., below a threshold value or range), the system can avoid increasing the diuretic dosage rate and/or can decrease the diuretic dosage rate for a certain period of time. Alternatively, or in combination, the system can increase the hydration rate (e.g., to the maximum allowable hydration rate and/or to provide a desired fluid replacement profile (e.g., a 100% match to the patient's urine output rate)) for a certain period of time if low blood pressure levels are detected. The system can also output an alert indicating that the patient's blood pressure level is low so a user can check on the patient's status. Optionally, the system can take both blood pressure levels and urine output rates into account, e.g., the system can generate alerts and/or can adjust the diuretic dosage rate and/or hydration rate if the Patient's blood pressure is low and the patient's urine output rate drops. This approach can improve patient safety and control over the treatment procedure.

In some embodiments, some or all of the blocks of the method 200 are performed as part of a medical procedure for treating the patient for a fluid overload condition. The method 200 can be used as a primary, standalone therapy for treating fluid overload, or can be used in combination with other therapies (e.g., as a post-primary therapy to reduce the likelihood of re-hospitalization). The method 200 can be performed in any suitable setting, such as an inpatient setting or an outpatient setting. In embodiments where the method 200 is performed as an outpatient therapy, the overall duration of the method 200 can be reduced (e.g., to no more than 10 hours, 8 hours, 5 hours, 4 hours, 3 hours, 2 hours, or 1 hour).

The method 200 illustrated in FIG. 2 can be modified in many different ways. For example, any of the blocks of the method 200 can be omitted, such as blocks 204 or 206. In some embodiments, block 204 is omitted so that the method 200 controls hydration fluid infusion but not diuretic delivery, or so that the method 200 does not involve any diuretic delivery at all. Similarly, block 206 can be omitted so that the method 200 controls diuretic delivery but not hydration fluid infusion, or so that the method 200 does not involve any hydration fluid infusion at all. As another example, some or all of the blocks 200 of the method 200 can be performed in a different order and/or repeated (e.g., any of blocks 202, 204, 206, and/or 208). In a further example, the method 200 can optionally include additional blocks not shown in FIG. 2 (e.g., causing delivery of additional medications, obtaining parameters other than urine output rate, and/or combinations thereof).

The present technology can provide many advantages for treating fluid overload and/or managing patient fluid levels. For example, embodiments of the present technology have been shown to consistently reduce the fluid volume in patients faster and safer than conventional treatment systems and methods. For example, whereas conventional methods can typically take at least five days to remove 4-5 L of net fluid volume, embodiments of the present technology have been shown to remove 4-5 L liters of net fluid volume in no more than 24 hours. Additionally, embodiments of the present technology have also been shown to remove significant amounts of salt via high sodium urine from patients. This can reduce the likelihood of the patient reaccumulating fluid after discharge, which can lead to reductions in rehospitalization rates. Moreover, embodiments of the present technology can automatically and continuously monitor urine output, hydration fluid infusion, and/or diuretic delivery to mitigate patient safety concerns (e.g., over-diuresis and/or hypotension) during the treatment procedure.

Embodiments of the present technology can provide various benefits, such as any of the following: (i) optimizing net fluid volume removal; (ii) reducing the time needed to achieve desired net fluid removal by allowing physicians to use higher diuretic dosages and/or dosage rates earlier in treatment compared to conventional treatments; (iii) avoiding or reducing risk of adverse events such as over-diuresis, dehydration, and/or intravascular depletion; (iv) quickly assessing if a patient is diuretic resistant; and (v) providing a record of treatment data. Embodiments of the present technology may obtain an average net fluid removal rate (e.g., average urine output rate minus average hydration fluid infusion rate) of at least 225 ml/hr, which provides 3.4 L per day of net fluid volume removal based on introducing 2 L of fluid per day orally or through IV infusion. This rate of fluid removal, while replacing sodium, may reduce the overall length of stay and/or provide enhanced decongestion.

III. Urine Output Sensing without the Use of an Indwelling Catheter

FIGS. 3A-10 are flowcharts illustrating methods 300, 310, 400, 500, 600, 610, 630, 650, 601, 700, 800, 900, 1000 ("methods 300-1000") for treating a patient in accordance with embodiments of the present technology. One or more of the methods 300-1000 can be used to treat the patient for fluid overload by removing fluid from the patient to produce a negative fluid balance (i.e., net fluid loss). The methods 300-1000 are described herein as a series of process portions, steps, or blocks, individual ones of which can be performed by any embodiment of the systems and devices described herein, such as the system 100 of FIG. 1. All or a subset of the blocks of one or more of the methods 300-1000 can be performed without using an indwelling catheter, such as while the patient is using a non-indwelling catheter or other non-indwelling device configured to obtain urine output from the patient. In some embodiments, at least some blocks of one or more of the methods 300-1000 are performed by a system or device including one or more processors and a memory storing instructions that, when executed by the one or more processors, cause the system or device to perform one or more of the blocks described herein. For example, one or more of the methods 300-1000 can be performed by the controller 140 of the system 100 of FIG. 1, and/or one or more other suitable computing devices/systems. All or a portion of one or more of the methods described herein can be performed on a single processing device, on multiple processing devices, and/or in a networked or cloud computing environment. Optionally, some or all of the blocks of one or more of the methods can performed automatically or semi-automatically, with little or no human intervention. Although at least some methods of the present technology are described with reference to measuring individual inputs of a patient's urine output volume data and, e.g., using those data to determine as estimated or average urine output rate for a patient, those of ordinary skill in the art will appreciate that the methods of the present technology can be based, additionally or alternatively, on measuring individual inputs of sodium excretion data (e.g., the sodium concentration of a given input of urine output volume data) and/or an estimated or average sodium excretion rate determined based at least partially on the individual inputs of sodium excretion data.

Figure 3A:
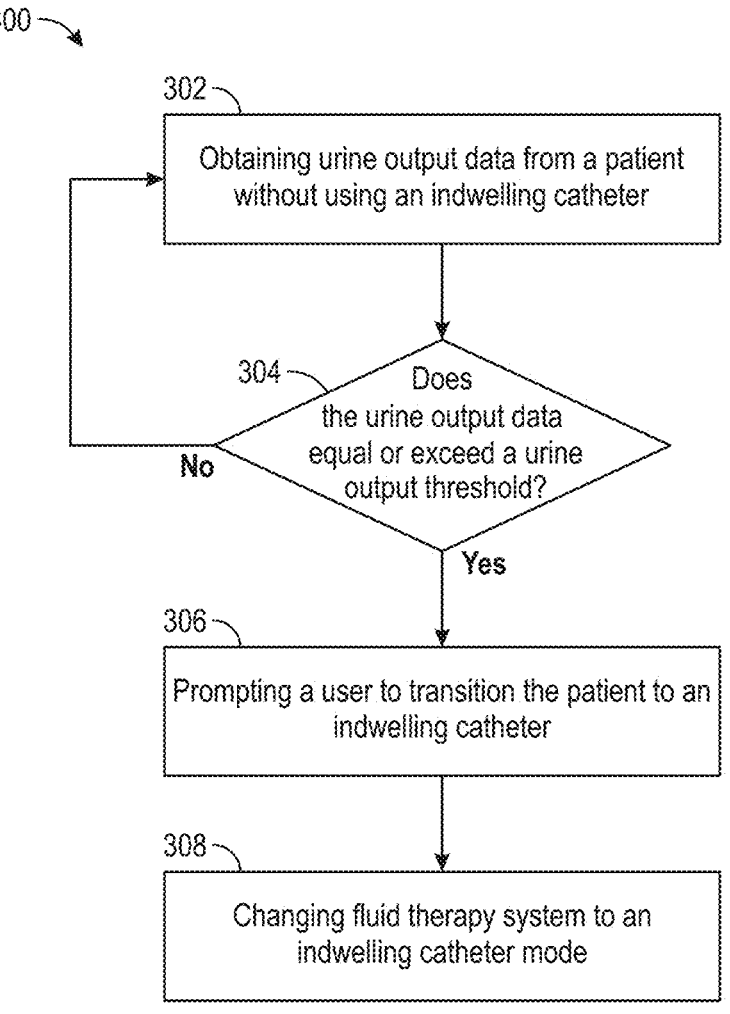

The method 300 of FIG. 3A is generally associated with providing fluid therapy to a patient. The method 300 can be performed by a fluid therapy system (e.g., the system 100) configured to provide fluid therapy to patients with an indwelling catheter and to patients with a non-indwelling catheter. Stated differently, the method 300 can allow a fluid therapy system to provide fluid therapy to patients for which "continuous" or urine output rate data is available (based at least partially on, e.g., urine received via an indwelling catheter) and to patients for which "discontinuous" or urine output volume data is available (based at least partially on, e.g., urine received via a non-indwelling catheter). For example, as set forth below, the method 300 can allow the system 100 to switch between "indwelling" or "Foley" and "non-indwelling" or "no-Foley" modes of operating, e.g., to calibrate the patient's fluid therapy to the specific equipment used by the patient as part of that fluid therapy and/or the urine output data received from the patient during fluid therapy.

The method 300 can begin at block 302 by obtaining urine output data from a patient without using an indwelling catheter. Block 302 can be at least generally similar or identical to block 202 of the method 200 (FIG. 2), but the obtained urine output data can include urine output volume data (e.g., based at least partially on urine obtained via an external or other non-indwelling catheter) instead of urine output rate data (e.g., which is typically based at least partially on urine obtained via an indwelling catheter). The obtained urine output volume data can be discontinuous. For example, individual inputs of the urine output volume data can correspond to urination (voluntary or otherwise) by the patient, and/or individual inputs of the urine output volume data can be obtained no less than a predetermined amount of time (e.g., no less than 1 second, 5 seconds, 10 seconds, 15 seconds, 30 seconds, 1 minute, 5 minutes, 10 minutes, 20 minutes, 30 minutes, 45 minutes, 1 hour, and/or combinations thereof) apart from one another.

In some embodiments, obtaining the urine output data in block 302 includes obtaining an amount of time since one or more prior inputs of urine output volume data were obtained. The amount of time can be, for example, the total time since the patient most recently urinated (voluntarily or otherwise) and/or the time between individual urinations events. The obtained amount of time can be used to calculate or estimate an average urine output rate over the obtained amount of time, e.g., by dividing the obtained urine output volume data by the obtained amount of time. Additionally, or alternatively, a smoothing function, a curve-fitting function, or other suitable algorithms can be applied to the urine output volume data to estimate urine output rate data.

In block 304, the method 300 can include determining whether the obtained urine output data (block 302) equals or exceeds a urine output threshold. Embodiments of the present technology are expected to provide effective fluid therapy and promote net fluid and/or sodium loss from patients that do not use indwelling catheters. However, once a patient's urine output exceeds a certain volume and/or rate, it may be beneficial to transition those patients to an indwelling catheter to improve (e.g., further improve) or even optimize the patient's net fluid and/or sodium loss. The urine output threshold can correspond to urine output volume and/or rate at or beyond which it is beneficial to transition a given patient to an indwelling catheter. For example, the urine output threshold can include a volume of urine output (e.g., a volume of at least 50 mL, 100 mL, 150 mL, 200 mL, 500 mL, and/or combinations thereof up to 1 liter (L), 1.5 L, or 2 L). The volume can be associated with a single bolus, multiple boluses, and/or a volume of urine output over a predetermined time period (e.g., up to 30 minutes, 1 hour, 2 hours, 3 hours, 3 hours, 4 hours, 5 hours, 6 hours, 7 hours, 8 hours, and/or combinations thereof). In these and/or other embodiments, the urine output threshold can include an average rate of urine output, such as an average rate of up to 50 mL/hr, 100 mL/hr, 150 mL/hr, 200 mL/hr, 250 mL/hr, 300 mL/hr, 400 mL/hr, 500 mL/hr, and/or combinations thereof. The average rate of urine output can be an average rate of urine output for the entire duration of the patient's therapy, a subset thereof, or a predetermined time period (e.g., the last 30 minutes, 1 hour, 2 hours, 3 hours, 3 hours, 4 hours, 5 hours, 6 hours, 7 hours, 8 hours, and/or combinations thereof of the patient's therapy). If the urine output data is less than the urine output threshold (block 304, NO), then the method 300 can return to block 302. If the urine output data equals or exceeds the urine output threshold (block 304, YES), the method 300 can include block 306.

At block 306, the method 300 can include prompting a user to transition the patient to an indwelling catheter. The indwelling catheter can include a Foley catheter. Prompting the user to transition the patient to the indwelling catheter can include receiving confirmation from the patient that the patient wishes to use the indwelling catheter. In some embodiments, the urine output data (block 302) is being obtained via a non-indwelling catheter, and block 306 includes replacing the non-indwelling catheter with the indwelling catheter. In some embodiments, block 306 can include receiving confirmation that the patient has been transitioned to the indwelling catheter after, e.g., the user has replaced the patient's non-indwelling catheter with the indwelling catheter.

At block 308, the method 300 can include changing a fluid therapy system to an indwelling catheter mode. For example, prior to block 308, the fluid therapy system can obtain urine output data from the patient (block 302) without using an indwelling catheter and can, accordingly, be operating in a non-indwelling catheter mode, e.g., to account for the inability of the fluid therapy system to accurately measure the patient's instantaneous urine output rate while the patient is not using an indwelling catheter. When the fluid therapy system is in the indwelling catheter mode, the fluid therapy system can be configured to provide fluid therapy in a manner that is at least generally similar to the method 200 described previously with reference to FIG. 2. Once the patient has been transitioned to the indwelling catheter (block 306), however, the fluid therapy system can accurately obtain the patient's instantaneous urine output rate via the indwelling catheter and, accordingly, can be changed to operate in the indwelling catheter mode. Accordingly, in some embodiments, the fluid therapy system can automatically change to the indwelling catheter mode when, for example, the fluid therapy system detects that the obtained urine output data is continuous and/or otherwise associated with urine excretion by the patient's bladder. In these and/or other embodiments, the fluid therapy system can change to the indwelling catheter mode in response to one or more inputs provided by the user. When the fluid therapy system is in the non-indwelling catheter mode, the fluid therapy system can be configured to provide fluid therapy in a manner that is at least generally similar to one or more of the methods 310, 400, 500, 600, 610, 630, 650, 601, 700, 800, 900 described below with reference to FIGS. 3B-9. In some embodiments, block 308 can include receiving an input (e.g., from a user) associated with and/or otherwise informing the system that the patient has been or desires to be transitioned to an indwelling catheter.

Although the method 300 is described with reference to transitioning a patient from a non-indwelling catheter to an indwelling catheter, in other embodiments the patient can be transitioned from an indwelling catheter to a non-indwelling catheter. For example, at the start of fluid therapy, an indwelling (e.g., Foley) catheter can be used unless or until the patient experiences one or more adverse events related to the indwelling catheter (e.g., discomfort, pain, flow blockage, infection, and/or combinations thereof) and, in response to the one or more adverse events, the patient can transition to a non-dwelling catheter. Likewise, although the method 300 is described with reference to transitioning a fluid therapy system from a non-indwelling catheter mode to an indwelling catheter mode, in other embodiments the fluid therapy system can be transitioned from an indwelling catheter mode to a non-indwelling catheter mode. For example, at the start of fluid therapy, the patient can use an indwelling (e.g., Foley) catheter and the fluid therapy system can operate in an indwelling catheter mode unless or until the patient experiences one or more adverse events related to the indwelling catheter (e.g., discomfort, pain, flow blockage, infection, and/or combinations thereof) and, in response to the one or more adverse events, the patient can be transitioned to a non-dwelling catheter and the fluid therapy system can, accordingly, be transitioned to a non-indwelling catheter mode. In these and/or other embodiments, one or more of blocks 302-306 can be omitted and the patient can be transitioned to an indwelling catheter, e.g., in response to a physician's recommendation and/or at the patient's request.

The method 310 of FIG. 3B is generally associated with providing fluid therapy to a patient. At block 312, the method 310 can include obtaining, via one or more sensors, urine output data from the patient. Obtaining the urine output data can include obtaining one or more (e.g., multiple) inputs of urine output volume data. Obtaining the multiple inputs can include obtaining the multiple inputs without utilizing an indwelling catheter. In some embodiments, for example, obtaining the multiple inputs can include obtaining the multiple inputs via an external catheter, such as a condom catheter, a PureWick™ catheter, and/or one or more other non-indwelling catheters.

Obtaining the multiple inputs can include (i) receiving urine from the patient via the external catheter and (ii) obtaining an amount or quantity (e.g., a volume) of the received urine via, e.g., a weight sensor, an in-line flow sensor, a container fill level sensor, and/or one or more other urine measurement devices and/or techniques, including those described herein. In at least some embodiments, for example, obtaining the multiple inputs can include obtaining a first input of urine output volume data from the patient and obtaining a second input of urine output volume data from the patient at least some amount of time (e.g., at least 1 minute, 2 minutes, 5 minutes, 10 minutes, 15 minutes, 30 minutes, 60 minutes, and/or combinations thereof) after obtaining the first input. In some embodiments, third, fourth, fifth, sixth, etc. inputs of urine output volume data can be obtained in an at least generally similar manner to the first and second inputs. Additionally, or alternatively, obtaining the multiple inputs can include obtaining the multiple inputs via one or more sensors.

The one or more sensors used to obtain the urine output data can include an ultrasonic sensor, an MRI sensor, a radar sensor, a CT sensor, an EIT sensor, and/or one or more other suitable sensors including one or more sensors described herein. The one or more sensors can be disposed externally on the patient and at least one of the one or more sensors can be configured to measure a dimension of or otherwise associated with an organ of the patient. For example, at least one of the one or more sensors can be positioned to measure a volume and/or a change in volume of a bladder of the patient, and/or a volume or a change in volume of fluid (e.g., urine) within the bladder.

In some embodiments, obtaining the urine output data (including, e.g., the multiple inputs of urine output volume data) can include obtaining the urine output data via user input. For example, a clinician or nurse can direct the patient the urinate into a container (e.g., a commode specimen collector or "witches hat") and manually input urine output volume data. Additionally, or alternatively, the user can input urine output data to account for leaks, e.g., from an external or other non-indwelling catheter used by the patient. Obtaining the urine output data can include obtaining the urine output data over a time period (e.g., at least the prior 5 minutes, 15 minutes, 30 minutes, 60 minutes, 90 minutes, 120 minutes, 180 minutes, 240 minutes, and/or combinations thereof), in which individual inputs of urine output data are received no less than 10 minutes, 20 minutes, 30 minutes, 40 minutes, or 60 minutes apart from one another. In some embodiments, obtaining the urine output data can include prompting the patient to urinate, e.g., after a predetermined amount of time (e.g., up to 5 minutes, 15 minutes, 30 minutes, 60 minutes, 90 minutes, 120 minutes, 180 minutes, 240 minutes, and/or combinations thereof) has elapsed since the patient's prior urination. Obtaining individual inputs of the urine output data at the above-referenced spaced-apart intervals (i.e., in a non-continuous manner) is different from obtaining urine output rate data in a continuous manner via an indwelling catheter.

In some embodiments, block 312 can include determining an accumulated volume of urine output based at least partially on the obtained urine output data (e.g., the obtained multiple inputs of urine output data). The accumulated volume of urine output can refer to the sum of discrete individual inputs each obtained at different times. In this regard, the individual inputs are volumetric and/or do not correspond to a urine output rate. Moreover, in at least some embodiments, the accumulated volume does not include and/or is not based on inputs obtained on a continuous basis (e.g., inputs obtained less than once per minute) and/or using an indwelling catheter. Determining the accumulated volume of urine output can include adding individual inputs of the obtained urine output data together, determining the accumulated volume over a time period (e.g., at least the prior 5 minutes, 15 minutes, 30 minutes, 60 minutes, 90 minutes, 120 minutes, 180 minutes, 240 minutes, and/or combinations thereof), and/or determining an average or assumed urine output rate over the time period based on individual inputs of volumetric urine output data. To determine an average or assumed urine output rate over a time period, a urine output rate can be determined by considering the individual inputs of volumetric urine output data and the amount of time elapsed since the last input of volumetric urine output data obtained. For example, the urine output rate of 1000 mL/hr can be determined for an input of 500 mL received 30 minutes after the last input. The determined rate can be utilized by the system as an assumed steady rate over the given time period. In some embodiments, the multiple inputs over the time period can be added together and divided by an amount of time (e.g., in hours) associated with the time period.

In some embodiments, block 312 can include (i) using an indwelling (e.g., Foley) catheter for at least one portion or phase of the fluid therapy and (ii) using a non-indwelling (e.g., condom) catheter for one or more other portions or phases of the fluid therapy. For example, in at least some embodiments the patient uses an indwelling catheter during the diuretic dose finding portion of the fluid therapy and, once the diuretic dose finding portion is completed, the patient can switch to using a non-indwelling catheter. While the patient makes use of the indwelling catheter, the fluid therapy provided to the patient can be based at least partially on urine received (e.g., excreted) from the patient via the indwelling catheter, including any urine output rate measurements based thereon. Once the patient switches to using a non-indwelling catheter, the fluid therapy provided to the patient can be based at least partially on urine received (e.g., urinated) from the patient via the non-indwelling catheter as described elsewhere herein.

At block 314, the method 310 can include causing a diuretic to be provided to the patient at a diuretic dosage rate. Block 314 can be at least generally similar to block 204 of the method 200 (FIG. 2), but the diuretic dosage rate can be based on the obtained urine output volume data (block 312) rather than a urine output rate. Additional details regarding causing the diuretic to be provided based urine output volume data are described elsewhere herein, including with reference to at least the method 400 of FIG. 4.

At block 316, the method 310 can include causing a hydration fluid to be provided to the patient at a hydration rate. Block 316 can be at least generally similar to block 206 of the method 200 (FIG. 2), but the hydration rate can be based on the obtained urine output volume data (block 312) rather than a urine output rate. Additional details regarding causing the hydration fluid to be provided based on urine output volume data are described elsewhere herein, including with reference to at least the method 500 of FIG. 5.

At block 318, the method 310 can include adjusting at least one of the dosage rate of the diuretic or the hydration rate of the hydration fluid, thereby causing net fluid loss from the patient. Block 318 can be at least generally similar to block 208 of the method 200 (FIG. 2). For example, the dosage rate and/or the hydration rate can be associated with a diuretic dose finding portion, a hydration fluid replacement portion, a diuretic escalation portion, a therapy escalation portion, a therapy stopping portion, and/or a down titration portion of the patient's fluid therapy, and adjusting at least one of the dosage rate or the hydration rate can include adjusting the dosage rate and/or the hydration rate associated with one or more of the diuretic dose finding portion, the hydration fluid replacement portion, the diuretic escalation portion, the therapy escalation portion, the therapy stopping portion, and/or the down titration portion. Additional details regarding adjusting the dosage rate of the diuretic and/or the hydration rate of the hydration fluid are described elsewhere herein, including with reference to one or more of the methods 400-1000 of FIGS. 4-10.

In some embodiments, some or all of the blocks of the method 310 are performed as part of a medical procedure for treating the patient for a fluid overload condition. The method 310 can be used as a primary, standalone therapy for treating fluid overload, or can be used in combination with other therapies (e.g., as a post-primary therapy to reduce the likelihood of re-hospitalization). The method 310 can be performed in any suitable setting, such as an inpatient setting or an outpatient setting. In embodiments where the method 310 is performed as an outpatient therapy, the overall duration of the method 310 can be reduced (e.g., to no more than 10 hours, 8 hours, 5 hours, 4 hours, 3 hours, 2 hours, or 1 hour). For example, during outpatient therapy, the method 300 can include causing an initial infusion or bolus of diuretic (e.g., 200 mg) to be administered to the patient, followed by a continuous infusion of diuretic at a rate (20 mg/hr) based on the initial infusion, such as described previously herein with reference to FIGS. 1 and 2. Diuretic administration can be stopped at some time (e.g., three hours) before the end (e.g., the scheduled end) of fluid therapy, and the response time of the patient (e.g., the amount and/or dosage rate of diuretic administered to the patient when the patient's urine output equals or is greater than a urine output threshold) can be used to determine an outpatient diuretic dosage for the patient.

One or more blocks 312-318 of the method 310 can be performed while the patient is awake and/or while the patient is sleeping. As set forth above, patients are generally not expected to urinate during sleep. Accordingly, to facilitate obtaining the multiple inputs while the patient is asleep, the method 310 can include waking the patient, or prompting a user to wake the patient, at least one during the night and instructing the patient to urinate. In other embodiments, one or more blocks 312-318 of the method 310 can be paused during night-time hours and/or when the patient is asleep. For example, a fluid therapy system, such as the system 100 (FIG. 1) can be placed in a "night mode" in which the fluid therapy system is configured to obtain multiple inputs of urine output volume data (block 312) and/or determine an accumulated volume of urine output (block 312), but does not adjust the fluid therapy (block 318) unless or until the fluid therapy system is no longer in the night mode. In some embodiments, the fluid therapy system can reduce or halt diuretic administration while the patient is asleep. This can reduce the likelihood that the patient is roused from sleep by the urge to urinate and is expected to make the patient more comfortable during the night and/or better-rested the following morning. The fluid therapy system can initiate the reduction/halt in diuretic administration when the fluid therapy system is placed in night mode, during a time period associated with the patient's sleeping hours, in response to one or more inputs associated with the patient being asleep, and/or combinations thereof.

Figure 4:
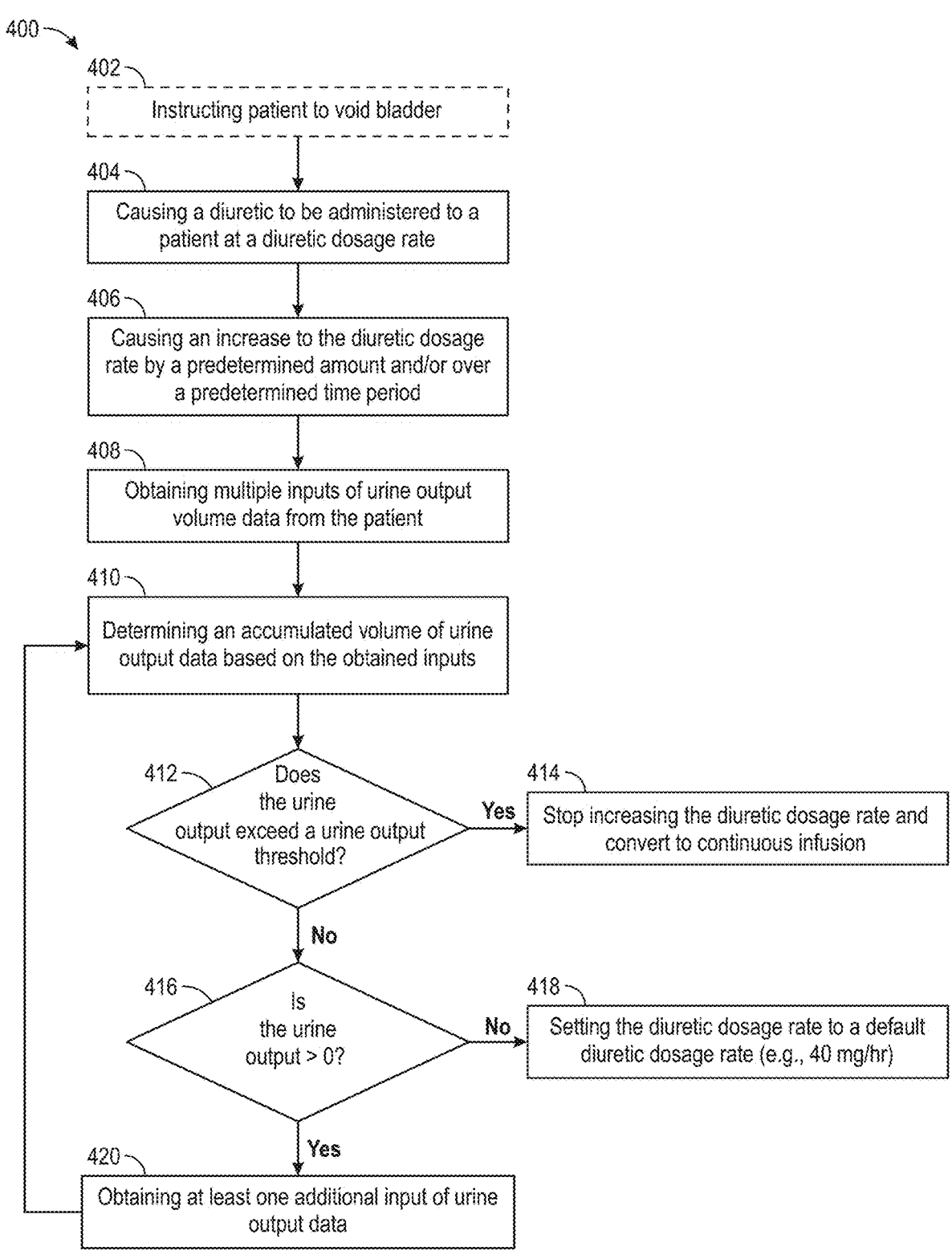
FIG. 4 is a block diagram illustrating a diuretic dose finding method, in accordance with embodiments of the present technology.

FIG. 4 is a block diagram illustrating a method 400 for diuretic dose finding for a patient, in accordance with embodiments of the present technology. At block 402, the method 400 can include instructing the patient to void their bladder. Instructing the patient to void their bladder (and, e.g., the patient following said instruction) is expected to increase the accuracy of later-obtained urine output data, e.g., by expelling previously-accumulated urine from the patient's bladder such that the later-obtained urine output data reflects urine output after the start of fluid therapy. However, block 402 is optional and can be omitted. In some embodiments, for example, rather than instructing the patient to void their bladder, the patient can be instructed to urinate normally (e.g., at will, voluntarily, in response to an urge to do so, etc.) and/or no instruction regarding urination can be provided to the patient.

At block 404, the method 400 can include causing a diuretic to be administered to the patient at a diuretic dosage rate. The diuretic dosage rate can be an initial dosage rate, as described previously herein, including with reference to at least block 204 of the method 200 (FIG. 2).

At block 406, the method can include causing an increase to the diuretic dosage rate. Causing the increase can include causing the diuretic dosage rate to increase by a predetermined amount and/or over a predetermined time period, such as by "ramping" the diuretic dosage rate as described previously herein, including with reference to at least block 204 of the method 200 (FIG. 2). For example, after the diuretic has been administered at the initial diuretic dosage rate (block 404), the initial dosage rate can then be gradually increased (e.g., "ramped"), e.g., to elicit an increase in the patient's urine output rate. The predetermined time period can be a duration of minutes or hours. For example, the predetermined time period can be up to 10 minutes, up to 20 minutes, up to 2 hours, up to 4 hours, or longer. For patients that elect not to use an indwelling catheter, it is expected to take longer to observe a response to the diuretic (e.g., increased urine output) compared to patients that elect to use an indwelling catheter. Accordingly, increasing the time period over which the diuretic dosage rate is increased is expected to provide more data regarding the patient's urine output (e.g., by allowing more time for the patient to voluntarily urinate) which, in turn, is expected to increase the accuracy of the urine output data for the patient.

In some embodiments, causing the increase to the diuretic dosage rate can include causing the increase in multiple discrete steps and providing the diuretic at a continuous rate after one or more of the discrete steps. The patient can be instructed to void their bladder prior to the start of one or more of the discrete steps.

In some embodiments, causing the increase to the diuretic dosage rate can include causing a percentage of an administered dosage of the diuretic to be provided to the patient. The percentage can be associated with the continuous infusion phase, as described herein (e.g., with reference to block 414). For example, if 100 mg of a diuretic have been administered to the patient and the percentage is 20%, block 406 can include causing 20 mg/hr of diuretic to be administered to the patient, e.g., as or in addition to the increase to the diuretic dosage rate.

At block 408, the method 400 can include obtaining multiple inputs of urine output volume data from the patient. Block 408 can be at least generally similar to block 312 of the method 310 (FIG. 3B). For example, obtaining the multiple inputs can include obtaining the multiple inputs without using an indwelling catheter, such as via an external catheter, including a condom catheter or a PureWick™ catheter. In some embodiments, obtaining the multiple inputs can include obtaining the multiple inputs during the predetermined time period (block 406), e.g., while causing the increase to the diuretic dosage rate (block 406).

At block 410, the method 400 can include determining an accumulated volume of urine output data based on the obtained multiple inputs (block 408). Block 410 can be at least generally similar to block 312 of the method 310 (FIG. 3B).

At block 412, the method 400 can include determining whether the accumulated volume of urine output (block 410) exceeds (or is equal to) a urine output threshold (e.g., at least 50 milliliters, 100 mL, 150 mL, 200 mL, 500 mL, and/or combinations thereof up to 1 liter (L), 1.5 L, or 2 L). In some embodiments, the urine output threshold can be a urine output rate, such as 525 ml/hr or another suitable urine output rate. Accordingly, determining whether the accumulated volume of urine output exceeds the urine output rate can include determining, based on the accumulated volume of urine output (block 410) and an amount of time that has elapsed, an estimated urine output rate of the patient. For example, if the patient has an accumulated volume of urine output of 1050 mL over a 2 hour time period, block 412 can include determining that the patient's urine output rate over the 2 hour time period was 525 mL/hr, equal to the urine output threshold. If the accumulated volume of urine output exceeds (or is equal to) the urine output threshold (block 412, YES), the method 400 can include block 414. If not (block 412, NO), the method 400 can include block 416.

At block 414, the method 400 can include stopping the increase to the diuretic dosage rate and converting to continuous infusion, e.g., by causing the diuretic to be administered at a continuous dosage rate. Converting to continuous infusion can be at least generally similar to initiating the continuous delivery or fluid reduction phases described previously herein, including with reference to FIG. 2. For example, during continuous infusion, a continuous (e.g., non-increasing or non-ramping) dosage rate of diuretic can be administered to the patient to maintain the patient's urine output rate at or above a desired output rate to cause net fluid loss. In some embodiments, the continuous dosage rate can be based, at least in part, on a value of the diuretic provided to the patient when the patient's urine output exceeded (or equaled) the urine output threshold. For example, if the urine output threshold includes a volume of urine, then the continuous dosage rate can be equal to or a percentage of the diuretic dosage rate administered to the patient when the urine output equaled or exceeded the volume of urine. For example, if the patient has an accumulated volume of urine output of 1050 mL over a 2 hour time period, the continuous dosage rate can be equal to or a percentage of the diuretic dosage rate administered to the patient 2 hours ago. Similarly, if the urine output threshold includes a urine output rate threshold, then the continuous dosage rate can be equal to or a percentage of the diuretic dosage rate administered to the patient at an estimated time when the patient's urine output rate equaled or exceeded the urine output rate threshold. For example, if the patient has a determined (e.g., average) output rate over a 2 hour time period of 525 mL/hr, the continuous dosage rate can be equal to or a percentage of the diuretic dosage rate administered to the patient 2 hours ago.

At block 416, the method 400 can include determining whether the accumulated volume of urine output (block 410) is greater than zero. If no (block 416, NO), the method 400 can include block 418. If yes (block 416, YES), the method 400 can include block 420.

At block 418, the method 400 can include setting the diuretic dosage rate to a default diuretic dosage rate. The default diuretic dosage rate can be up to 40 mg/hr, or one or more other suitable diuretic dosage rates, including other diuretic dosage rates described herein.

At block 420, the method 400 can include obtaining at least one additional input of urine output data. The at least one additional input of urine output data can be obtained using any of the techniques described previously herein, including in a manner at least generally similar to block 408. After obtaining the at least one additional input of urine output data, the method 400 can return to block 410 and determine an accumulated volume of urine output data based on the obtained inputs of urine output data (blocks 408 and 420) and/or repeat one or more other blocks (e.g., blocks 412 and 416) of the method 400.

Figure 5:
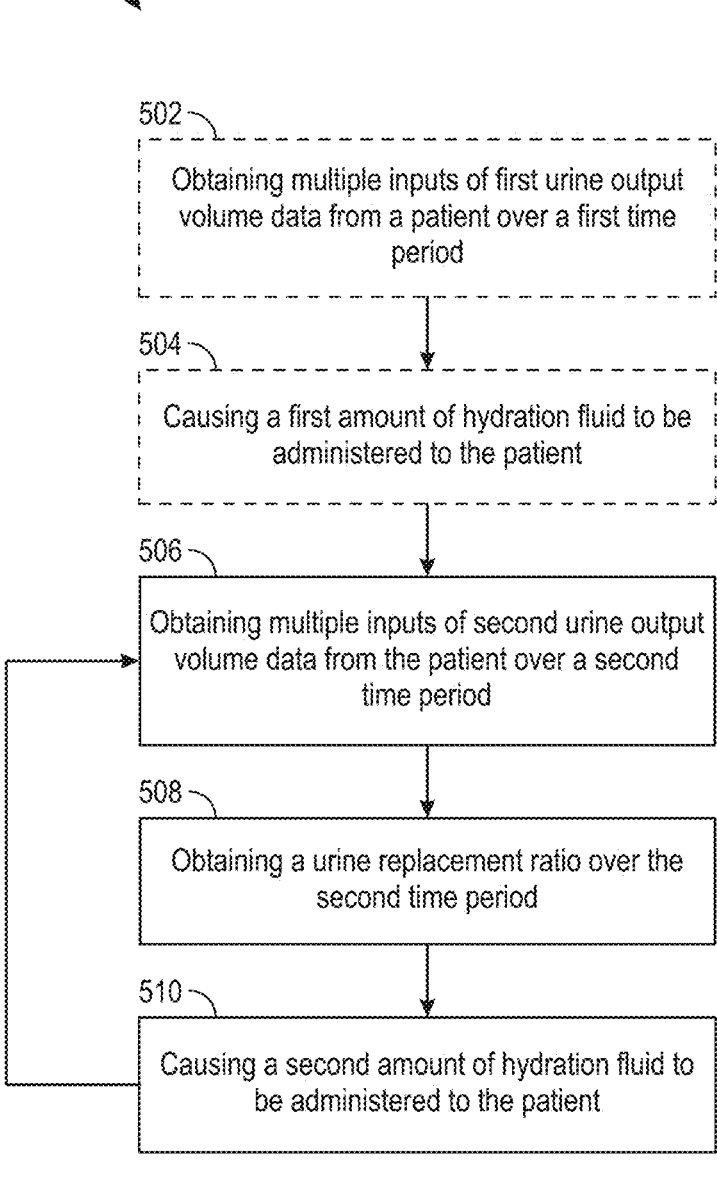
FIG. 5 is a block diagram illustrating a method associated with providing hydration fluid to a patient, in accordance with embodiments of the present technology.

FIG. 5 is a block diagram illustrating a method 500 associated with providing hydration fluid to a patient, in accordance with embodiments of the present technology. At block 502, the method 500 can include obtaining multiple inputs of first urine output volume data from the patient over a first time period. Block 502 can be at least generally similar to block 312 of the method 300 (FIG. 3B). In some embodiments, if individual inputs of the multiple inputs include a volume greater than 1 L, the method 500 can include providing a prompt or recommendation to transition the patient to an indwelling catheter and/or to stop providing fluid therapy. Fluid therapy may be less effective for patients that are retaining large volumes of fluid (e.g., as indicated by urinations greater than 1 L). Transitioning these patients to an indwelling catheter can provide more data and/or more accurate data about these patients' urine output which, as a result, can improve their response to fluid therapy. If these patients refuse the indwelling catheter, stopping fluid therapy can reduce the likelihood of, or prevent entirely, side effects associated with patient overhydration.

At block 504, the method 500 can include causing a first amount of hydration fluid to be administered to the patient. The first amount can be equal to or less than a total urine output volume during the first time period (block 502), e.g., up to a hydration fluid threshold. In some embodiments, for example, causing the first amount of hydration fluid to be administered to the patient can include replacing a volume of urine output by the patient during a time period of 2 hours and/or up to a hydration fluid threshold of 250 mL. In other embodiments, the time period can be up to 10 minutes, 20 minutes, 30 minutes, 1 hour, 1.5 hours, 2 hours, 2.5 hours, 5 hours, and/or combinations thereof, and/or the hydration fluid threshold can be at least 25 mL, 50 mL, 100 mL, 200 mL, 250 mL, 500 mL, e.g., up to 1 L, 1.5 L, 2 L, 3 L, and/or combinations thereof. Additionally, or alternatively, causing the first amount of hydration fluid to be administered to the patient can include causing an amount of hydration fluid equaling a urine output volume of a first input of the multiple inputs (block 502) to be administered to the patient. This amount can correspond to the patient's initial bladder void and subsequent voids by the patient can be used for administering the hydration fluid during the first time period, e.g., up to a hydration fluid threshold.

At block 506, the method 500 can include obtaining multiple inputs of second urine output data over a second time period. Block 506 can be at least generally similar to block 312 of the method 300 (FIG. 3B) and/or block 502. Obtaining the multiple inputs of second urine output data can include obtaining the multiple inputs during and/or after causing the first amount of hydration fluid to be administered to the patient (block 504). However, in at least some embodiments, blocks 502 and/or 504 can be omitted and the second time period can be an initial time period and/or the multiple inputs of second urine output data can be initial urine output data for the patient. In some embodiments, obtaining the multiple inputs can include estimating a urine rate of the patient based on the obtained multiple inputs. For example, each of the multiple inputs can correspond to the patient voiding their bladder, and the volume of urine received from the patient during multiple voids and the amount of time between individual voids can be used to determine an average urine rate of the patient.

At block 508, the method 500 can include obtaining a urine replacement ratio over the second time period (block 506). The urine replacement ratio can correspond to an amount or average rate of urine excreted by the patient during the second time period, and/or can be a percentage of the second urine output volume data. In one specific example, if the patient's second urine output volume data over the second time period (e.g., the past hour) amounts to an average urine rate of 425 mL/hr, the urine replacement ratio can be 47%, e.g., so that an amount of hydration fluid equal to about 47% of the patient's urine output over the time period (i.e., about 200 mL/hr over the next hour) is infused into the patient. Generally, as the patient's urine output (e.g., urine output rate) increases, the hydration rate can increase as well, but at a rate less than that of the urine output rate, e.g., to decrease the patient's net fluid balance (e.g., so that the net fluid balance becomes more negative) and/or increase the patient's net fluid loss. Accordingly, the urine replacement ratio can vary based on the second urine output volume data (block 506), e.g., to produce a desired net fluid loss from the patient.

At block 510, the method 500 can include causing a second amount of hydration fluid to be administered to the patient. The second amount can be based, at least in part, on the urine replacement ratio. For example, the second amount of hydration fluid can be a percentage (e.g., corresponding to the urine replacement ratio in block 508) of an amount of urine excreted by the patient over the time second period and can be infused into the patient at a rate that is equal to, or substantially equal to, the rate at which the patient excreted that urine. In other embodiments, the amount of hydration fluid infused into the patient can equal, or substantially equal, the amount of urine the patient excreted during the second time period, but the hydration fluid can be administered at a high rate (e.g., a maximum allowable infusion rate, such as up to 500 mL/hr) over a time period less than the second time period. The hydration fluid can be administered at this high rate until the amount administered is equal to, or is substantially equal to, the amount of urine the patient excreted during the second time period. For example, if the patient excreted 425 mL of urine over the past hour, the system would determine that the patient should receive 200 mL of hydration fluid, and causing the second amount of hydration fluid to be administered to the patient can include causing the hydration fluid to be administered at a rate of 500 mL/hr for 24 minutes, resulting in 200 mL of hydration fluid being administered to the patient. In at least some embodiments, the second amount of hydration fluid is infused only in response to measured or obtained urine output during the second time period.

In some embodiments, the amount of hydration fluid infused into the patient can decrease as the patient's urine output increases. For example, if the patient's urine output is below a first threshold (e.g., 175 ml/hr, 225 ml/hr, 275 ml/hr, or within a range of 175-275 ml/hr), the amount of hydration fluid administered to the patient may be zero, or a minimum amount (e.g., 10 ml/hr), e.g., to keep the vein pressurized and open (referred to as a Keep Vein Open (KVO) rate). While the urine output is below the first threshold, rehydration is less or not necessary and, because a general goal of fluid therapy is to maximize net fluid removal, no infusion of hydration fluid may be provided when the urine output is below the first threshold. As previously described, in some embodiments, the hydration fluid rate may match the urine output for a first period of time or until a minimum amount of hydration fluid is infused.

If the patient's urine output is between the first threshold and a second threshold (e.g., 225, 375 ml/hr, 425 ml/hr, 500 ml/hr, or within a range of 225-500 ml/hr), substantially all (e.g., at least 90% or 100%) of the urine volume (i.e., between the first and second thresholds) can be replaced by hydration fluid, e.g., to ensure the kidneys are getting enough fluid and salt, and/or to inhibit a hypotensive state (e.g., if the lower range is 225 ml/hr, and the urine rate is 325 ml/hr, 100 ml of saline will be infused).

If the patient's urine output is between the second threshold and a third threshold (e.g., 975 ml/hr, 1025 ml/hr, 1100 ml/hr, or within a range of 975-1100 ml/hr), substantially all (e.g., at least 90% or 100%) of the urine volume between the first and second thresholds can be replaced by hydration fluid, and 40%, 45%, 50%, or a range of 40-50% of the urine volume above the second threshold is replaced. By replacing only a portion of the urine output above the second threshold, net fluid balance as well as net sodium balance can be decreased. Urine typically has less sodium concentration than blood or normal saline, which is approximately 154 mmol/L. As such, replacing urine with an equal amount of hydration fluid may result in increased and undesirable sodium levels. In some embodiments, providing saline or hydration fluid at a rate of more than 50% of the urine output can increase the risk of giving them more sodium than they are releasing. Accordingly, limiting the hydration fluid rate to 50% can protect patients having low sodium urine, while also enabling patients having higher sodium urine to experience faster net fluid and sodium removal. Urine output above the second threshold can serve as an indication that the kidneys are functioning well and not in a hypotensive state, and so the reduced hydration fluid rate is more acceptable.

If the patient's urine output is above the third threshold, substantially all (e.g., at least 90% or 100%) of the urine volume between the first and second thresholds can be replaced by hydration fluid, 40%, 45%, 50%, or a range of 40-50% of the urine volume between the second and third thresholds can be replaced, and none of the urine volume in the fourth region (IV) above the third threshold is replaced. In doing so, the net fluid balance can be further decreased.

Figure 6A:
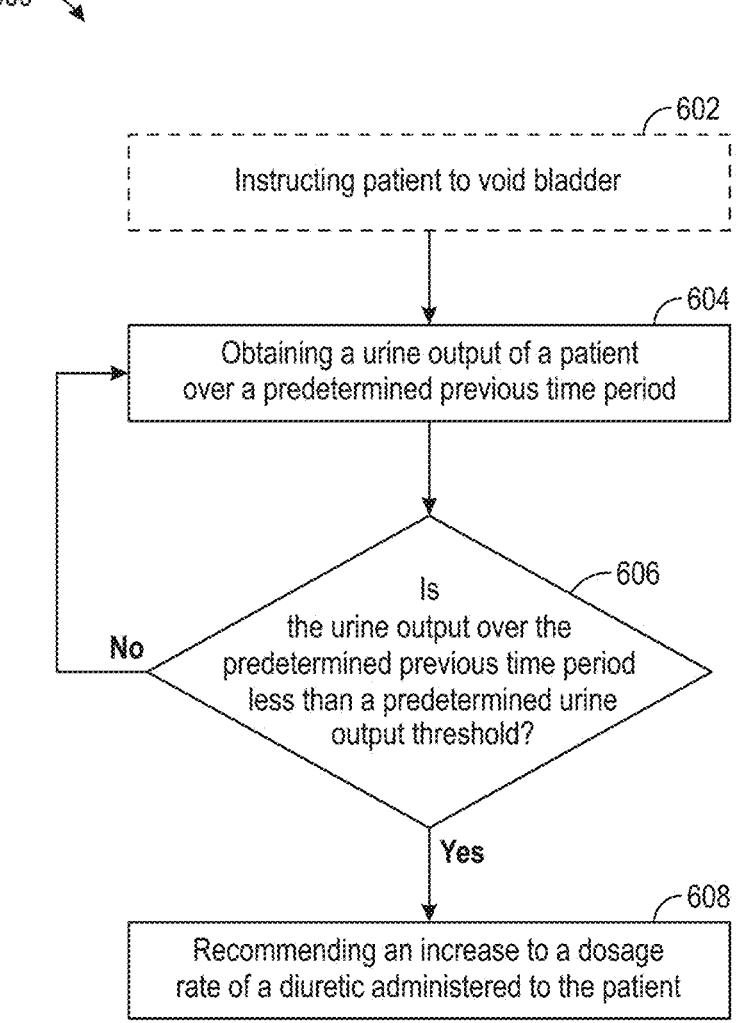
FIGS. 6A-6E are block diagrams illustrating methods associated with administering diuretic to a patient, in accordance with embodiments of the present technology.

FIG. 6A is a block diagram illustrating a method 600 associated with increasing a patient's diuretic dosage, in accordance with embodiments of the present technology. At block 602, the method 600 can include instructing the patient to void their bladder. By voiding their bladder, the patient can expel urine accumulated within the bladder which is expected to increase the accuracy of later-obtained urine output data, e.g., by removing previously-accumulated urine such that the later-obtained urine output data reflects urine output after the start of fluid therapy. However, block 602 is optional and can be omitted. In some embodiments, rather than instructing the patient to void their bladder, the patient can be instructed to urinate normally (e.g., at will, voluntarily, in response to an urge to do so, etc.) and/or no instruction regarding urination can be provided to the patient.

At block 604, the method 600 can include obtaining a urine output of the patient over a predetermined previous time period. Obtaining the urine output can include obtaining multiple inputs of urine output volume data, as described previously herein, e.g., with reference to block 312 of the method 310 (FIG. 3B). The predetermined previous time period can be up to 10 minutes, 20 minutes, 30 minutes, 1 hour, 1.5 hours, 2 hours, 2.5 hours, 5 hours, and/or combinations thereof.

At block 606, the method 600 can include determining whether the obtained urine output over the predetermined previous time period (block 604) is less than a predetermined urine output threshold. In some embodiments, determining whether the obtained urine output is less than the predetermined urine output threshold includes determines whether an obtained urine output volume is less than a predetermined urine output volume threshold. For example, the predetermined urine output threshold can include a volume of at least 300 milliliters (mL), 400 mL, 500 mL, and/or combinations thereof up to 975 mL, 1 liter (L), 1.3 L, 1.5 L, 2 L, or another suitable volume. In some embodiments, the predetermined urine output threshold includes a volume associated with a target urine rate over the predetermined previous time period. For example, the target urine rate can be 325 mL/hr and, if the predetermined previous time period is 3 hours, the predetermined urine output threshold can be 975 mL, i.e., the volume of urine output by a patient with a urine rate of 325 mL/hr over a three hour time period. In other embodiments, the target urine rate can be up to 200 mL/hr, 300 mL/hr, 400 mL/hr, 500 mL/hr, or another suitable target urine rate. If the urine output over the predetermined previous time period is less than the predetermined urine output threshold (block 606, YES), the method 600 can include block 608. If not (block 606, NO), the method 600 can return to block 604 and/or repeat block 604 and/or block 606.

At block 608, the method 600 can include recommending an increase to a dosage rate of a diuretic administered to the patient. In some embodiments, recommending the increase to the diuretic dosage rate can include ramping or re-ramping the diuretic dosage, as described previously herein with reference to at least the method 200 (FIG. 2). In some embodiments, the recommendation can cause a fluid therapy system, such as the system 100 (FIG. 1) to automatically increase the diuretic dosage rate. In these and/or other embodiments, recommending the increase to the diuretic dosage rate can include prompting a user (e.g., a clinician, a nurse, a practitioner, etc.) to increase the diuretic dosage rate. In some embodiments, recommending the increase to the diuretic dosage rate can include a recommendation or instruction that the patient should void their bladder prior to initiating the increase to the diuretic dosage rate. The volume of urine output during the void can be used to confirm that determination in block 606, e.g., that the patient's urine output is less than the predetermined threshold.

Figure 6B:
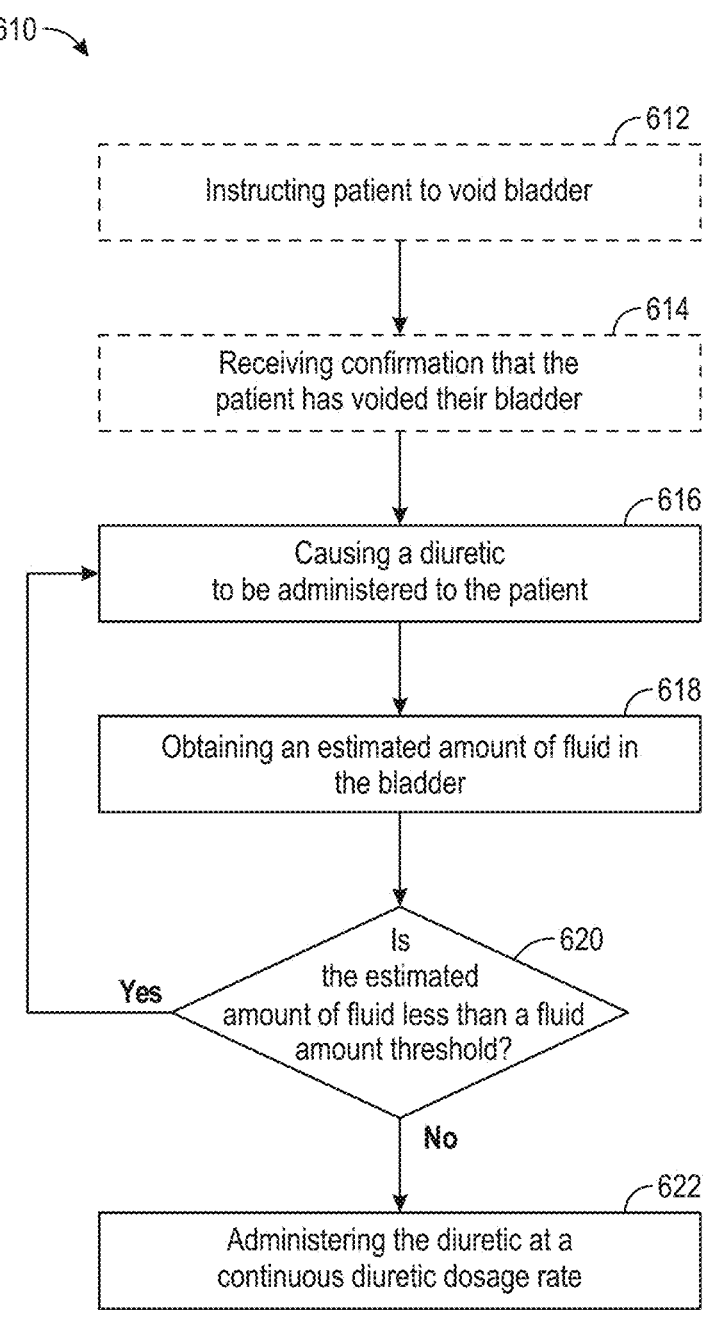

FIG. 6B is a block diagram illustrating a method 610 associated with increasing a patient's diuretic dosage, in accordance with embodiments of the present technology. At block 612, the method 610 can include instructing the patient to void their bladder. By voiding their bladder, the patient can expel urine accumulated within the bladder which is expected to increase the accuracy of later-obtained urine output data, e.g., by removing previously-accumulated urine such that the later-obtained urine output data reflects urine output after the start of fluid therapy. However, block 612 is optional and can be omitted. In some embodiments, rather than instructing the patient to void their bladder, the patient can be instructed to urinate normally (e.g., at will, voluntarily, in response to an urge to do so, etc.) and/or no instruction regarding urination can be provided to the patient.

At block 614, the method 610 can include receiving confirmation that the patient has voided their bladder. Receiving confirming that the patient has voided their bladder can include prompting a user to measure a volume of the patient's bladder and/or a volume of fluid within the patient's bladder, e.g., to confirm that the patient has in fact voided their bladder. The volume of the patient's bladder can be measured using ultrasound, a CT scan, an MRI scan, and/or one or more other volume measurement methodologies. Receiving the confirmation can confirm that the patient's bladder is, e.g., empty, which as noted above is expected to increase the accuracy of subsequent urine output data. Block 614 is optional and can be omitted.

At block 616, the method 610 can include causing a diuretic to be administered to the patient. In some embodiments, causing the diuretic to be administered can include causing the diuretic to be administered at an increasing or ramping diuretic dosage rate, as described previously herein, at least with reference to block 204 of the method 200 (FIG. 2).

At block 618, the method 610 can include obtaining an estimated amount of fluid in the patient's bladder. Obtaining the estimated amount of fluid can include obtaining the estimated amount of fluid via one or more sensors. For example, one or more sensors can be disposed external to the patient's bladder and used to determine a volume or a change in volume of the bladder, and/or a volume of urine and/or a change in volume of urine within the bladder. The sensors can include one or more of the sensors described previously herein, such as an ultrasound sensor, a CT sensor, an MRI sensor, and/or one or more other suitable sensors. In some embodiments, obtaining the estimated amount of fluid can include receiving an estimated amount of fluid provided by a clinician or other user.

At block 620, the method 610 can include determining whether the estimated amount of fluid in the bladder is less than a fluid amount threshold. The fluid amount threshold can be at least 100 mL, 150 mL, 200 mL, 250 mL, 300 mL, and/or combinations thereof up to 600 mL, or another volume of fluid associated with the patient's bladder being full or substantially full. If the estimated amount of fluid is less than the fluid amount threshold (block 620, YES), the method 610 can return to block 616 and/or continue causing diuretic to be administered the patient. If not (block 620, NO), the method 610 can include block 622.

At block 622, the method 610 can include administering the diuretic at a continuous diuretic dosage rate. Administering the diuretic at the continuous diuretic dosage rate can be at least generally similar to administering the diuretic during the continuous delivery phase or fluid reduction phase described previously herein.

Figure 6C:
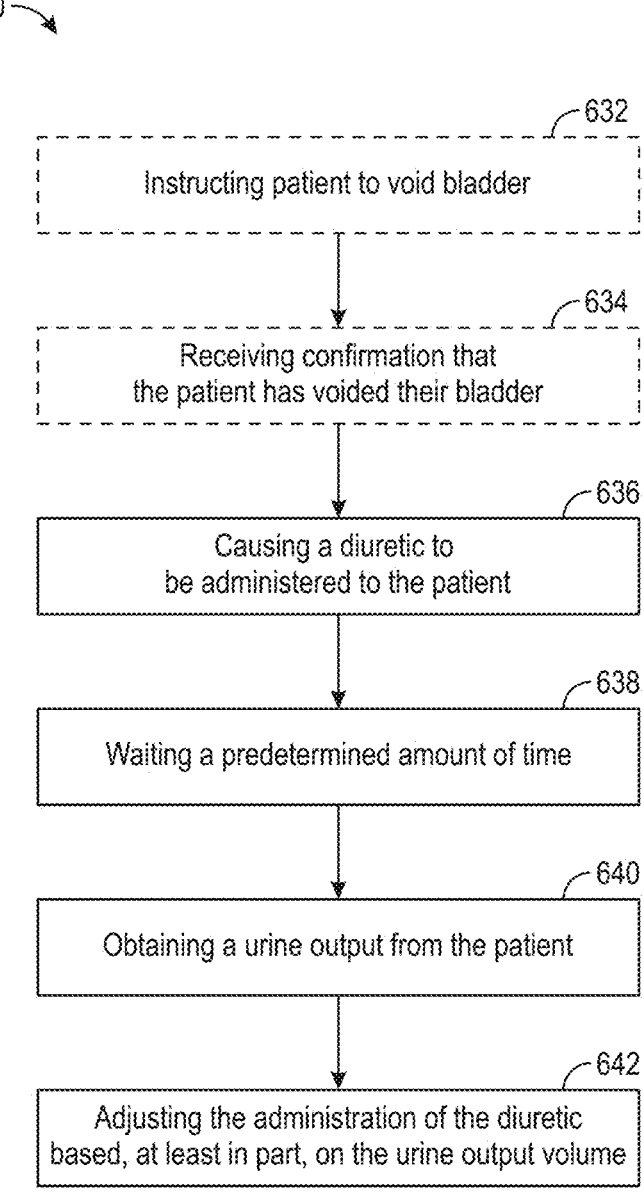

FIG. 6C is a block diagram illustrating a method 630 associated with increasing a patient's diuretic dosage, in accordance with embodiments of the present technology. At block 632, the method 630 can include instructing the patient to void their bladder. By voiding their bladder, the patient can expel urine accumulated within the bladder which is expected to increase the accuracy of later-obtained urine output data, e.g., by removing previously-accumulated urine such that the later-obtained urine output data reflects urine output after the start of fluid therapy. However, block 632 is optional and can be omitted. In some embodiments, rather than instructing the patient to void their bladder, the patient can be instructed to urinate normally (e.g., at will, voluntarily, in response to an urge to do so, etc.) and/or no instruction regarding urination can be provided to the patient.

At block 634, the method 630 can include receiving confirmation that the patient has voided their bladder. Receiving confirming that the patient has voided their bladder can include prompting a user to measure a volume of the patient's bladder and/or a volume of fluid within the patient's bladder, e.g., to confirm that the patient has in fact voided their bladder. Receiving the confirmation can confirm that the patient's bladder is, e.g., empty, which as noted above is expected to increase the accuracy of subsequent urine output data. Block 634 is optional and can be omitted.

At block 636, the method 630 can include causing a diuretic to be administered to the patient. In some embodiments, causing the diuretic to be administered to the patient can include causing a bolus dose of diuretic to be administered to the patient, such as a bolus dose of up to 50 mg, 100 mg, 150 mg, 200 mg, 250 mg, or another suitable diuretic dosage. In these and/or other embodiments, block 636 can be at least generally similar to block 204 of the method 200 (FIG. 2). For example, in some embodiments causing the diuretic to be administered can include causing the diuretic to be administered at an increasing or ramping diuretic dosage rate, e.g., before, during, after, and/or instead of administering one or more bolus doses.

At block 638, the method 630 can include waiting a predetermined amount of time. The predetermined amount of time can be at least 10 minutes, at least 20 minutes, at least 30 minutes, at least 1 hour, at least 2 hours, and/or combinations thereof, up to 5 hours, 6 hours, 7 hours, 8 hours, or 12 hours. In some embodiments, waiting the predetermined amount of time can include instructing the patient to avoid urinating for at least the predetermined amount of time. Block 638 is optional and can be omitted.

At block 640, the method 630 can include obtaining a urine output of the patient. Obtaining the urine output can include instructing the patient to void their bladder after the predetermined amount of time (block 638) and measuring a volume of urine received from the patient. Additionally, or alternatively, obtaining the urine output can include waiting for the patient to voluntarily urinate and/or obtaining an amount of time between the predetermined amount of time (block 638) and the patient's voluntary urination. The amount of time between the predetermined amount of time (block 638) and the patient's voluntary urination can be used to determine an average urine output rate since the patient's prior urination (e.g., blocks 632 and 634). The urine output can include a urine output rate obtained via one or more sensors configured to measure a volume or a change in volume of the patient's bladder, as described elsewhere herein.

At block 642, the method 630 can include adjusting the administration of the diuretic based, at least in part, on the urine output of the patient. In some embodiments, adjusting the administration of the diuretic includes transitioning from a ramped diuretic delivery to a continuous diuretic dosage. The continuous diuretic dosage can be determined based, at least in part, on the obtained urine output, as described elsewhere herein.

Figure 6D:
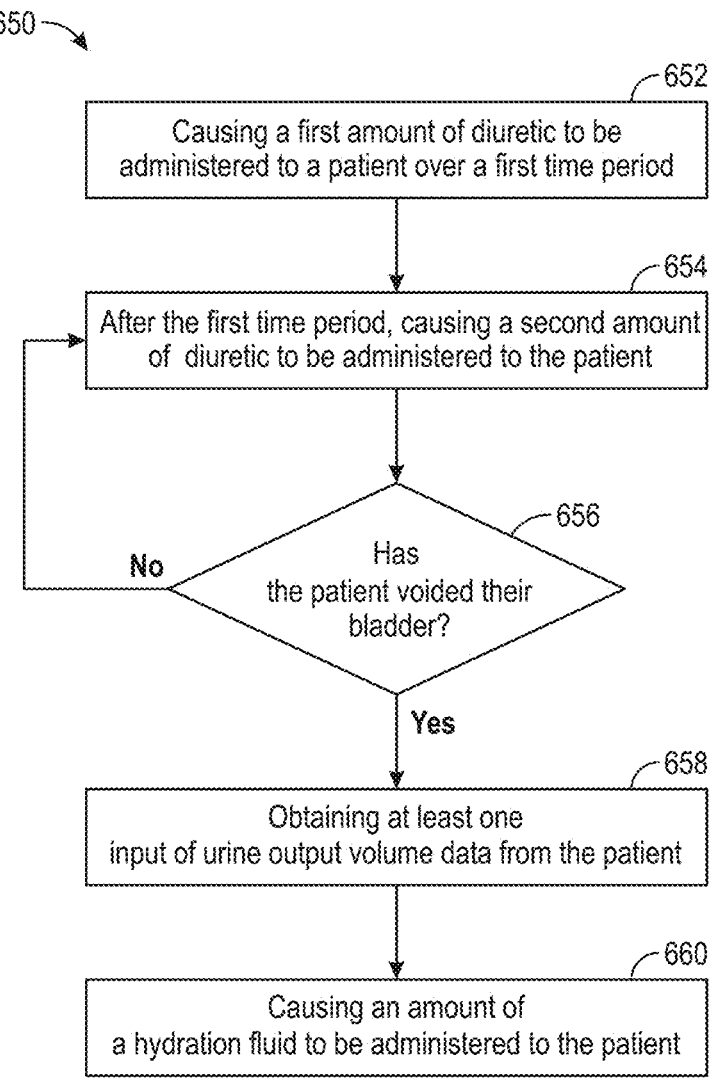

FIG. 6D is a block diagram illustrating a method 650 associated with increasing a patient's diuretic dosage, in accordance with embodiments of the present technology. At block 652, the method 650 can include causing a first amount of diuretic to be administered to a patient. The first amount can be a bolus dose of, for example, up to 50 mg, 100 mg, 150 mg, 200 mg, and/or combinations thereof. In some embodiments, the first amount can be administered over a first time period, such as up to 10 minutes, 20 minutes, 30 minutes, 1 hour, 2 hours, 4 hours, and/or combinations thereof.

At block 654, the method 650 can include causing a second amount of diuretic to be administered to the patient. The second amount can be administered to the patient after administering (e.g., completing the administration of) the first amount of the diuretic (block 652). In some embodiments, the second amount can be a predetermined amount, e.g., not based on the patient's urine output. For example, in at least some embodiments the second amount can be a continuous diuretic dosage rate of 40 mg/hr, a bolus dose, or another suitable diuretic dosage. The diuretic associated with block 654 can be the same as or different than the diuretic associated with block 652.

At block 656, the method 650 can include determining whether the patient has voided their bladder. Determining whether the patient has voided their bladder can include, for example, receiving urine output data via one or more sensors indicating that the patient has or is currently voiding their bladder. If the patient has voided their bladder (block 656, YES), the method 650 can include block 658. If not (block 656, NO), the method can return to block 654 and/or continue to cause the second amount of diuretic to be administered to the patient.

At block 658, the method 650 can include obtaining at least one input of urine output data from the patient. Block 658 can be at least generally similar to block 312 of the method 300 (FIG. 3B).

At block 660, the method can include causing an amount of a hydration fluid to be administered to the patient. The amount can be based, at least in part, on the obtained urine output data (block 658). For example, the urine output data can include a volume of urine and the amount of the hydration fluid can equal, or be some percentage (e.g., up to 50%, 60%, 70%, 80%, 90%, 95%, and/or combinations thereof) of, the volume of urine. The amount of the hydration fluid can be administered continuously or intermittently (e.g., as one or more bolus doses). In some embodiments, the amount administered can be less than the amount that would be administered to the patient if the patient were using an indwelling (e.g., Foley) catheter.

Figure 6E:
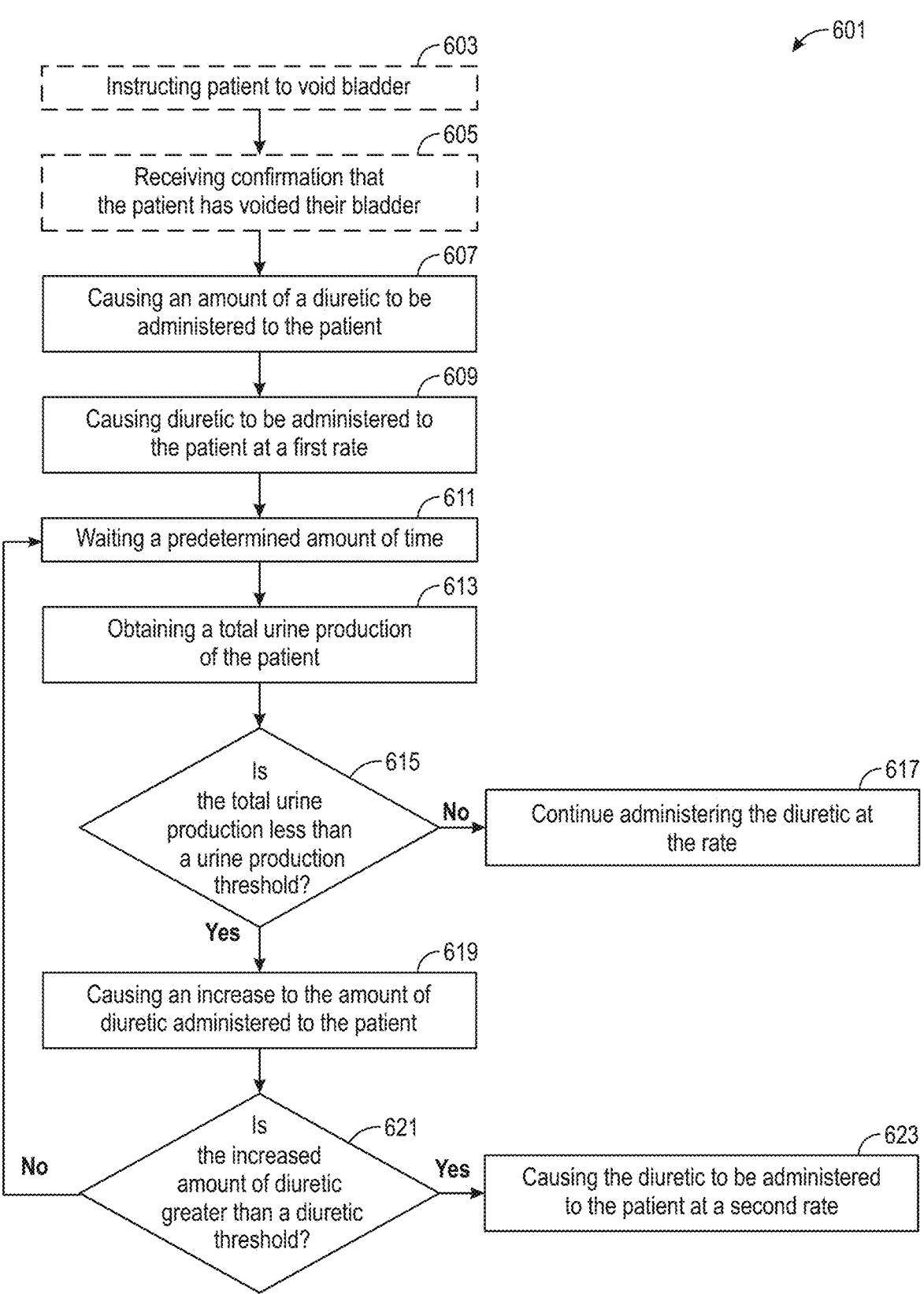

FIG. 6E is a block diagram illustrating a method 601 associated with increasing a patient's diuretic dosage, in accordance with embodiments of the present technology. At block 603, the method 601 can include instructing the patient to void their bladder. By voiding their bladder, the patient can expel urine accumulated within the bladder which is expected to increase the accuracy of later-obtained urine output data, e.g., by removing previously-accumulated urine such that the later-obtained urine output data reflects urine output after the start of fluid therapy. However, block 603 is optional and can be omitted. In some embodiments, rather than instructing the patient to void their bladder, the patient can be instructed to urinate normally (e.g., at will, voluntarily, in response to an urge to do so, etc.) and/or no instruction regarding urination can be provided to the patient.

At block 605, the method 601 can include receiving confirmation that the patient has voided their bladder. Receiving confirming that the patient has voided their bladder can include prompting a user to measure a volume of the patient's bladder and/or a volume of fluid within the patient's bladder, e.g., to confirm that the patient has in fact voided their bladder. Receiving the confirmation can confirm that the patient's bladder is, e.g., empty, which as noted above is expected to increase the accuracy of subsequent urine output data. Block 605 is optional and can be omitted.

At block 607, the method 601 can include causing an amount of a diuretic to be administered to the patient. Causing the amount of the diuretic to be administered can include causing a bolus dose of the diuretic to be administered to the patient. The bolus dose can be, for example, up to 5 mg, 10 mg, 15 mg, 20 mg, 25 mg, 30 mg, 35 mg, 40 mg, 50 mg, 100, mg, 150 mg, 200 mg, and/or combinations thereof. Causing the amount of the diuretic to be administered can be include causing the amount of the diuretic to be administered over a predetermined time period, such as up to 1 second, 5 seconds, 10 seconds, 15 seconds, 30 seconds, 1 minute, 5 minutes, 15 minutes, 30 minutes, 1 hour, and/or combinations thereof.

At block 609, the method 601 can include causing a diuretic (e.g., the same or different diuretic than in block 607) to be administered to the patient at a first diuretic dosage rate. The diuretic dosage rate can be based, at least in part, on the administered amount of diuretic (block 607). For example, the diuretic dosage rate can be based on a percentage of the administered amount of diuretic (block 607), such as a rate that administers up to 5%, 10%, 15%, 20%, 25%, 30%, 40%, 50%, 60%, 70%, 80%, 90%, 95%, or 100% of the administered amount of diuretic over a predetermined time period (e.g., up to 1 hour, 2 hours, 4 hours, and/or combinations thereof). In one particular example, if the administered amount of diuretic (block 607) was 20 mg, the diuretic dosage rate can be 5 mg/hr, 10 mg/hr, 15 mg/hr, 20 mg/hr, 30 mg/hr, or 40 mg/hr. In at least some embodiments, the diuretic dosage rate can be a continuous diuretic dosage rate, e.g., associated with the continuous delivery phase or fluid reduction phase described previously herein.

At block 611, the method 601 can include waiting (or prompting a user to wait) a predetermined amount of time. The predetermined amount of time can be up to 5 minutes, 10 minutes, 15 minutes, 30 minutes, 1 hour, 2 hours, 4 hours, and/or combinations thereof. In some embodiment, block 611 can be at least generally similar to block 638 of the method 630 (FIG. 6C). Block 611 is optional and can be omitted.

At block 613, the method 601 can include obtaining a total urine production of the patient. Obtaining the total urine production can include obtaining the total urine production after the predetermined amount of time (block 611). Block 613 can be at least generally similar to block 618 of the method 610 (FIG. 6B) and can include, e.g., obtaining the estimated amount of fluid via one or more sensors. For example, one or more sensors can be disposed external to the patient's bladder and used to determine a volume or a change in volume of the bladder, and/or a volume of urine and/or a change in volume of urine within the bladder. The sensors can include one or more of the sensors described previously herein, such as an ultrasound sensor, a CT sensor, an MRI sensor, and/or one or more other suitable sensors. Additionally, or alternatively, obtaining the total urine production can include measuring a volume of urine collected in the collection container 112 (FIG. 1) and/or otherwise removed from the patient, such as described previously herein, at least with reference to block 312 of the method 310 (FIG. 3B).

At block 615, the method 601 can include determining whether the total urine production (block 613) is less than a urine production threshold. The urine production threshold can be a urine volume of up to 50 mL, 100 mL, 150 mL, 200 mL, 250 mL, 300 mL, 400 mL, 500 mL, 600 mL, or another volume of fluid associated with the patient's bladder being full or substantially full. If the total urine production is less than the urine production threshold (block 615, YES), the method 601 can include block 619. If not (block 615, NO), the method can include block 617.

At block 617, the method 601 can include continuing to cause the diuretic to be administered at the diuretic dosage rate (block 609). In some embodiments, continuing to cause the diuretic to be administered at the diuretic dosage rate is at least generally similar to transitioning to the continuous delivery phase or fluid reduction phase described previously herein.

At block 619, the method 601 can include causing an increase to the amount of the diuretic administered to the patient. In some embodiments, causing the increase can include causing another bolus dose of diuretic to be administered to the patient. This second bolus dose can be at least generally similar to the initial bolus dose (block 607), or some percentage (e.g., up to 10%, 20%, 30%, 40%, 50%, 60%, 70%, 80%, 90%, 100%, 200%, and/or combinations thereof) greater or less than one or more previous bolus doses. Additionally, or alternatively, causing the increase can include causing an increase to the diuretic dosage rate (block 609), for example, by ramping the diuretic dosage rate as described previously herein.

At block 621, the method 601 can include determining whether the increased amount of diuretic is greater than a diuretic threshold. The diuretic threshold can be a maximum diuretic bolus dose, such as a bolus dose of up to 50 mg, 100 mg, 150 mg, 200 mg, 250 mg, 300 mg, 350 mg, 400 mg, and/or combinations thereof. If the increased amount of diuretic is greater than the diuretic threshold (block 621, YES), the method 601 can include block 623. If not (block 621, NO), the method 601 can continue causing the diuretic to be administered to the patient, e.g., at the increased diuretic dosage rate (block 619) and return to block 611.

At block 623, the method 601 can include causing the diuretic to be administered to the patient at a second diuretic dosage rate. The second diuretic dosage rate can be based, at least in part, on the threshold amount of diuretic (block 621). For example, the second diuretic dosage rate can be associated with the continuous delivery phase or fluid reduction phase described previously herein and can based on a percentage of the threshold amount of diuretic, e.g., a percentage of the maximum diuretic bolus dose.

In some embodiments, the method 601 can include causing hydration fluid to be delivered to the patient, e.g., during one or more of the blocks 603-623. Causing the hydration fluid to be delivered to the patient can include causing hydration fluid to be delivered after detecting urine output (e.g., an increase in urine within the collection container 112) from the patient. The hydration fluid can be administered at a hydration fluid rate configured to allow constant hydration fluid infusion between the patient's bladder voids. In some embodiments, causing the hydration fluid to be delivered to the patient includes causing the hydration fluid to be administered based, at least in part, on a urine replacement ratio as described previously with reference to FIG. 5.

FIG. 7 is a block diagram illustrating a method 700 associated with escalating a patient's fluid therapy, in accordance with embodiments of the present technology. At block 702, the method can include instructing the patient to void their bladder. By voiding their bladder, the patient can expel urine accumulated within the bladder which is expected to increase the accuracy of later-obtained urine output data, e.g., by removing previously-accumulated urine such that the later-obtained urine output data reflects urine output after the start of fluid therapy. However, block 702 is optional and can be omitted. In some embodiments, rather than instructing the patient to void their bladder, the patient can be instructed to urinate normally (e.g., at will, voluntarily, in response to an urge to do so, etc.) and/or no instruction regarding urination can be provided to the patient.

At block 704, the method 700 can include obtaining (i) multiple inputs of urine output volume data from a patient over a time period, (ii) a dosage rate of a diuretic administered to the patient, (iii) an amount of net fluid removed from the patient, and/or (iv) an amount of estimated excess volume to be removed from the patient. Obtaining the multiple inputs can be at least generally similar to block 312 of the method 310 (FIG. 3B). The predetermined time period can be a duration of minutes or hours, such as up to 10 minutes, up to 20 minutes, up to 30 minutes, up to 1 hour, up to 2 hours, up to 4 hours, or longer. The dosage rate can be a continuous dosage rate, e.g., associated with the continuous delivery phase or fluid reduction phase described previously herein. The amount of net fluid removed from the patient can be based, at least in part, on the multiple inputs and an amount of hydration fluid delivered to the patient. The amount of estimated excess volume to be removed from the patient can be based, at least in part, on the amount of net fluid removed and/or a target fluid removal volume for the patient.

At block 706, the method 700 can include determining whether (i) the urine output volume data over the time period is less than a urine output threshold, (ii) the dosage rate of the diuretic is less than a dosage rate threshold, (iii) the amount of net fluid removed is less than a percent estimated excess volume threshold, and/or (iv) the amount of estimated excess volume to be removed is greater than an excess fluid threshold. The urine output threshold can include a volume of urine, such as at least 300 mL, 400 mL, 500 mL, and/or combinations thereof up to 975 mL, 1 L, 1.3 L, 1.5 L, 2 L, or another suitable volume. The dosage rate threshold can up to 10 mg/hr, 20 mg/hr, 30 mg/hr, 40 mg/hr, 50 mg/hr, and/or combinations thereof. The percent estimated excess volume threshold can be based, at least in part, on the amount of net fluid removed and a target fluid removal volume for the patient, e.g., the proportion of the target fluid removal volume that the amount of net fluid removed represents. The excess fluid threshold can be an amount of fluid still expected to be removed from the patient, such as up to 500 mL, 1 L, 1.5 L, and/or combinations thereof. If all or a subset of (i)-(iv) are true (block 706, YES), the method 700 can include block 708. If all of (i)-(iv) are not true (block 706, NO), the method 700 can return to block 704 and/or repeat one or more other blocks of the method 700.

At block 708, the method 700 can include recommending an increase to the dosage rate of the diuretic and/or to an infusion rate of a hydration fluid administered to the patient. Block 708 can be at least generally similar to block 208 of the method 200 (FIG. 2) and/or block 608 of the method 600 (FIG. 6A). In some embodiments, recommending the increase to the diuretic dosage rate can include ramping or re-ramping the diuretic dosage, as described previously herein with reference to at least the method 200 (FIG. 2). In some embodiments, recommending the increase to the hydration fluid infusion rate can include increasing a matching percentage associated with the hydration fluid infusion rate. In some embodiments, the recommendation can cause a fluid therapy system, such as the system 100 (FIG. 1) to automatically increase or otherwise adjust the diuretic dosage rate and/or the hydration fluid infusion rate. In these and/or other embodiments, recommending the increase can include prompting a user (e.g., a clinician, a nurse, a practitioner, etc.) to increase the diuretic dosage rate and/or the hydration fluid infusion rate. In some embodiments, recommending the increase can include a recommendation or instruction that the patient should void their bladder prior to initiating the increase. The volume of urine output during the void can be used to confirm the determination in block 706.

Figure 8:
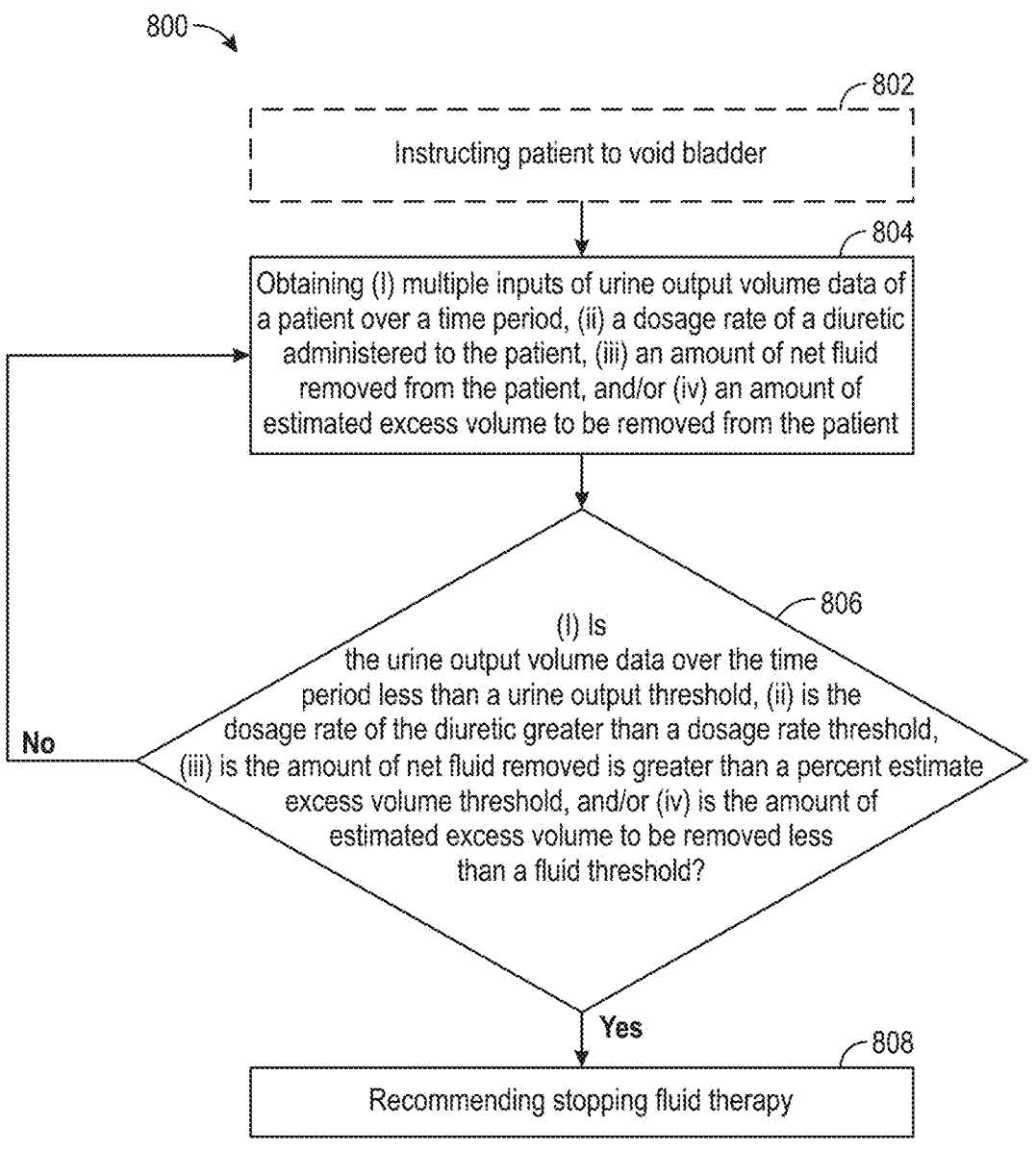
FIG. 8 is a block diagram illustrating a method associated with stopping a patient's fluid therapy, in accordance with embodiments of the present technology.

FIG. 8 is a block diagram illustrating a method 800 associated with stopping a patient's fluid therapy, in accordance with embodiments of the present technology. At block 802, the method 800 can include instructing the patient to void their bladder. By voiding their bladder, the patient can expel urine accumulated within the bladder which is expected to increase the accuracy of later-obtained urine output data, e.g., by removing previously-accumulated urine such that the later-obtained urine output data reflects urine output after the start of fluid therapy. However, block 802 is optional and can be omitted. In some embodiments, rather than instructing the patient to void their bladder, the patient can be instructed to urinate normally (e.g., at will, voluntarily, in response to an urge to do so, etc.) and/or no instruction regarding urination can be provided to the patient.

At block 804, the method 800 can include obtaining (i) multiple inputs of urine output volume data from a patient over a time period, (ii) a dosage rate of a diuretic administered to the patient, (iii) an amount of net fluid removed from the patient, and/or (iv) an amount of estimated excess volume to be removed from the patient. Block 804 can be at least generally similar to block 704 of the method (FIG. 7).

At block 806, the method 800 can include determining whether (i) the urine output volume data over the time period is less than a urine output threshold, (ii) the dosage rate of the diuretic is greater than a dosage rate threshold, (iii) the amount of net fluid removed is greater than a percent estimated excess volume threshold, and/or (iv) the amount of estimated excess volume to be removed is less than an excess fluid threshold. The urine output threshold, the dosage rate threshold, The percent estimated excess volume threshold and/or the excess fluid threshold can be at least generally similar to the correspondingly-named thresholds described previously with reference to block 706 of the method 700 (FIG. 7). If all or a subset of (i)-(iv) are true (block 806, YES), the method 800 can include block 808. If all of (i)-(iv) are not true (block 806, NO), the method 800 can return to block 804 and/or repeat one or more other blocks of the method 800.

At block 808, the method 800 can include recommending stopping the patient's fluid therapy. In some embodiments, the recommendation can cause a fluid therapy system, such as the system 100 (FIG. 1) to automatically stop the patient's fluid therapy. In these and/or other embodiments, recommending to stop the patient's fluid therapy can include prompting a user (e.g., a clinician, a nurse, a practitioner, etc.) to stop the patient's fluid therapy. If the user does not respond to the prompt within a predetermined amount of time (e.g., up to 10 minutes, 20 minutes, 30 minutes, 1 hour, 2 hours, and/or combinations thereof), block 808 can include automatically causing the fluid therapy system to stop the patient's fluid therapy.

Figure 9:
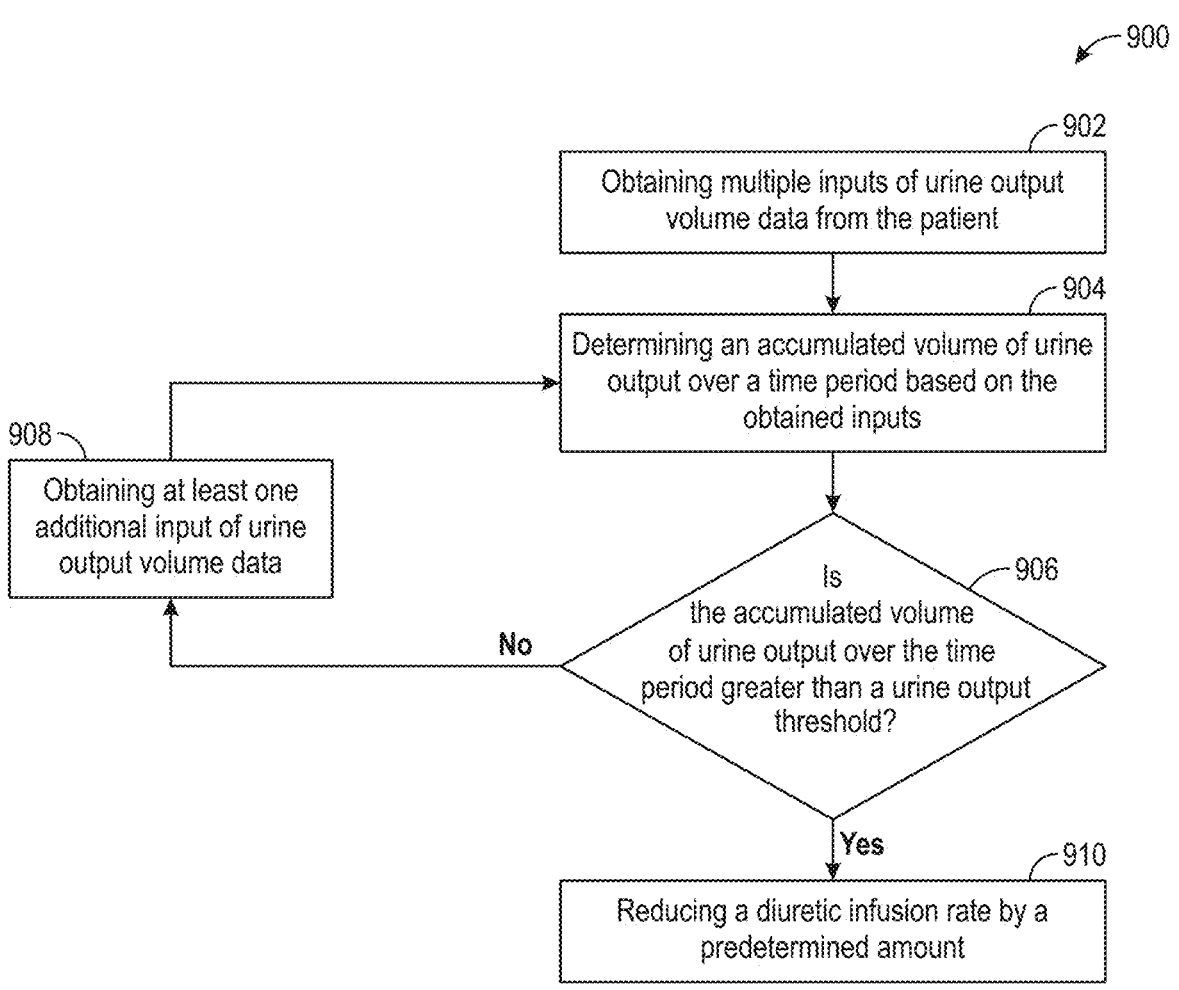
FIG. 9 is a block diagram illustrating a method associated with down-titrating a patient's fluid therapy, in accordance with embodiments of the present technology.

FIG. 9 illustrates a method 900 associated with down-titrating a patient's fluid therapy, in accordance with embodiments of the present technology. At block 902, the method 900 can include obtaining multiple inputs of urine output volume data from the patient. Block 902 can be at least generally similar to block 312 of the method 310 (FIG. 3B).

At block 904, the method 900 can include determining an accumulated volume of urine output over a time period based on the multiple inputs (block 902). Block 904 can be at least generally similar to block 314 of the method 310 (FIG. 3B). The time period can be up to 1 hr, 2 hrs, 3 hrs, 4 hrs, and/or combinations thereof.

At block 906, the method 900 can include determining whether the accumulated volume of urine output over the time period (block 904) is greater than a urine output threshold. The urine output threshold can include a volume of urine (e.g., up to 100 mL, 200 mL, 300 mL, 325 mL, 500 mL, 650 mL, 975 mL, 1 L, 1.3 L, 1.5 L, 2 L, and/or combinations thereof). If the accumulated volume of urine output over the time period is greater than the urine output threshold (block 906, YES), the method 900 can include block 910. If not (block 906, NO), the method can include block 908.

At block 908, the method 900 can include obtaining at least one additional input of urine output volume data. Block 908 can be at least generally similar to block 902. After obtaining the at least one additional input of urine output volume data, the method 900 can include determining an accumulated volume of urine output based on the obtained inputs (e.g., the multiple inputs in block 902 and the at least one additional input in block 908) and/or repeating one or more other blocks of the method 900.

At block 910, the method 900 can include reducing a diuretic infusion rate by a predetermined amount. The predetermined amount can be a percentage of the current diuretic infusion rate, such as up to 10%, 20%, 25%, 30%, 40%, 50%, 60%, 70%, 75%, 80%, 90%, or 100% of the current diuretic infusion rate.

Figure 10:
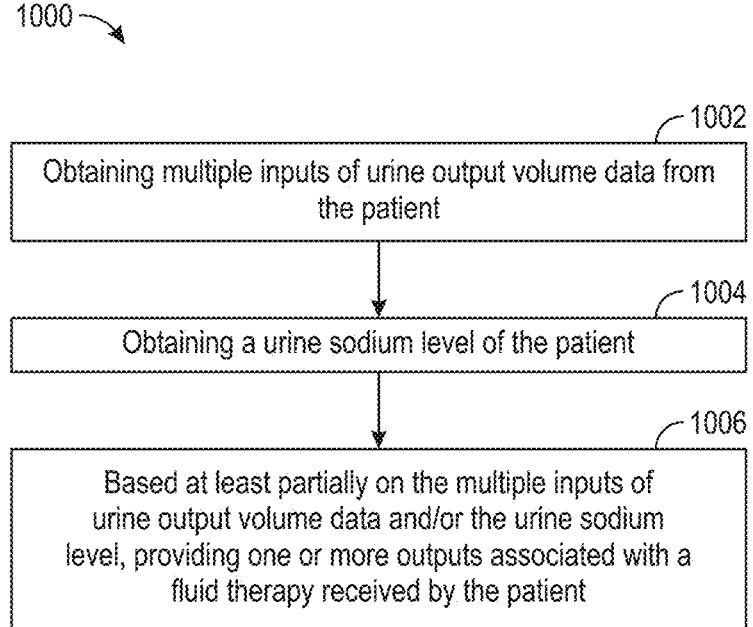
FIG. 10 is a block diagram illustrating a method of providing outputs associated with a patient's fluid therapy based at least partially on a urine output (e.g., a urine output rate) and a urine sodium level of the patient, in accordance with embodiments of the present technology.

FIG. 10 is a block diagram illustrated a method 1000 of providing outputs associated with a patient's fluid therapy based at least partially on a urine output (e.g., a urine output rate) and a urine sodium level of the patient, in accordance with embodiments of the present technology. The method 1000 is illustrated as a series of steps, acts, processes, process portions, and/or blocks 1002-1006. At least some of the blocks 1002-1006 can be performed by a fluid management system and/or one or more components thereof, such as the system 100 and/or the controller 140 of FIG. 1.

At block 1002, the method 1000 includes obtaining multiple inputs of urine output volume data from the patient. Block 1002 can be at least generally similar or identical to block 312 (FIG. 3B).

At block 1004, the method 1000 includes obtaining a urine sodium level (e.g., concentration) of the patient. The sodium concentration of excreted urine is an important measure of health of a heart failure patient undergoing fluid therapy. For example, one of the functions of the kidney is to vary the sodium content of excreted urine in order to maintain serum sodium at a consistent level. One of the drivers of worsening heart failure is the derangement of the patient's native sodium regulation mechanisms. When urine sodium concentration drops below a certain level (e.g., 75 millimoles per liter ("mmol/L")), this may indicate that the kidneys are retaining sodium to maintain serum sodium levels. If urine sodium concentration rises above a certain level (e.g., 100 mmol/L), this may indicate that the kidneys are excreting excess sodium to maintain appropriate serum sodium levels. The urine sodium level can be determined in a number of ways, including by the user entering in the value of a lab-measured urine sodium concentration and/or based on a sensor that measures the patient's urine sodium concentration (i.e., ion selective electrode, conductivity sensor) and/or one or more characteristics of the patient's urine that are associated with the patient's urine sodium level. In at least some embodiments, for example, obtaining the urine sodium level of the patient can include obtaining the urine sodium level based at least partially on a conductivity of one or more of the multiple inputs of urine output obtained from the patient. Urine conductivity is highly correlated with urine sodium levels and is thus a good surrogate for urine sodium. Additionally, measuring urine conductivity is generally less expensive and easier than measuring sodium directly and can provide a signal that is, e.g., more robust and/or less noisy.

During fluid therapy, sodium containing fluid (e.g., hydration fluid, such as 0.9% saline) can be infused to the patient based at least partially on the patient's urine output. If it is determined (e.g., via the controller 140; FIG. 1) that the patient's urine sodium concentration is dropping and the patient is receiving normal amounts of hydration fluid, there is a potential risk that continued hydration fluid administration could push the patient into a serum sodium positive state. Thus, if the patient's urine sodium drops, the fluid therapy system (e.g., the controller 140) may suggest modifications to the therapy to maintain safety and/or prevent harm to the patient. If, on the other hand, the patient's urine sodium concentration is high, the fluid therapy system may not make or suggest any modifications to the patient's fluid therapy, as a high urine sodium concentration indicates that the patient's kidneys are tolerating therapy well. In some embodiments, the hydration fluid infusion rate may be reduced based at least partially on the patient's urine sodium level in order to maximize the net fluid and/or net sodium removed from the patient.

In some embodiments, obtaining the urine conductivity includes measuring the urine conductivity using one or more conductivity sensors. The urine conductivity can be measured continuously or intermittently via the one or more conductivity sensors. The measured urine conductivity can be used to provide a corresponding urine sodium concentration. For example, the controller 140 (FIG. 1) can estimate or determine the patient's urine sodium concentration based at least in part on the urine conductivity measurements. In some embodiments, obtaining the urine conductivity further includes determining a urine temperature of the patient. The conductivity of urine varies with temperature, so obtaining the urine temperature can allow for temperature-based compensation of the conductivity signal, which is expected to yield more accurate urine conductivity readings.

In some embodiments, prior to obtaining the urine conductivity, the method 1000 includes calibrating the one or more urine conductivity sensors and/or one or more urine sodium concentration sensors. For example, in some embodiments fluid having a known electrolyte content (e.g., saline solution with a known sodium content) is used to prime and/or flush the fluid line 119 and/or any sensors fluidly coupled thereto. Because the fluid has a known electrolyte content, readings from the urine sodium concentration sensors and/or the urine conductivity sensors can be calibrated during the flushing stage.

In block 1006, the method 1000 includes providing one or more outputs associated with a fluid therapy received by the patient. Generally, the one or more outputs can include one or more alerts or notifications provided to, e.g., a user or practitioner, and/or one or more modifications or adjustments to the patient's fluid therapy. One or more of the outputs can be based at least partially on the multiple inputs of urine output volume data (block 1002) and/or a change thereto, and/or the urine conductivity and/or sodium concentration (block 1004) and/or a change thereto. For example, if urine sodium concentration (or an indication thereof) drops, as measured indirectly by urine conductivity, the fluid therapy system may suggest one or more modifications to maintain safety and/or prevent harm to the patient. Although described as providing suggestions, those of ordinary skill in the art will appreciate that, in at least some embodiments, the one or more outputs can cause the system to automatically modify the therapy as described in the suggestion to adjust or optimize the therapy, such as by modifying the level of hydration fluid matching of urine output, modifying the diuretic dosage rate, and/or combinations thereof.

If the urine conductivity corresponds to a urine sodium concentration less than or equal to a low urine sodium concentration threshold (e.g., less than or equal to 75 mmol/L, and/or that decreases by at least 5%, 10%, 15%, 20%, 30%, and/or combinations thereof over a predetermined time period of, e.g., at least 15 minutes, 30 minutes, 1 hour, 2 hours, 6 hours, 12 hours, 24 hours, and/or combinations thereof) and the urine output is less than or equal to a low urine output threshold (e.g., a urine output rate of less than 325 mL/hr averaged over the previous 3 hours, an integral debt function where the debt is more than 150 mL over the previous 3 hours, and/or decreases by at least 5%, 10%, 15%, 20%, 30%, and/or combinations thereof over a predetermined time period of, e.g., at least 15 minutes, 30 minutes, 1 hour, 2 hours, 6 hours, 12 hours, 24 hours, and/or combinations thereof), the one or more outputs can include an alert that the patient's urine sodium concentration is low and/or dropping, a prompt to actively monitor urine sodium, serum sodium, and/or other patient electrolytes, and/or a prompt to modify or stop the therapy. Additionally or alternatively, the alert can include one or more suggested therapy modifications, such as a change (e.g., increase) to the hydration fluid infusion rate, a change to the rate or percentage matching of infused saline to urine output, and/or a change (e.g., increase) to the rate of diuretic infusion.

In one example, during block 1006, the system can adjust the hydration fluid matching percentage such that the amount of infused sodium in the infused hydration fluid matches the amount of indicated sodium that would be infused in the standard algorithm for the same volume of sodium output, assuming a high urine sodium level (e.g., 135 mmol/L). For instance, using 135 mmol/L of urine sodium as the value to normalize to, if the patient outputs 1,050 mL of urine with a measured, estimated, or calculated urine sodium concentration of 67.5 mmol/L, the urine volume with the equivalent sodium content of 135 mmol/L urine is 525 mL (i.e., 1050*67.5/135=525). In this embodiment, the saline volume replaced for 525 mL of "normalized" urine is 250 mL of normal saline, thus the 1,050 mL of urine with a sodium concentration of 67.5 mmol/L would also be replaced with 250 mL of normal saline in order to achieve the equivalent sodium balance. While urine sodium levels that exceed 135 mmol/L could be replaced with higher levels of sodium containing fluid, in other embodiments such replacement could be omitted or performed at a lesser rate to, e.g., maximize net sodium removal.

If the indicated urine sodium concentration is less than or equal to the low urine sodium concentration threshold and the urine output is equal to or greater than a high urine output threshold (e.g., more than 625 mL/hr averaged over the previous 3 hours, and/or increases by at least 5%, 10%, 15%, 20%, 30%, and/or combinations thereof over a predetermined time period of, e.g., at least 15 minutes, 30 minutes, 1 hour, 2 hours, 6 hours, 12 hours, 24 hours, and/or combinations thereof), the one or more outputs can include an alert that the patient's urine sodium concentration is high and/or increasing, a prompt to actively monitor urine sodium, serum sodium, and/or other patient electrolytes, and/or a prompt to modify or stop the therapy. For example, the prompt to modify the therapy can include a prompt to reduce saline matching, reduce the hydration fluid infusion rate, and/or increase the diuretic dosage rate.

If the indicated urine sodium concentration is less than or equal to the low urine sodium concentration threshold and the urine output is between the low urine output threshold (of, e.g., 325 mL/hr) and the high urine output threshold (of, e.g., 625 mL/hr), the one or more outputs can include an alert that the patient's urine sodium concentration is acceptable, a prompt to actively monitor urine sodium, serum sodium, and/or other patient electrolytes, and/or a prompt to continue therapy and/or that therapy modifications are not needed at this time.

If, on the other hand, the indicated urine sodium concentration is high, it suggests that the patient's kidney is tolerating therapy well. More specifically, if the indicated urine sodium concentration is equal to or greater than a high urine sodium concentration threshold (e.g., greater than or equal to 100 mmol/L, and/or increases by at least 5%, 10%, 15%, 20%, 30%, and/or combinations thereof over a predetermined time period of, e.g., at least 15 minutes, 30 minutes, 1 hour, 2 hours, 6 hours, 12 hours, 24 hours, and/or combinations thereof), and the urine output is less than or equal to the low urine output threshold (of, e.g., 325 mL/hr), the one or more outputs can include a prompt to increase the diuretic dosage rate, administer an additional diuretic, and/or stop the patient's therapy.

If the indicated urine sodium concentration is equal to or greater than the high urine sodium concentration threshold (of, e.g., 100 mmol/L) and the urine output is equal to or greater than the high urine output threshold (of, e.g., 625 mL/hr), the one or more outputs can include a prompt to reduce hydration fluid matching, e.g., to maximize fluid and/or salt removal from the patient.

If the indicated urine sodium concentration is equal to or greater than the high urine sodium concentration threshold (of, e.g., 100 mmol/L) and the urine output is between the low urine output threshold (of, e.g., 325 mL/hr) and the high urine output threshold (of, e.g., 625 mL/hr), the one or more outputs can include a prompt to increase the diuretic dosage rate and/or escalate the fluid therapy. In some embodiments, when the indicated urine sodium concentration is equal to or greater than the high urine sodium concentration threshold and the urine output is between the low urine output threshold and the high urine output threshold, the one or more outputs include the prompt to increase the diuretic dosage rate and/or escalate the fluid therapy only if the urine output is decreasing. In some embodiments, the urine sodium excretion rate, which can be determined by multiplying the urine rate by the urine sodium concentration (units of mmol/hr), is another measure of the patient's urine sodium level that can be used to determine one or more of the adjustments described above. Additional details regarding adjusting fluid therapy based on urine sodium can be found in U.S. Pub. No. 2024/0260874, filed Feb. 6, 2024, and U.S. application Ser. No. 18/883,677, filed Sep. 12, 2024. Each of the above-identified applications is hereby incorporated herein by reference.

IV. Examples

Additional aspects of various embodiments of the present technology are described with reference to the following examples:

1. A fluid therapy system, comprising:
   a urine measurement device configured to measure urine output from a patient without using an indwelling catheter;
   a pump configured to provide a diuretic or a hydration fluid to the patient; and
   one or more processors configured to—
      cause the pump to provide the diuretic or the hydration fluid to the patient at a fluid rate,
      obtain, via the urine measurement device, a first input of urine output volume data from the patient,
      obtain, via the urine measurement device, a second input of urine output volume data from the patient, wherein obtaining the second input occurs at least 15 minutes after obtaining the first input,
      determine an accumulated volume of urine output for the patient based at least partially on the first input and the second input, and
      adjust the fluid rate based at least partially on the accumulated volume of urine output.

2. The fluid therapy system of example 1, wherein the one or more processors are further configured to obtain, via the urine measurement device, a third input of urine output volume data from the patient, wherein obtaining the third input occurs at least 15 minutes after obtaining the second input, and wherein the accumulated volume of urine output is based at least partially on the first input, the second input, and the third input.

3. The fluid therapy system of example 1 or example 2, wherein:
   the fluid rate is a diuretic dosage rate;
   the one or more processors are further configured to—
      determine that the accumulated volume of urine output is less than a predetermined urine output volumetric threshold, and
      recommend an increase to the diuretic dosage rate; and
   the adjustment to the fluid rate is the recommended increase to the diuretic dosage rate.

4. The fluid therapy system of any of examples 1-3, wherein the one or more processors are further configured to receive an input from a user associated with transitioning the patient to use an indwelling catheter.

5. The fluid therapy system of any of examples 1-4, wherein the fluid rate is a first fluid rate and wherein the one or more processors are further configured to adjust the fluid rate by causing the pump to provide the hydration fluid to the patient at a second fluid rate no greater than 500 ml/hr.

6. The fluid therapy system of any of examples 1-5 wherein the accumulated volume is a first accumulated volume, wherein the fluid rate is a diuretic dosage rate, and wherein, to adjust the diuretic dosage rate, the one or more processors are configured to:

cause an increase to the diuretic dosage rate by a predetermined amount and/or over a predetermined time period of no less than 120 minutes;

obtain, via the urine measurement device, a third input of urine output volume data from the patient, obtain, via the urine measurement device, a fourth input of urine output volume data from the patient, wherein obtaining the fourth input occurs at least 15 minutes after obtaining the third input;

determine a second accumulated volume of urine output based at least partially on the third input and the fourth input;

determining whether the second accumulated volume of urine output data is greater than a urine output volumetric threshold; and when the second accumulated volume of urine output data is greater than the urine output volumetric threshold, stop the increase to the diuretic dosage rate.

7. The fluid therapy system of any of examples 1-6 wherein:

the first input and the second input are obtained over a second time period;

the fluid rate is a hydration fluid rate; and the one or more processors are configured to— adjust the hydration fluid rate by causing a second amount of hydration fluid to be administered to the patient, wherein the second amount is a predetermined percentage of the accumulated volume; and during a first time period before the second time period— obtain, via the urine measurement device, a third input of urine output volume data from the patient, obtain, via the urine measurement device, a fourth input of urine output volume data from the patient, wherein obtaining the fourth input occurs at least 15 minutes after obtaining the third input, and cause a first amount of hydration fluid to be administered to the patient, wherein the first amount is equal to a total urine output volume during the first time period up to a hydration fluid threshold.

8. A method for providing fluid therapy to a patient, the method comprising:

obtaining multiple inputs of urine output volume data from the patient without using an indwelling catheter, wherein the multiple inputs include a first input obtained at a first time, and a second input obtained at a second time at least 30 minutes after the first time;

determining an accumulated volume of urine output for the patient based at least partially on the multiple inputs; and adjusting a hydration fluid rate at which a hydration fluid is provided to the patient and/or a diuretic dosage rate at which a diuretic is provided to the patient based at least partially on the accumulated volume of urine output.

9. The method of example 8, wherein obtaining the multiple inputs of urine output volume data includes obtaining the multiple inputs of urine output volume data via an external catheter.

10. The method of example 8 or example 9, further comprising determining a urine output rate by considering the second input and time elapsed between the second time and the first time.

11. The method of any of examples 8-10, wherein adjusting the hydration fluid rate and/or the diuretic dosage rate is based at least partially on the accumulated volume and/or the multiple inputs from at least a prior 60 minutes.

12. The method of any of examples 8-11, wherein the multiple inputs include a volume of urine at or above a minimum urine volume threshold of 50 milliliters.

13. The method of any of examples 8-12, wherein the multiple inputs are received no less than 60 minutes apart from one another.

14. The method of examples 8-13, further comprising receiving an input from a user associated with transitioning the patient to using an indwelling catheter.

15. One or more non-transitory computer-readable medium having instructions that, when executed by one or more processors, cause a fluid therapy system to perform operations comprising:

obtaining multiple inputs of urine output volume data from a patient without using an indwelling catheter, wherein the multiple inputs include a first input obtained at a first time, and a second input obtained at a second time at least 30 minutes after the first time;

determining an accumulated volume of urine output for the patient based at least partially on the multiple inputs; and adjusting a hydration fluid rate at which a hydration fluid is provided to the patient and/or a diuretic dosage rate at which a diuretic is provided to the patient based at least partially on the accumulated volume of urine output.

16. The one or more non-transitory computer-readable medium of example 15, wherein the multiple inputs further include a third input obtained at a third time at least 30 minutes after the first time.

17. The one or more non-transitory computer-readable medium of example 15 or example 16, wherein adjusting the hydration fluid rate and/or the diuretic dosage rate is based at least partially on the accumulated volume and/or the multiple inputs from at least a prior 60 minutes.

18. The one or more non-transitory computer-readable medium of any of examples 15-17, wherein the operations further comprise:

infusing the diuretic to the patient at the diuretic dosage rate; and only after obtaining the multiple inputs of urine output volume data from the patient, infusing the hydration fluid to the patient at the hydration fluid rate based on the multiple inputs.

19. The one or more non-transitory computer-readable medium of any of examples 15-18, wherein the operations further comprise receiving an input from a user associated with transitioning the patient to an indwelling catheter.

20. The one or more non-transitory computer-readable medium of any of examples 15-19, wherein:

determining the accumulated volume of urine output includes adding the first input to the second input;

obtaining the multiple inputs includes obtaining the multiple inputs over a time period;

the operations further comprise determining an estimated urine output rate for the patient over the time period by dividing the accumulated volume of urine output by the time period; and adjusting the hydration fluid rate and/or the diuretic dosage rate is based at least partially on the estimated urine output rate.

V. Conclusion

It will be apparent to those having skill in the art that changes may be made to the details of the above-described embodiments without departing from the underlying principles of the present technology. In some cases, well known structures and functions have not been shown or described in detail to avoid unnecessarily obscuring the description of the embodiments of the present technology. Although blocks of methods may be presented herein in a particular order, alternative embodiments may perform the blocks in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing concentrations, pressures, and other numerical values used in the specification and claims, are to be understood as being modified in all instances by the term "about." As used herein, the use of relative terminology, such as "about", "approximately", "substantially" and the like refer to the stated value plus or minus ten percent. For example, the use of the term "about 100" refers to a range of from 90 to 110, inclusive. In instances in which the context requires otherwise and/or relative terminology is used in reference to something that does not include a numerical value, the terms are given their ordinary meaning to one skilled in the art. Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

We claim:

1. A fluid therapy system, comprising:
a non-indwelling catheter configured to receive urine from a patient,
a urine measurement device configured to measure urine output from the patient and configured to be fluidly coupled to the non-indwelling catheter;
a pump configured to provide a diuretic or a hydration fluid to the patient; and
one or more processors configured to—
cause the pump to provide the diuretic or the hydration fluid to the patient at a fluid rate,
obtain, via the urine measurement device, a first input of urine output volume data from the patient,
obtain, via the urine measurement device, a second input of urine output volume data from the patient, wherein obtaining the second input occurs at least 15 minutes after obtaining the first input,
determine an accumulated volume of urine output for the patient based at least partially on the first input and the second input, and
adjust the fluid rate based at least partially on the accumulated volume of urine output.

2. The fluid therapy system of claim 1, wherein the one or more processors are further configured to obtain, via the urine measurement device, a third input of urine output volume data from the patient, wherein obtaining the third input occurs at least 15 minutes after obtaining the second input, and wherein the accumulated volume of urine output is based at least partially on the first input, the second input, and the third input.

3. The fluid therapy system of claim 1, wherein:
the fluid rate is a diuretic dosage rate;
the one or more processors are further configured to—
determine that the accumulated volume of urine output is less than a predetermined urine output volumetric threshold, and
recommend an increase to the diuretic dosage rate; and
the adjustment to the fluid rate is the recommended increase to the diuretic dosage rate.

4. The fluid therapy system of claim 1, wherein the one or more processors are further configured to receive an input from a user associated with transitioning the patient to use an indwelling catheter.

5. The fluid therapy system of claim 1, wherein the fluid rate is a first fluid rate and wherein the one or more processors are further configured to adjust the fluid rate by causing the pump to provide the hydration fluid to the patient at a second fluid rate no greater than 500 ml/hr.

6. The fluid therapy system of claim 1 wherein the accumulated volume is a first accumulated volume, wherein the fluid rate is a diuretic dosage rate, and wherein, to adjust the diuretic dosage rate, the one or more processors are configured to:

cause an increase to the diuretic dosage rate by a predetermined amount and/or over a predetermined time period of no less than 120 minutes;

obtain, via the urine measurement device, a third input of urine output volume data from the patient, obtain, via the urine measurement device, a fourth input of urine output volume data from the patient, wherein obtaining the fourth input occurs at least 15 minutes after obtaining the third input;

determine a second accumulated volume of urine output based at least partially on the third input and the fourth input;

determining whether the second accumulated volume of urine output data is greater than a urine output volumetric threshold; and when the second accumulated volume of urine output data is greater than the urine output volumetric threshold, stop the increase to the diuretic dosage rate.

7. The fluid therapy system of claim 1 wherein:

the first input and the second input are obtained over a second time period;

the fluid rate is a hydration fluid rate; and the one or more processors are configured to— adjust the hydration fluid rate by causing a second amount of hydration fluid to be administered to the patient, wherein the second amount is a predetermined percentage of the accumulated volume; and during a first time period before the second time period— obtain, via the urine measurement device, a third input of urine output volume data from the patient, obtain, via the urine measurement device, a fourth input of urine output volume data from the patient, wherein obtaining the fourth input occurs at least 15 minutes after obtaining the third input, and cause a first amount of hydration fluid to be administered to the patient, wherein the first amount is equal to a total urine output volume during the first time period up to a hydration fluid threshold.

8. One or more non-transitory computer-readable medium having instructions that, when executed by one or more processors, cause a fluid therapy system to perform operations comprising:

obtaining multiple inputs of urine output volume data from a patient over a time period and without using an indwelling catheter, wherein the multiple inputs include a first input obtained at a first time, and a second input obtained at a second time at least 30 minutes after the first time;

determining an accumulated volume of urine output for the patient by adding the first input to the second input;

determining an estimated urine output rate for the patient over the time period by dividing the accumulated volume of urine output by the time period; and adjusting a hydration fluid rate at which a hydration fluid is provided to the patient and/or a diuretic dosage rate at which a diuretic is provided to the patient based at least partially on the estimated urine output rate.

9. The one or more non-transitory computer-readable medium of claim 8, wherein the multiple inputs further include a third input obtained at a third time at least 30 minutes after the first time.

10. The one or more non-transitory computer-readable medium of claim 8, wherein adjusting the hydration fluid rate and/or the diuretic dosage rate is based at least partially on the estimated urine output rate from at least a prior 60 minutes.

11. The one or more non-transitory computer-readable medium of claim 8, wherein the operations further comprise:

infusing the diuretic to the patient at the diuretic dosage rate; and only after obtaining the multiple inputs of urine output volume data from the patient, infusing the hydration fluid to the patient at the hydration fluid rate based on the estimated urine output rate.

12. The one or more non-transitory computer-readable medium of claim 8, wherein the operations further comprise receiving an input from a user associated with transitioning the patient to an indwelling catheter.

13. One or more non-transitory computer-readable medium having instructions that, when executed by one or more processors, cause a fluid therapy system to perform operations comprising:

obtaining over a time period multiple inputs of urine output volume data from a patient using a non-indwelling catheter, wherein the multiple inputs include a first input obtained at a first time, and a second input obtained at a second time at least 30 minutes after the first time;

determining an estimated urine output rate for the patient based at least partially on the first input, the second input, and the time period; and obtaining a hydration fluid rate at which a hydration fluid is provided to the patient and/or a diuretic dosage rate at which a diuretic is provided to the patient based at least partially on the estimated urine output rate.

* * * * *